(12) United States Patent
Kosinski et al.

(10) Patent No.: US 10,919,839 B2
(45) Date of Patent: Feb. 16, 2021

(54) SILICON-CONTAINING COMPOSITIONS AND THEIR METHODS OF USE

(71) Applicant: Aditya Birla Chemicals (USA) LLC, Charlotte, NC (US)

(72) Inventors: Szymon Kosinski, Hayward, CA (US); Stefan J. Pastine, San Francisco, CA (US)

(73) Assignee: Aditya Birla Chemicals (USA) LLC, Charlotte, NC (US)

( * ) Notice: Subject to any disclaimer, the term of this patent is extended or adjusted under 35 U.S.C. 154(b) by 53 days.

(21) Appl. No.: 16/005,550

(22) Filed: Jun. 11, 2018

(65) Prior Publication Data

US 2019/0016870 A1 Jan. 17, 2019

Related U.S. Application Data

(60) Provisional application No. 62/530,933, filed on Jul. 11, 2017.

(51) Int. Cl.
| | | |
|---|---|---|
| *C08J 11/16* | (2006.01) | |
| *C07C 217/08* | (2006.01) | |
| *C07C 213/08* | (2006.01) | |
| *C08G 59/50* | (2006.01) | |
| *C08J 11/26* | (2006.01) | |
| *C08G 59/06* | (2006.01) | |
| *C08G 59/40* | (2006.01) | |

(52) U.S. Cl.
CPC .......... *C07C 217/08* (2013.01); *C07C 213/08* (2013.01); *C08G 59/066* (2013.01); *C08G 59/4085* (2013.01); *C08G 59/504* (2013.01); *C08J 11/16* (2013.01); *C08J 11/26* (2013.01); *C08J 2363/00* (2013.01); *C08J 2379/02* (2013.01)

(58) Field of Classification Search
CPC .............................. C08J 11/16; C08G 59/4014
See application file for complete search history.

(56) References Cited

U.S. PATENT DOCUMENTS

| | | | |
|---|---|---|---|
| 2,363,464 A | 11/1944 | Murray et al. | |
| 2,409,675 A | 10/1946 | Gresham | |
| 2,425,628 A | 8/1947 | Loder et al. | |
| 3,293,298 A | 12/1966 | Szabo | |
| 3,462,393 A | 8/1969 | Legler | |
| 3,501,528 A | 3/1970 | Ott | |
| 3,558,709 A | 1/1971 | Gunter | |
| 3,786,029 A | 1/1974 | Bechara | |
| 3,879,465 A | 4/1975 | Bechara et al. | |
| 4,003,933 A | 1/1977 | Drake | |
| 4,136,092 A | 1/1979 | Jackie et al. | |
| 4,177,173 A | 12/1979 | Carr | |
| 4,235,821 A | 11/1980 | Butte, Jr. et al. | |
| 4,252,936 A | 2/1981 | Rinde et al. | |
| 4,313,004 A | 1/1982 | Kluger et al. | |
| 4,328,331 A | 5/1982 | Chen et al. | |
| 4,495,317 A | 1/1985 | Albers | |
| 4,552,815 A | 11/1985 | Dreher et al. | |
| 4,581,423 A | 4/1986 | Speranza et al. | |
| 4,820,743 A | 4/1989 | Ishikawa et al. | |
| 4,929,661 A | 5/1990 | Noomen et al. | |
| 5,191,015 A | 3/1993 | Sheppard et al. | |
| 5,298,618 A | 3/1994 | Speranza et al. | |
| 5,310,789 A | 5/1994 | Furihata et al. | |
| 5,338,568 A | 8/1994 | Lohnes et al. | |
| 5,891,367 A | 4/1999 | Basheer et al. | |
| 5,932,682 A | 8/1999 | Buchwalter et al. | |
| 6,790,995 B2 | 9/2004 | Pfeffinger et al. | |
| 8,785,694 B2 | 7/2014 | Pastine | |
| 9,080,004 B2 | 7/2015 | Abrami et al. | |
| 9,862,797 B2 | 1/2018 | Pastine | |
| 10,214,479 B2 | 2/2019 | Kosinski et al. | |
| 2002/0045057 A1 | 4/2002 | Guritza | |
| 2005/0234216 A1 | 10/2005 | Klein et al. | |
| 2006/0014924 A1 | 1/2006 | Hanley et al. | |
| 2008/0207655 A1 | 8/2008 | Dillon et al. | |
| 2009/0030125 A1 | 1/2009 | Vedage et al. | |
| 2009/0048370 A1 | 2/2009 | Lutz et al. | |
| 2009/0137777 A1 | 5/2009 | Iwashima et al. | |
| 2009/0192265 A1 | 7/2009 | Hasegawa et al. | |
| 2010/0184890 A1 | 7/2010 | Constantinescu et al. | |
| 2011/0048637 A1 | 3/2011 | Kohli | |
| 2011/0244245 A1 | 10/2011 | Elgimiabi | |
| 2012/0012505 A1 | 1/2012 | Compton | |
| 2012/0301726 A1 | 11/2012 | Staunton et al. | |
| 2013/0245204 A1 | 9/2013 | Pastine et al. | |

(Continued)

FOREIGN PATENT DOCUMENTS

| | | | |
|---|---|---|---|
| CN | 102816346 A | 12/2012 | |
| DE | 1125171 B | 3/1962 | |

(Continued)

OTHER PUBLICATIONS

Bassampour et al., "Degradable epoxy resins based on bisphenol A diglycidyl ether and silyl ether amine curing agents", Journal of Applied Polymer Science, (2017), App 44620, pp. 1-9.

Bradley et al., "Alkoxides of vanadium (IV)", Canadian Journal of Chemistry (1962), vol. 40, pp. 1183-1188.

Bunyan et al., "Reactivity of organophosphorus compounds. XIII. Radical-chain transfer reactions of triethyl phosphite: a new phosphorothiolate synthesis", Journal of the Chemical Society (1962), pp. 2953-2958.

Emblem et al., "Preparation and properties of some aminoalkoxysilanes", Journal of Applied Chemistry (1962), vol. 12, pp. 5-9.

International Search Report and Written Opinion for corresponding International Application No. PCT/CN2011/076980, dated Oct. 13, 2011.

(Continued)

*Primary Examiner* — Kuo Liang Peng
(74) *Attorney, Agent, or Firm* — Goodwin Procter LLP

(57) ABSTRACT

Provided herein are silicon-containing recyclable polyamino compounds; epoxy resin compositions containing these silicon-containing reworkable or recyclable polyamino compounds; and methods of their use.

20 Claims, 6 Drawing Sheets

(56) References Cited

U.S. PATENT DOCUMENTS

| | | |
|---|---|---|
| 2013/0324764 A1 | 12/2013 | Pastine |
| 2014/0221510 A1 | 8/2014 | Liang et al. |
| 2014/0357802 A1 | 12/2014 | Aou et al. |
| 2015/0050659 A1 | 2/2015 | Sebo et al. |
| 2015/0361230 A1 | 12/2015 | Curran et al. |
| 2016/0229949 A1 | 8/2016 | Qin et al. |
| 2016/0264717 A1* | 9/2016 | Pastine ................ C07C 217/08 |

FOREIGN PATENT DOCUMENTS

| | | |
|---|---|---|
| GB | 846377 A | 8/1960 |
| JP | 1225635 | 9/1989 |
| WO | 2009126933 A2 | 10/2009 |

OTHER PUBLICATIONS

International Search Report and Written Opinion for corresponding International Application No. PCT/US2013/044346, dated Nov. 5, 2013.

International Search Report and Written Opinion for corresponding International Application No. PCT/US2014/060524, dated Mar. 19, 2015.

Paramonov et al., "Fully Acid-Degradable Biocompatible Polyacetal Microparticles for Drug Delivery", Bioconjugate Chem., vol. 19, No. 4, (2008), pp. 911-919.

PubChem. Compound Summary for CID 20541457.

Shim et al., "Acid-Responsive Linear Polyethylenimine for Efficient, Specific, and Biocompatible siRNA Delivery", Bioconjugate Chem., vol. 20, No. 3, (2009), pp. 488-499.

Webb et al., Journal of the Chemical Society Journal (1962), pp. 4307-4319.

Webb et al., Journal of the Chemical Society Journal (1962), pp. 4320-4323.

International Search Report and Written Opinion for International Application No. PCT/US2019/012543, dated Apr. 10, 2019.

International Search Report and Written Opinion for International Application No. PCT/US2019/012544, dated Apr. 10, 2019.

Berge et al., "Pharmaceutical Salts", Journal of Pharmaceutical Sciences, (1977), vol. 66, pp. 1-18.

* cited by examiner

SILICON-CONTAINING COMPOSITIONS AND THEIR METHODS OF USE

CROSS-REFERENCE TO RELATED APPLICATIONS

This application claims priority to U.S. Ser. No. 62/530,933 filed Jul. 11, 2017, the contents of which are incorporated herein by reference.

BACKGROUND

Waste generation poses significant environmental and societal challenges. While some of the waste generated each year can be recycled or repurposed into new products, some materials are not currently recyclable. For example, plastics comprise 12% of waste generation in the U.S.

Thermoplastics are encountered in everyday life in the form of packaging, bottles, and casing materials, toys, etc. Little waste is created in the manufacturing of such consumer products because most common thermoplastics are recyclable, so for economic reasons, any manufacturing waste will be fed back into production. Many of these products, post-consumer, find their way into the environment.

There is a second category of high performance structural plastic called thermosetting plastics (or thermosets). While thermoplastics can be melted down from a solid and reshaped (thus recycled), thermosets are defined by an irreversible setting process. Typically, they are composed from two different liquid materials, a resin and a curing agent, which harden when mixed and heated. Once "set", thermoset materials, and products derived therefrom, cannot be melted and recycled like thermoplastics. They can only be removed from the environment via incineration. The ordinary consumer is likely unaware about the fact that there still remains a non-recyclable class of plastic. This is understandable considering that, historically, thermosets have mainly been used for adhesive and coating applications. This is changing. Thermosets, such as epoxy, are now commonly used as the plastic matrix in performance composites, also known as fiber reinforced plastics (FRPs). Composites have the lightweight advantages of a plastic and the extra strength generated from the fiber reinforcement. As the cost of carbon fiber has dropped substantially, the prevalence of carbon fiber composites has increased dramatically. Composites are now found in many familiar engineering applications, including automotive and aviation parts, wind turbine blades, structural supports in buildings, and high performance sporting equipment.

As the composite market continues to grow, the use of non-recyclable thermosets places the industry in juxtaposition. On one hand, carbon composites are essential for meeting energy efficiency goals and café standards in the transportation industry, and on the other hand the materials required to make these products are not recyclable. While attention could clearly be focused on the fact that end-of-life products are not recyclable, the waste generated by composite OEMs is increasingly becoming both an environmental and economic burden.

SUMMARY

Provided herein are removable, dissolvable and/or recyclable thermosets that may be converted into their thermoplastic counterpart via a specific recycling process. In some embodiments, provided herein are silicon-containing compositions comprising at least one siloxy functionality (e.g., an acid-labile siloxy functionality), their methods of manufacture, recycling, and use.

In one aspect, provided herein is a silicon-containing polymer composition (e.g., a recyclable silicon-containing composition, acid-labile composition) comprising at least one siloxy functionality.

In one aspect, provided herein is a silicon-containing composition (e.g., a recyclable silicon-containing composition, acid-labile composition) comprising: an epoxy resin; and a compound of Formula (I-A) or (I-B):

Formula (I-A)

Formula (I-B)

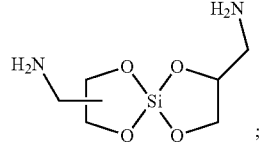

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each occurrence of $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A) is a compound of Formula (I-A-i) or (I-A-ii):

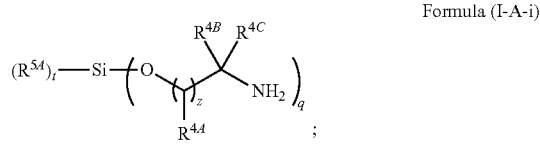

Formula (I-A-i)

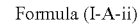

Formula (I-A-ii)

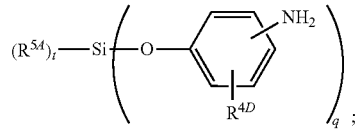

wherein: z is an integer from 1 to 6; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl (e.g., methyl, ethyl), cycloalkyl, aryl (e.g., phenyl, e.g., substituted phenyl), or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A) is a compound of Formula (I-A-iii):

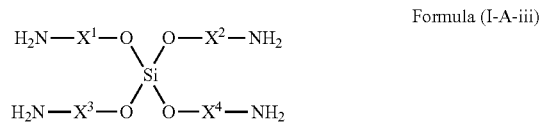

Formula (I-A-iii)

wherein: each of $X^1$, $X^2$, $X^3$, and $X^4$ is independently alkylene, cycloalkylene, heterocyclylene, alkenylene, alkynylene, cycloalkenylene, arylene, or heteroarylene.

In some embodiments, the compound is a compound of Formula (III-A) or (IV-A):

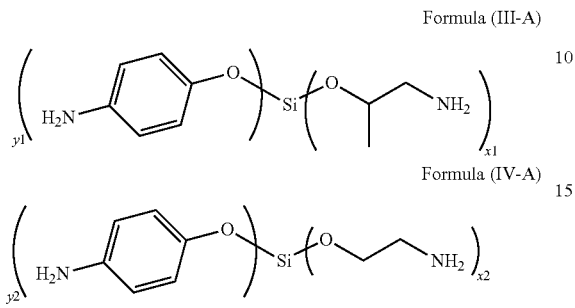

Formula (III-A)

Formula (IV-A)

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound is:

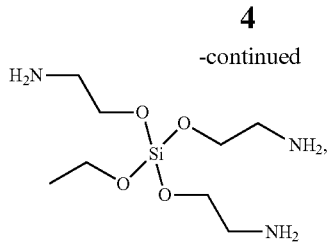

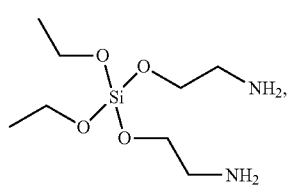

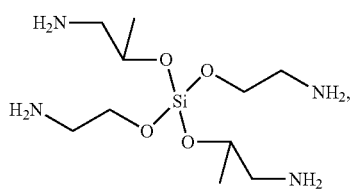

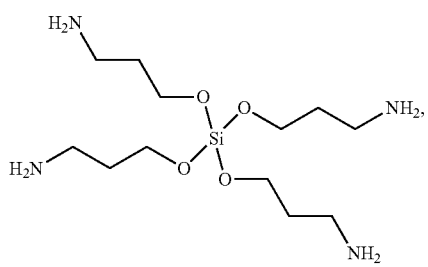

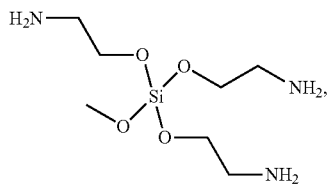

-continued

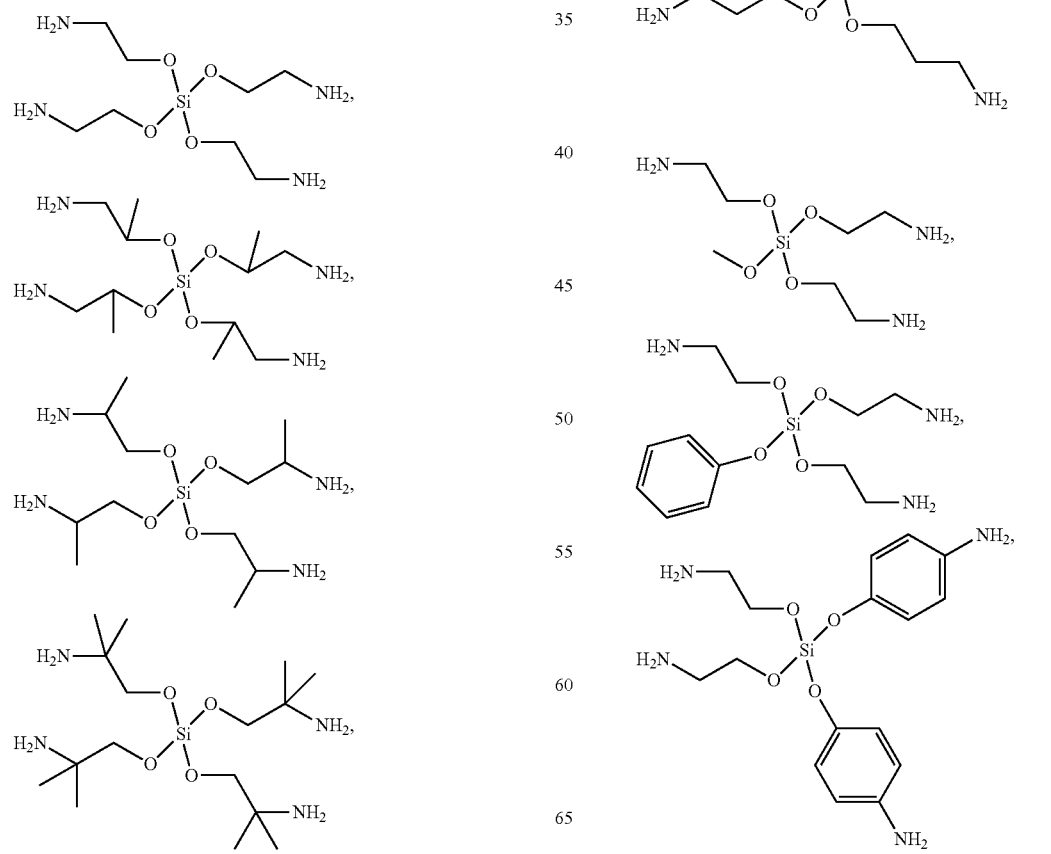

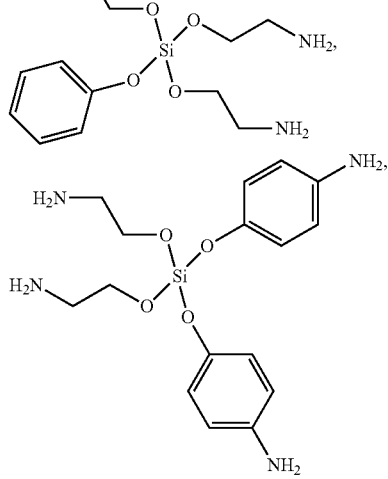

-continued

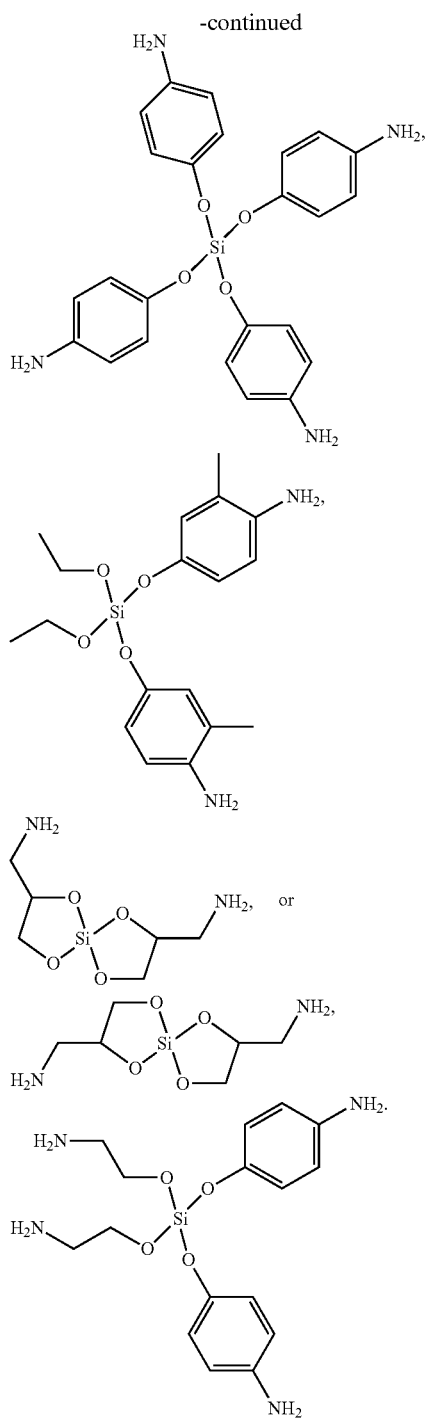

In some embodiments, the composition further comprises a polyamine curing agent compound having the Formula (II-A):

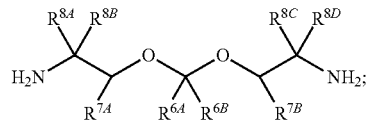

(II-A)

wherein: each of $R^{6A}$ and $R^{6B}$ is independently hydrogen or alkyl (e.g., methyl, ethyl, benzyl); and each of $R^{7A}$, $R^{7B}$, $R^{8A}$, $R^{8B}$, $R^{8C}$ and $R^{8D}$ is independently hydrogen or alkyl (e.g., methyl).

In some embodiments, the compound of Formula (II-A) is:

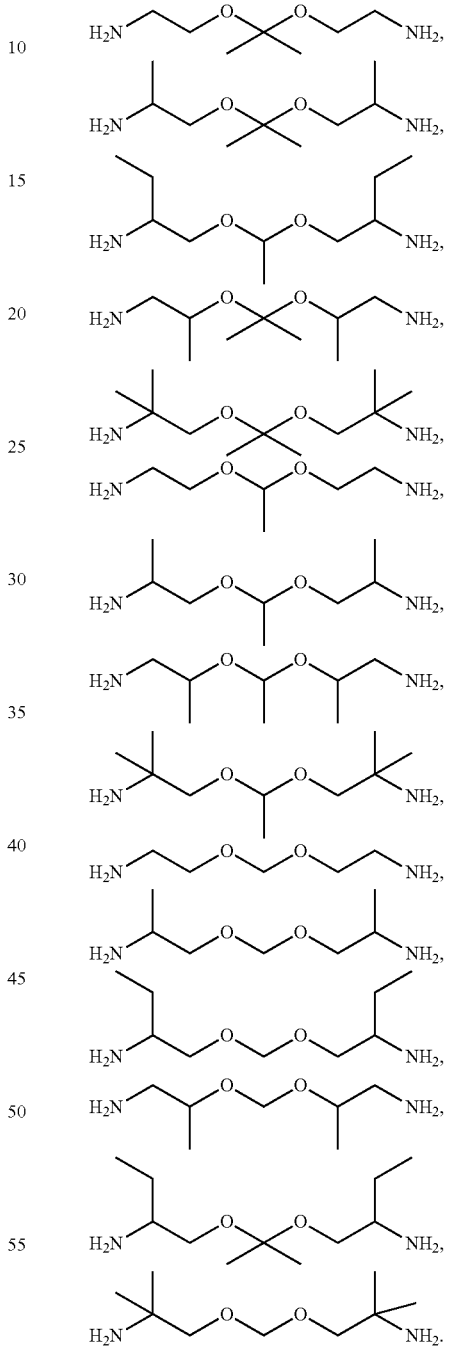

In some embodiments, the composition additionally comprises a chain extender. In some embodiments, the chain extender is a primary monoamine or secdiamine compound. In some embodiments, the chain extender is monoethanolamine, diethanolamine, 3-aminopropanol, 2-aminopropanol, 1-amino-2-propanol, 2-aminobutanol, 2-amino-2-methyl-1-propanol, piperazine, benzylamine, aniline, p-anisidine, aminophenol, butylamine, and N,N'-dimethyl-ethylenediamine, tert-butylamine, sec-butylamine, or a combination thereof.

In some embodiments, the chain extender is:

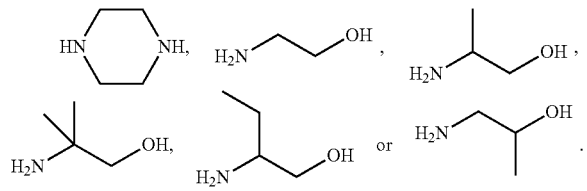

In some embodiments, the Formula (II-A) compound is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %.

In some embodiments, the siloxy molecule is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %.

In some embodiments, the epoxy resin is selected from a group consisting of glycidyl ether epoxy resin, glycidyl ester epoxy resin, glycidyl amine epoxy resin, alicyclic epoxy resin, aliphatic epoxy resin, phenolic epoxy resin, brominated epoxy resin and combinations thereof.

In some embodiments, the epoxy resin is a diepoxide resin.

In some embodiments, the epoxy resin comprises a blend of a first bisphenol-based epoxy resin having an epoxide equivalent weight (EEW) in the range of 160 to 220.

In some embodiments, the EEW is 188.

In some embodiments, the epoxy resin comprises a second bisphenol-based epoxy resin having an EEW in the range of 400 to 1500.

In some embodiments, the composition further comprises an auxiliary material selected from the group consisting of flame retardant, accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive, and combinations thereof.

In some embodiments, the composition further comprises a reinforcement material selected from a fibrous material or a non-fibrous material. In some embodiments, the composition further comprises a reinforcement material selected from glass fiber, carbon fiber, natural fiber (e.g. flax), or chemical fiber (e.g. Kevlar). In some embodiments, the composition further comprises a reinforcement material selected from non-fibrous material. In some embodiments, the reinforcement material is carbon nanotube, carbon black, metal nanoparticle, organic nanoparticle, iron oxide, boron nitride, or a combination thereof.

In some embodiments, the glass transition temperature of the epoxy resin composition described herein is greater than 80° C. but less than 170° C.

In some embodiments, the tensile strength of the epoxy resin composition described herein is greater than 7,000 psi and the tensile modulus is greater than 300,000 psi.

In some embodiments, the flexural strength of the epoxy resin composition described herein is greater than 9,000 psi and the flexural modulus is greater than 300,000 psi.

In some embodiments, the composition further comprises a reinforcing agent. In some embodiments, the reinforcing agent comprises at least one reinforcing component selected from the group consisting of glass fibers, aramid fibers, graphite fibers, carbon fibers, natural fibers, and non-natural fibers.

In some embodiments, the reinforcing agent is woven. In some embodiments, the reinforcing agent is non-woven.

In one aspect, described herein is a composition comprising the reaction product of: an epoxy resin (e.g., an epoxy resin described herein); and a compound of Formula (I-A-iv):

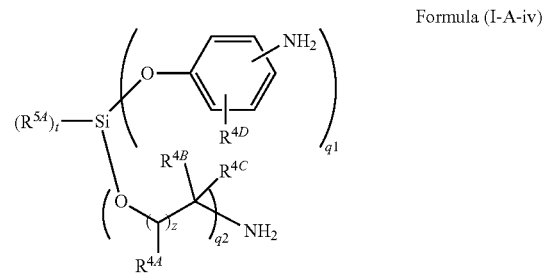

Formula (I-A-iv)

wherein: z is an integer from 1 to 6; t is an integer from 0 to 1; q1 is an integer from 1 to 4; q2 is an integer from 0 to 3; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q, and q2 is 4.

In some embodiments, the compound of Formula (I-A) is a compound of Formula (I-A-ii-1)

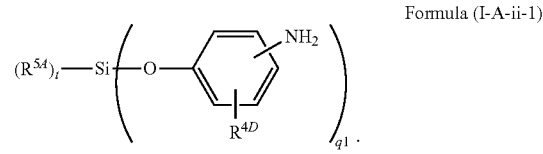

Formula (I-A-ii-1)

In some embodiments, q1 is 3, q2 is 0, and t is 1. In some embodiments, q1 is 4, q2 is 0, and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, the compound is a compound of Formula (III-A) or (IV-A):

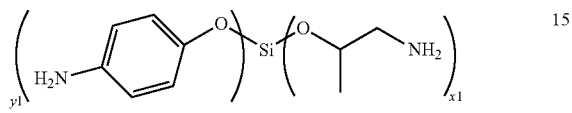

Formula (III-A)

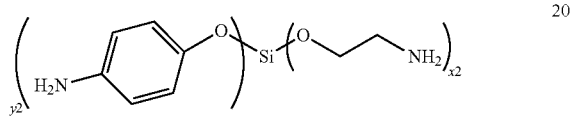

Formula (IV-A)

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound of Formula (I-A) is:

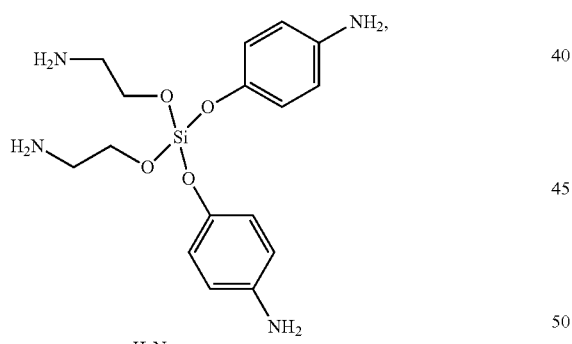

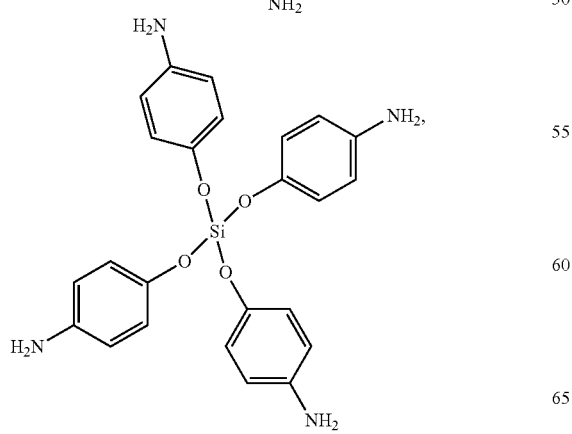

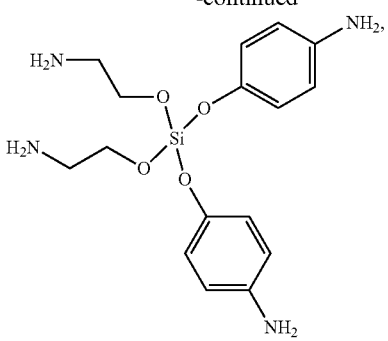

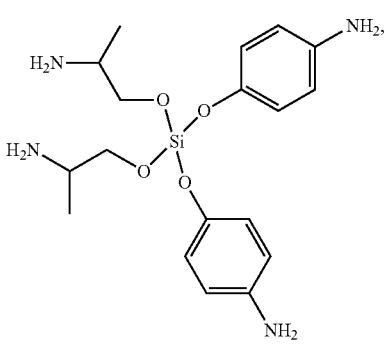

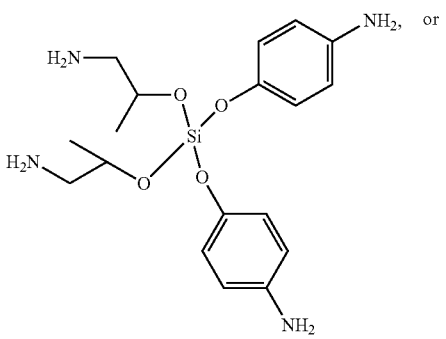

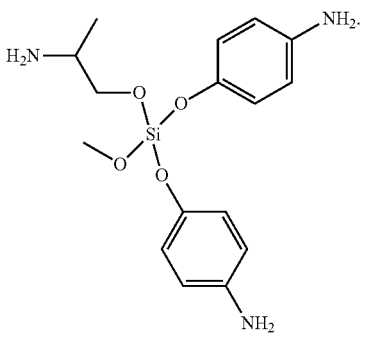 [SMILES: CO[Si](OCC(C)N)(Oc1ccc(N)cc1)Oc1ccc(N)cc1]

In some embodiments, the compound of Formula (I-A) is:

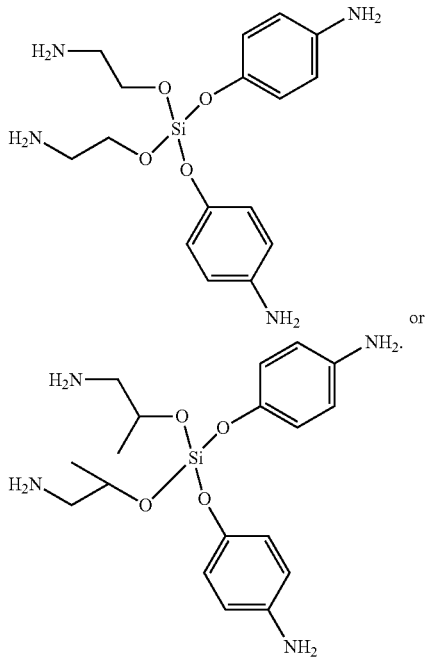

In some embodiments, the $T_g$ of the composition is from about 80° C. to 125° C. In some embodiments, the $T_g$ of the composition is greater than 82° C. In some embodiments, the $T_g$ of the composition is greater than 85° C. In some embodiments, the $T_g$ of the composition is greater than 90° C. In some embodiments, the $T_g$ of the composition is greater than 100° C. In some embodiments, the $T_g$ of the composition is greater than 120° C. In some embodiments, the tensile strength of the composition is greater than 5,500 psi. In some embodiments, the tensile strength of the composition is greater than 7,000 psi.

In some embodiments, the epoxy resin is selected from a group consisting of glycidyl ether epoxy resin, glycidyl ester epoxy resin, glycidyl amine epoxy resin, alicyclic epoxy resin, aliphatic epoxy resin, phenolic epoxy resin, brominated epoxy resin and combinations thereof.

In some embodiments, the epoxy resin is a diepoxide resin.

In some embodiments, the epoxy resin comprises a blend of a first bisphenol-based epoxy resin having an epoxide equivalent weight (EEW) in the range of 160 to 220.

In some embodiments, the EEW is 188.

In some embodiments, the epoxy resin comprises a second bisphenol-based epoxy resin having an EEW in the range of 400 to 1500.

In some embodiments, the composition further comprises an auxiliary material selected from the group consisting of flame retardant, accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive, and combinations thereof.

In some embodiments, the composition further comprises a reinforcement material selected from a fibrous material or a non-fibrous material. In some embodiments, the composition further comprises a reinforcement material selected from glass fiber, carbon fiber, natural fiber, or chemical fiber. In some embodiments, the composition further comprises a reinforcement material selected from non-fibrous material. In some embodiments, the reinforcement material is carbon nanotube, carbon black, metal nanoparticle, organic nanoparticle, iron oxide, boron nitride, or a combination thereof.

In some embodiments, the glass transition temperature of the epoxy resin composition described herein is greater than 80° C. but less than 170° C.

In some embodiments, the tensile strength of the epoxy resin composition described herein is greater than 7,000 psi and the tensile modulus is greater than 300,000 psi.

In some embodiments, the flexural strength of the epoxy resin composition described herein is greater than 9,000 psi and the flexural modulus is greater than 300,000 psi.

In some embodiments, the composition further comprises a reinforcing agent. In some embodiments, the reinforcing agent comprises at least one reinforcing component selected from the group consisting of glass fibers, aramid fibers, graphite fibers, carbon fibers, natural fibers, and non-natural fibers.

In some embodiments, the reinforcing agent is woven. In some embodiments, the reinforcing agent is non-woven.

In one aspect, described herein a composition comprising the reaction product of: an epoxy resin (e.g., an epoxy resin described herein); a compound of Formula (I-A);

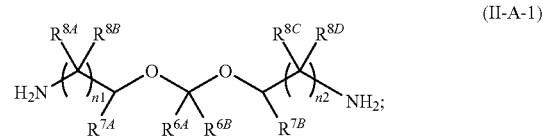

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each occurrence of $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl; and a compound having the Formula (II-A-1):

(II-A-1)

$$H_2N \underset{R^{7A}}{\overset{R^{8A}\ R^{8B}}{\bigwedge}}_{n1} O \bigwedge O \underset{R^{6A}\ R^{6B}}{\underset{R^{7B}}{\overset{R^{8C}\ R^{8D}}{\bigwedge}}}_{n2} NH_2;$$

wherein: each of $R^{6A}$ and $R^{6B}$ is independently hydrogen or alkyl (e.g., methyl, ethyl, benzyl); each of $R^{7A}$, $R^{7B}$, $R^{8A}$, $R^{8B}$, $R^{8C}$ and $R^{8D}$ is independently for each occurrence hydrogen or alkyl (e.g., methyl or ethyl); and each of n1 and n2 is independently 1 or 2 (e.g. n1 and n2 are both 1).

In some embodiments, the compound of Formula (I-A) is a compound of Formula (I-A-iv)

Formula (I-A-iv)

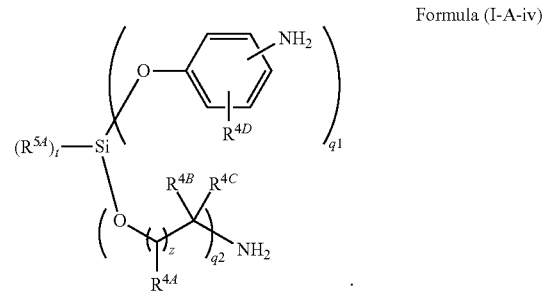

wherein: z is an integer from 1 to 6; t is an integer from 0 to 1; q1 is an integer from 0 to 4; q2 is an integer from 0 to 4; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4.

In some embodiments, the compound of Formula (I-A) is a compound of Formula (I-A-i-1) or (I-A-ii-1):

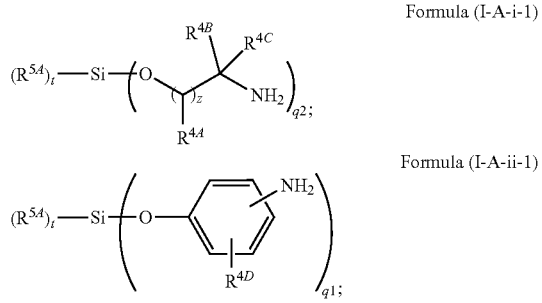

Formula (I-A-i-1)

Formula (I-A-ii-1)

wherein: z is an integer from 1 to 6; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl (e.g., methyl, ethyl), cycloalkyl, aryl (e.g., phenyl, e.g., substituted phenyl), or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A-iv-1) is a compound of Formula (I-A-i-1)

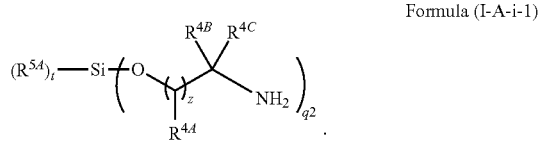

Formula (I-A-i-1)

In some embodiments, the compound of Formula (I-A-iv) is a compound of Formula (I-A-ii-1)

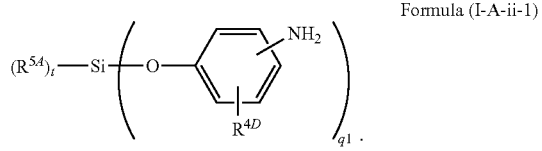

Formula (I-A-ii-1)

In some embodiments, the compound of Formula (I-A) is a compound of Formula (I-A-iii):

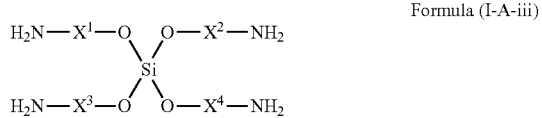

Formula (I-A-iii)

wherein: each of $X^1$, $X^2$, $X^3$, and $X^4$ is independently alkylene, cycloalkylene, heterocyclylene, alkenylene, alkynylene, cycloalkenylene, arylene, or heteroarylene.

In some embodiments, q is 2 and t is 2. In some embodiments, q is 3 and t is 1. In some embodiments, q1 is 3, q2 is 0, and t is 1. In some embodiments, q1 is 4, q2 is 0, and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, at least one of $X^1$, $X^2$, $X^3$, and $X^4$ is arylene. In some embodiments, at least one of $X^1$, $X^2$, $X^3$, and $X^4$ is phenylene optionally substituted with 1, 2, 3, or 4 occurrences of methyl (e.g., unsubstituted methyl). In some embodiments, $X^1$ and $X^3$ is phenylene optionally substituted with 1 occurrence of methyl and $X^2$ and $X^4$ is alkylene (e.g., unsubstituted $C_2$-$C_6$ alkylene, e.g., unsubstituted branched $C_2$-$C_6$ alkylene). In some embodiments, $X^1$ and $X^3$ is unsubstituted phenylene and $X^2$ and $X^4$ is alkylene (e.g., unsubstituted $C_2$-$C_6$ alkylene, e.g., unsubstituted branched $C_2$-$C_6$ alkylene).

In some embodiments, the compound is a compound of Formula (III-A) or (IV-A):

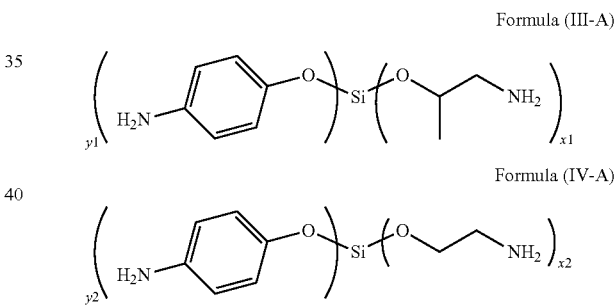

Formula (III-A)

Formula (IV-A)

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound of Formula (I-A) is:

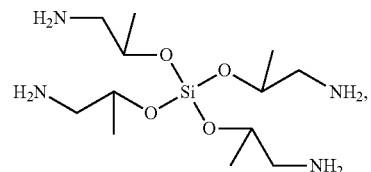

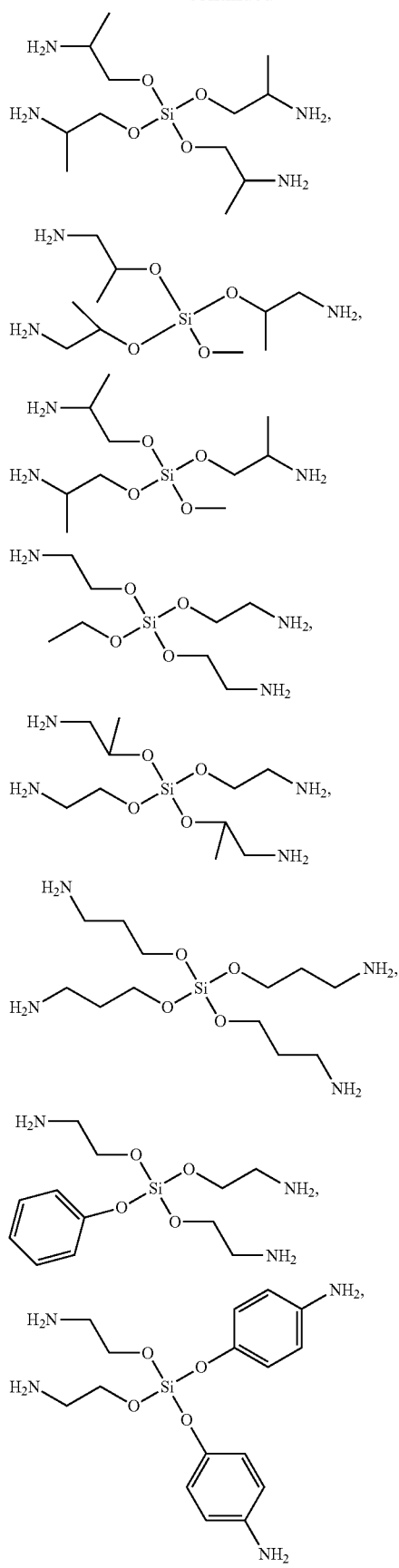
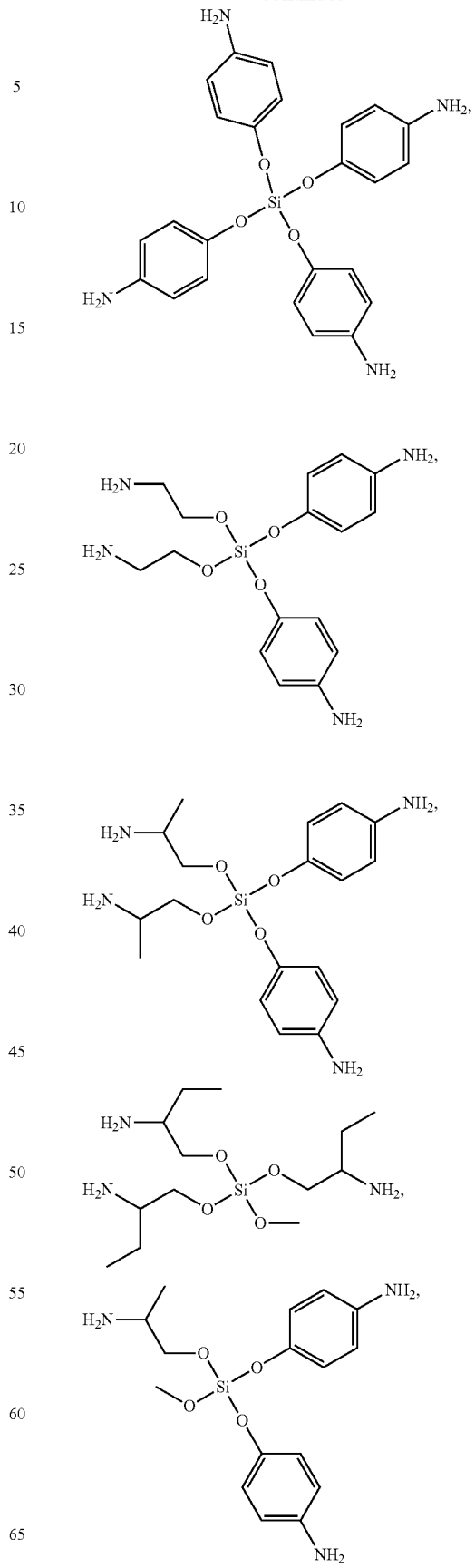

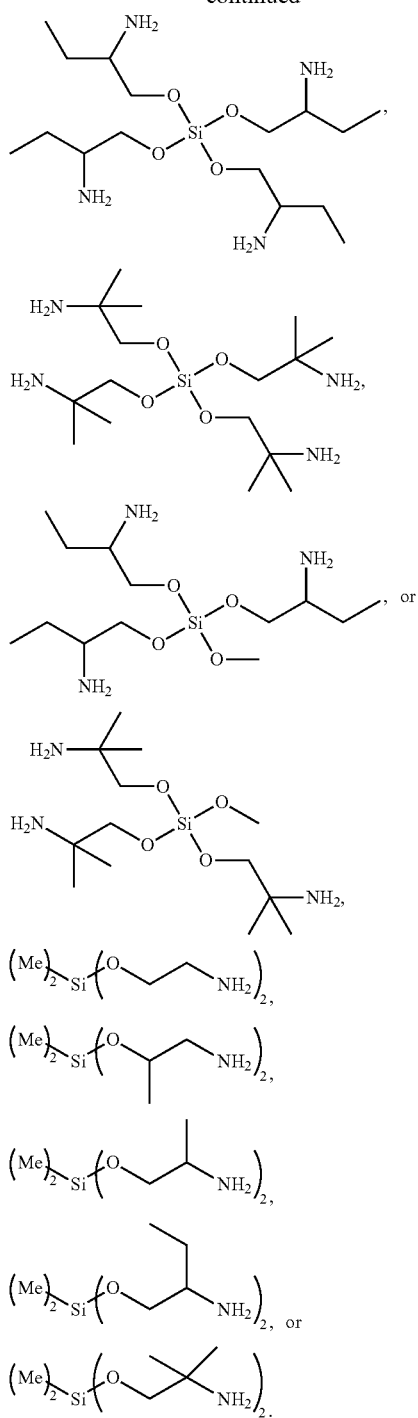
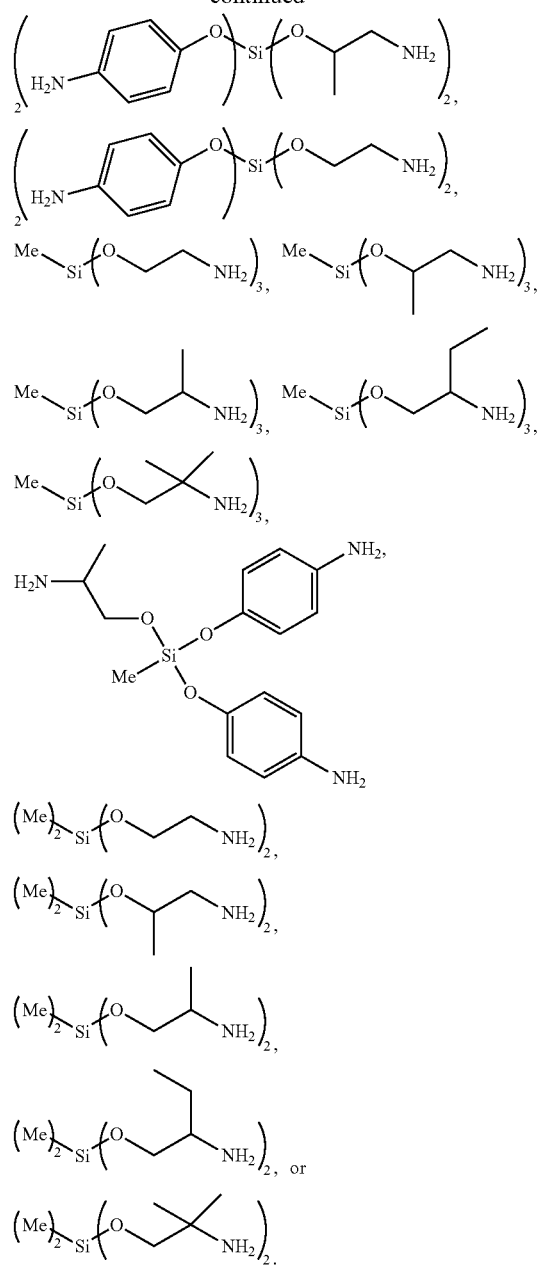
In some embodiments, the compound of Formula (I-A) is:
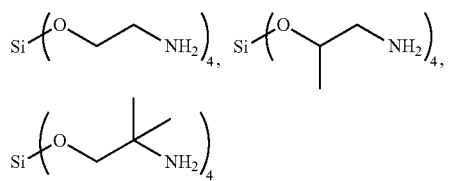
In some embodiments, the compound of Formula (I-A) is:
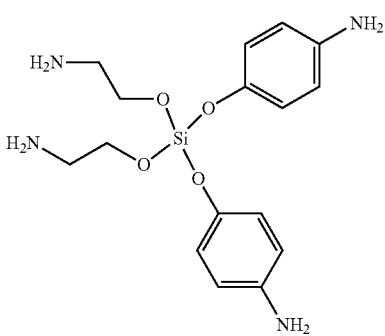
or -continued
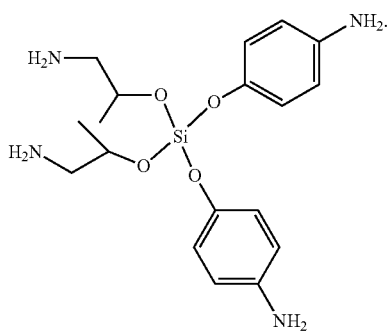
In some embodiments, the compound of Formula (I-A) is not:
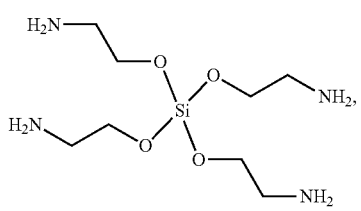
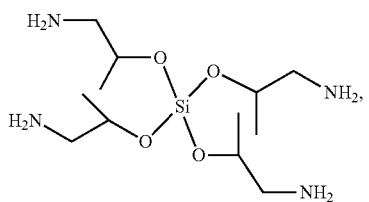
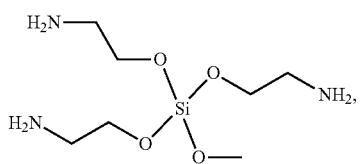
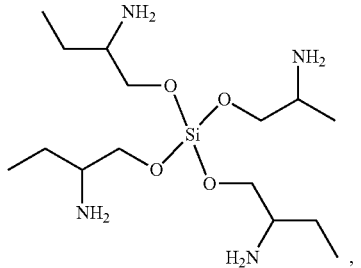
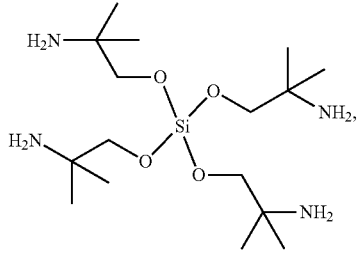
-continued
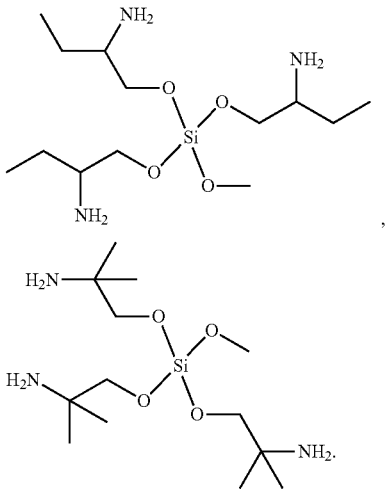
, or
In some embodiments, the compound of Formula (II-A-1) is:
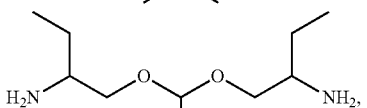
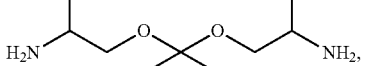
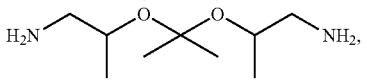
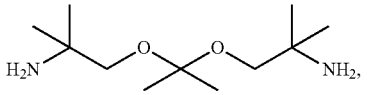
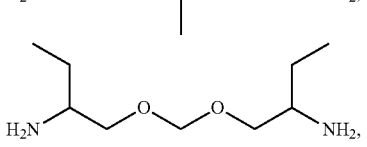
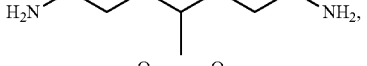
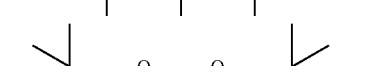
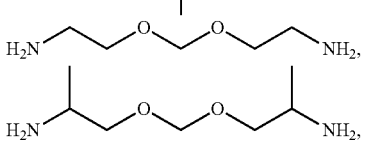

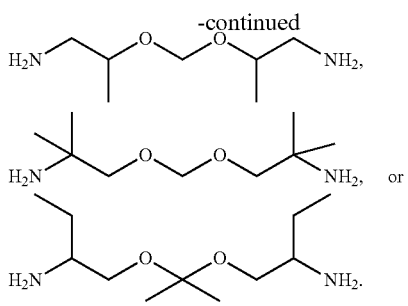

In some embodiments, the compound of Formula (II-A-1) is:

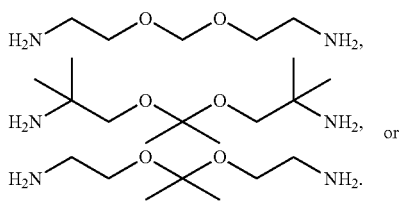

In some embodiments, the $T_g$ of the composition is from about 80° C. to 125° C. In some embodiments, the $T_g$ of the composition is greater than 82° C. In some embodiments, the $T_g$ of the composition is greater than 85° C. In some embodiments, the $T_g$ of the composition is greater than 90° C. In some embodiments, the $T_g$ of the composition is greater than 100° C. In some embodiments, the $T_g$ of the composition is greater than 120° C. In some embodiments, the tensile strength of the composition is from about 5,000 psi to about 7,500 psi. In some embodiments, the tensile strength of the composition is greater than 5,500 psi. In some embodiments, the tensile strength of the composition is greater than 7,000 psi.

In some embodiments, the composition comprises a chain extender. In some embodiments, the chain extender is a primary monoamine or secondary diamine compound. In some embodiments, the chain extender is monoethanolamine, diethanolamine, 3-aminopropanol, 2-aminopropanol, 1-amino-2-propanol, 2-aminobutanol, 2-amino-2-methyl-1-propanol, 2-amino-1-butanol, piperazine, benzylamine, aniline, p-anisidine, aminophenol, butylamine, and N,N'-dimethylethylenediamine, tert-butylamine, sec-butylamine, or a combination thereof.

In some embodiments, the chain extender is:

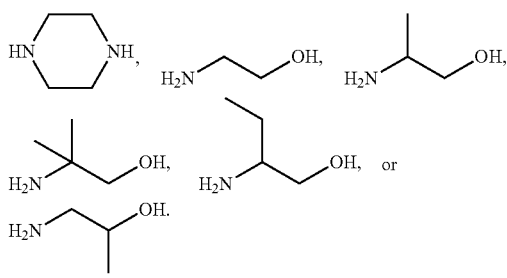

In some embodiments, the compound of Formula (II-A) is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %. In some embodiments, the compound of Formula (I-A) is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %. In some embodiments, the chain extender is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %.

In some embodiments, the epoxy resin is selected from a group consisting of glycidyl ether epoxy resin, glycidyl ester epoxy resin, glycidyl amine epoxy resin, alicyclic epoxy resin, aliphatic epoxy resin, phenolic epoxy resin, brominated epoxy resin and combinations thereof.

In some embodiments, the epoxy resin is a diepoxide resin.

In some embodiments, the epoxy resin comprises a blend of a first bisphenol-based epoxy resin having an epoxide equivalent weight (EEW) in the range of 160 to 220.

In some embodiments, the EEW is 188.

In some embodiments, the epoxy resin comprises a second bisphenol-based epoxy resin having an EEW in the range of 400 to 1500.

In some embodiments, the composition further comprises an auxiliary material selected from the group consisting of flame retardant, accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive, and combinations thereof.

In some embodiments, the composition further comprises a reinforcement material selected from a fibrous material or a non-fibrous material. In some embodiments, the composition further comprises a reinforcement material selected from glass fiber, carbon fiber, natural fiber, or chemical fiber. In some embodiments, the composition further comprises a reinforcement material selected from non-fibrous material.

In some embodiments, the reinforcement material is carbon nanotube, carbon black, metal nanoparticle, organic nanoparticle, iron oxide, boron nitride, or a combination thereof.

In some embodiments, the glass transition temperature of the epoxy resin composition described herein is greater than 80° C. but less than 170° C.

In some embodiments, the tensile strength of the epoxy resin composition described herein is greater than 7,000 psi and the tensile modulus is greater than 300,000 psi.

In some embodiments, the flexural strength of the epoxy resin composition described herein is greater than 9,000 psi and the flexural modulus is greater than 300,000 psi.

In some embodiments, the composition further comprises a reinforcing agent. In some embodiments, the reinforcing agent comprises at least one reinforcing component selected from the group consisting of glass fibers, aramid fibers, graphite fibers, carbon fibers, natural fibers, and non-natural fibers.

In some embodiments, the reinforcing agent is woven. In some embodiments, the reinforcing agent is non-woven.

In an aspect, provided herein is a product formed from curing an epoxy resin and a polyamine curing agent comprising a compound of Formula (I-A) or (I-B):

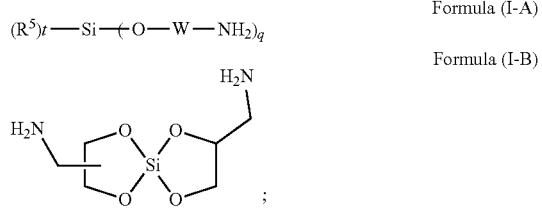

Formula (I-A)

Formula (I-B)

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each occurrence of $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the product is prepared by at least one method selected from a group consisting of wet lay-up, vacuum infusion, infusion, pultrusion, filament winding, and resin transfer molding, high pressure-resin transfer molding, prepreg, compression molding or other composite manufacturing methods.

In an aspect, provided herein is a method for recycling an epoxy resin composition described herein, comprising contacting the composition with an acid (e.g., in the presence of a solvent).

In some embodiments, the recycling step is performed in the presence of heat.

In some embodiments, the acid is selected from the group consisting of hydrochloric acid, acetic acid, chloroacetic acid, lactic acid, formic acid, propionic acid, citric acid, methane sulfonic acid, p-toluene sulfonic acid, sulfuric acid, benzoic acid, phthalic acid, and combinations thereof.

In some embodiments, the solvent is water. In some embodiments, the solvent is a mixture of water and a solvent selected from the group consisting of methanol, ethanol, ethylene glycol, propylene glycol, dimethylsulfoxide, isopropyl alcohol, butyl alcohol, pentanol, hexanol, heptanol, octanol alcohol, nonyl alcohol, dimethylformamide and combinations thereof.

In some embodiments, the acid has concentration in the solvent in a range from about 2% to 90% by weight. In some embodiments, the acid has concentration in the solvent in a range from about 5% to 25% by weight.

In some embodiments, the recycling step is carried out at a temperature ranging from about 15° C. to about 400° C. In some embodiments, the recycling step is carried out at a temperature ranging from about 80° C. to about 120° C.

In some embodiments, the heating is carried out for time ranging from about 1 hour to about 48 hours. In some embodiments, the heating is carried out for time ranging from about 1 hour to about 12 hours.

In some embodiments, the method further comprises a step of recovering a degradation product via a solvent evaporation process or a precipitation process.

In an aspect, provided herein is a degradation product resulting from the method for recycling a composite material as described herein.

In an aspect, provided herein is an adhesive composition comprising the epoxy composition as described herein.

In an aspect, provided herein is a method of removing (e.g., recovering, recycling) an adhesive composition (an adhesive composition as described herein), comprising providing to the composition with an acid and a solvent.

In an aspect, provided herein is a coating composition comprising the epoxy composition as described herein.

In an aspect, provided herein is a method of removing (e.g., recovering, recycling) a coating composition (an adhesive composition as described herein), comprising providing to the composition with an acid and a solvent.

In an aspect, provided herein is an encapsulating material comprising the epoxy composition as described herein.

In an aspect, provided herein is a method of removing (e.g., recovering, recycling) an encapsulating material (an adhesive composition as described herein), comprising providing to the composition with an acid and a solvent.

In an aspect, provided herein is a composite comprising a cross-linked polymer in contact with a substrate, wherein the cross-linked polymer comprises cleavable links derived from a cross-linking agent comprising a compound having Formula (I-A) or (I-B).

In an aspect, provided herein is a composite comprising a cross-linked polymer in contact with a substrate, wherein the cross-linked polymer further comprises cleavable links derived from a cross-linking agent comprising a compound having Formula (I-A) or (I-B).

In an aspect, provided herein is a method of recycling a cross-linked polymer, comprising:

(a) degrading the cross-linked polymer under an acidic condition into smaller, soluble molecules and/or polymers;
(b) and removing the degraded the cross-linked polymer, wherein the cross-linked polymer comprises cleavable links derived from a cross-linking agent comprising a compound having Formula (I-A) or (I-B).

In some embodiments, the cross-linked polymer further comprises cleavable links derived from a cross-linking agent comprising a compound having Formula (I-A) or (I-B).

In an aspect, provided herein is a compound of Formula (I-A) or (I-B):

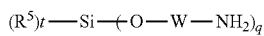

Formula (I-A)

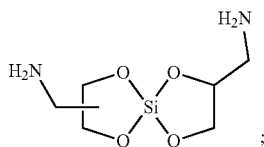

Formula (I-B)

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each occurrence of $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl. In some embodiments, the compound of Formula (I-A) is a compound of Formula (I-A-i) or (I-A-ii):

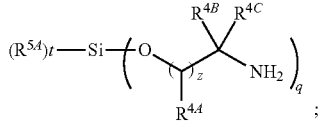

Formula (I-A-i)

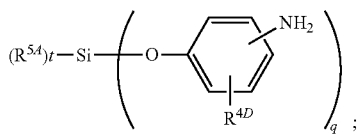

Formula (I-A-ii)

wherein: z is an integer from 1 to 6; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl (e.g., methyl, ethyl), cycloalkyl, aryl (e.g., phenyl, e.g., substituted phenyl), or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A) is a compound of Formula (I-A-iii):

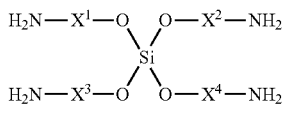

Formula (I-A-iii)

wherein: each of $X^1$, $X^2$, $X^3$, and $X^4$ is independently alkylene, cycloalkylene, heterocyclylene, alkenylene, alkynylene, cycloalkenylene, arylene, or heteroarylene.

In an aspect, described herein is a compound of Formula (I-A-iv)

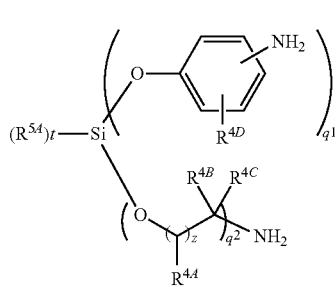

Formula (I-A-iv)

or a salt thereof, wherein: z is an integer from 1 to 6; t is an integer from 0 to 1; q1 is an integer from 1 to 4; q2 is an integer from 1 to 3; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4.

In some embodiments, the compound of Formula (I-A) is a compound of Formula (I-A-ii-1)

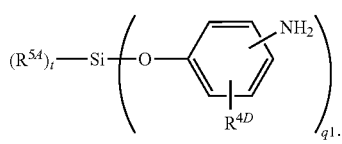

Formula (I-A-ii-1)

In some embodiments, q1 is 3, q2 is 0, and t is 1. In some embodiments, q1 is 4, q2 is 0, and t is 0. In some embodiments, q1 is 3, q2 is 1 and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, the compound is a compound of Formula (III-A) or (IV-A):

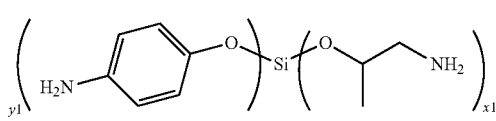

Formula (III-A)

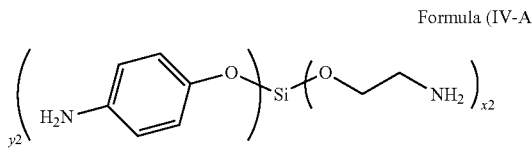

Formula (IV-A)

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound is:

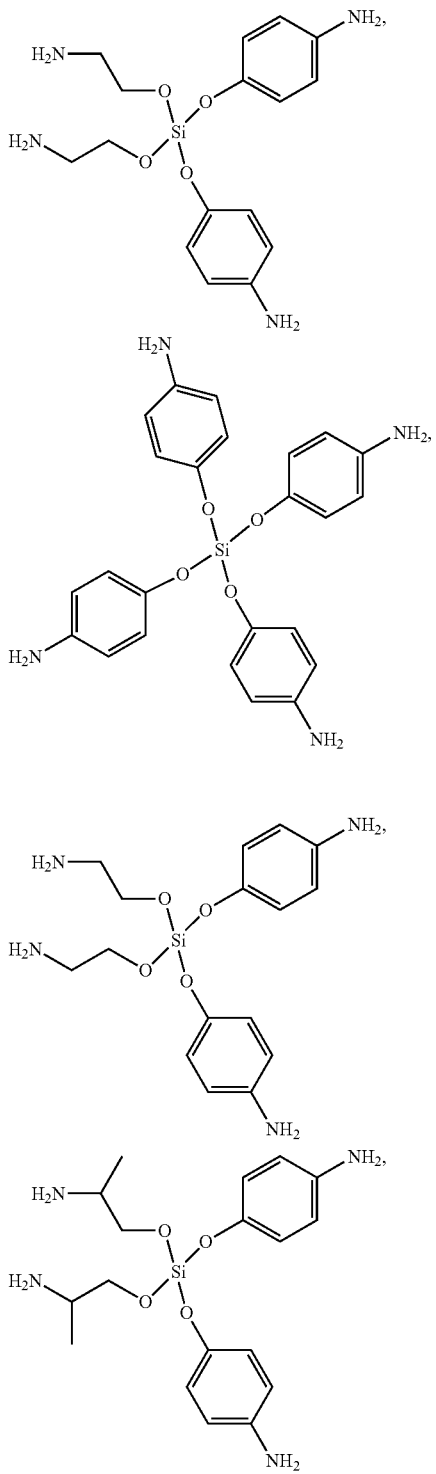

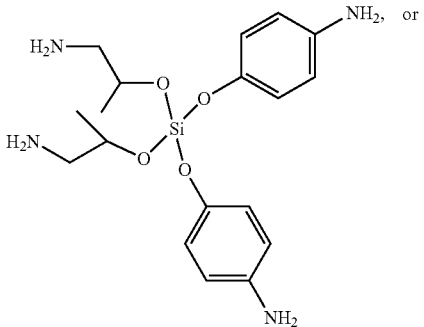

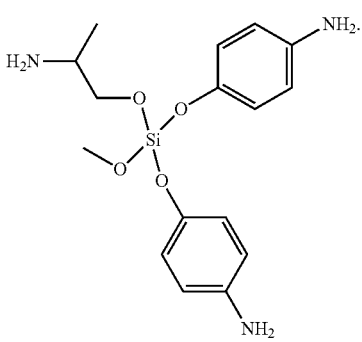

In some embodiments, the compound of Formula (I-A) is:

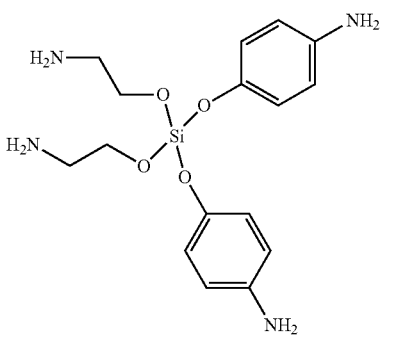

In an aspect, described herein is a compound having the structure:
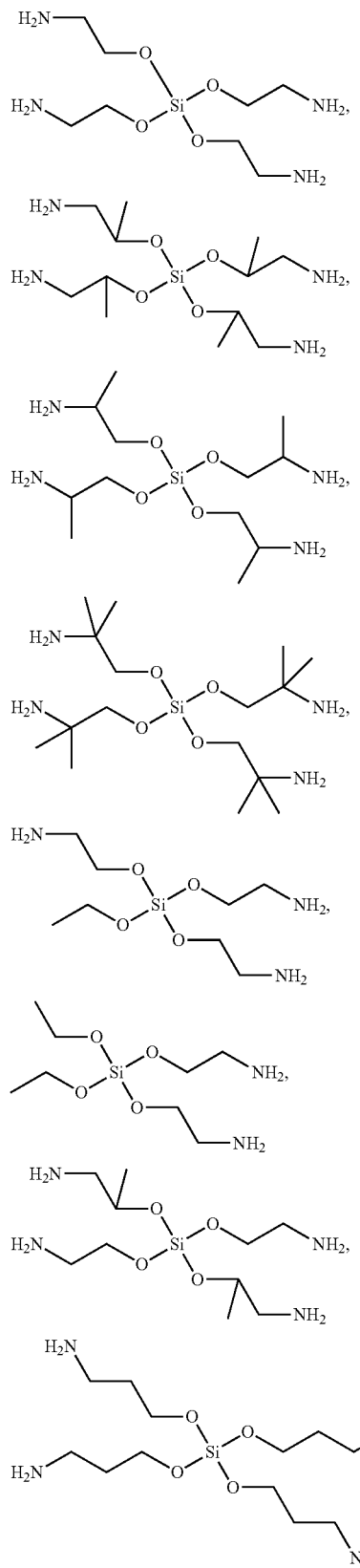
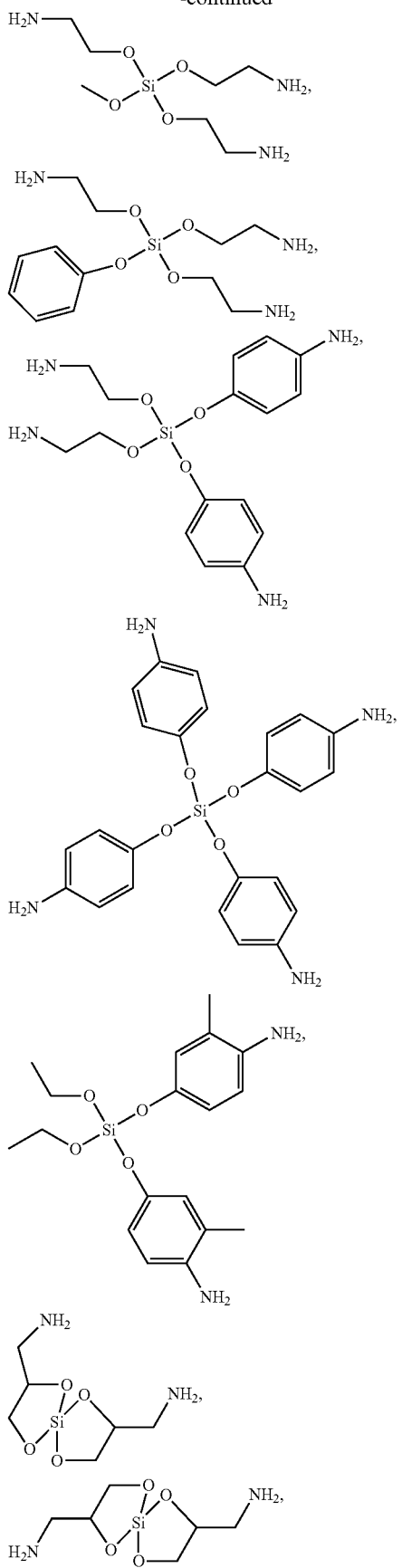

-continued

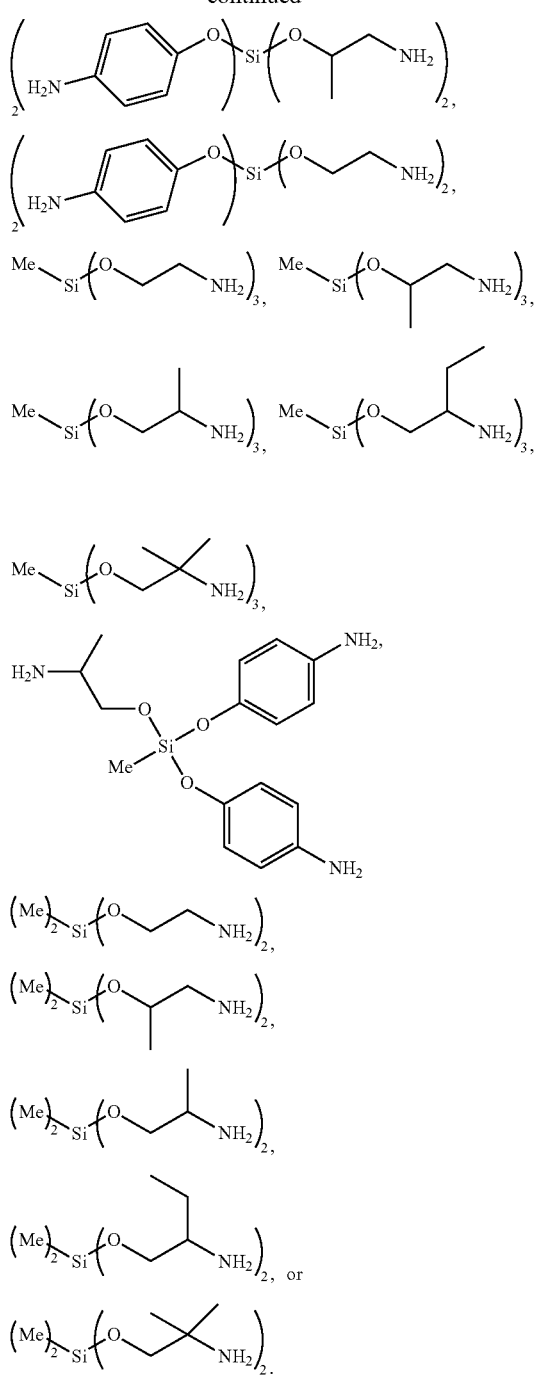

In some embodiments, the compound is

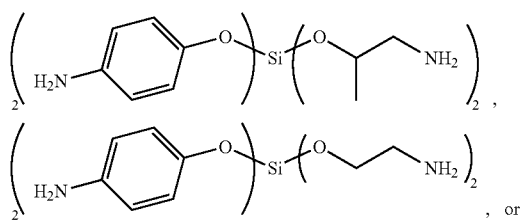

-continued

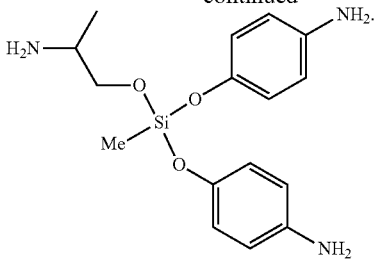

DETAILED DESCRIPTION

Figure 1:
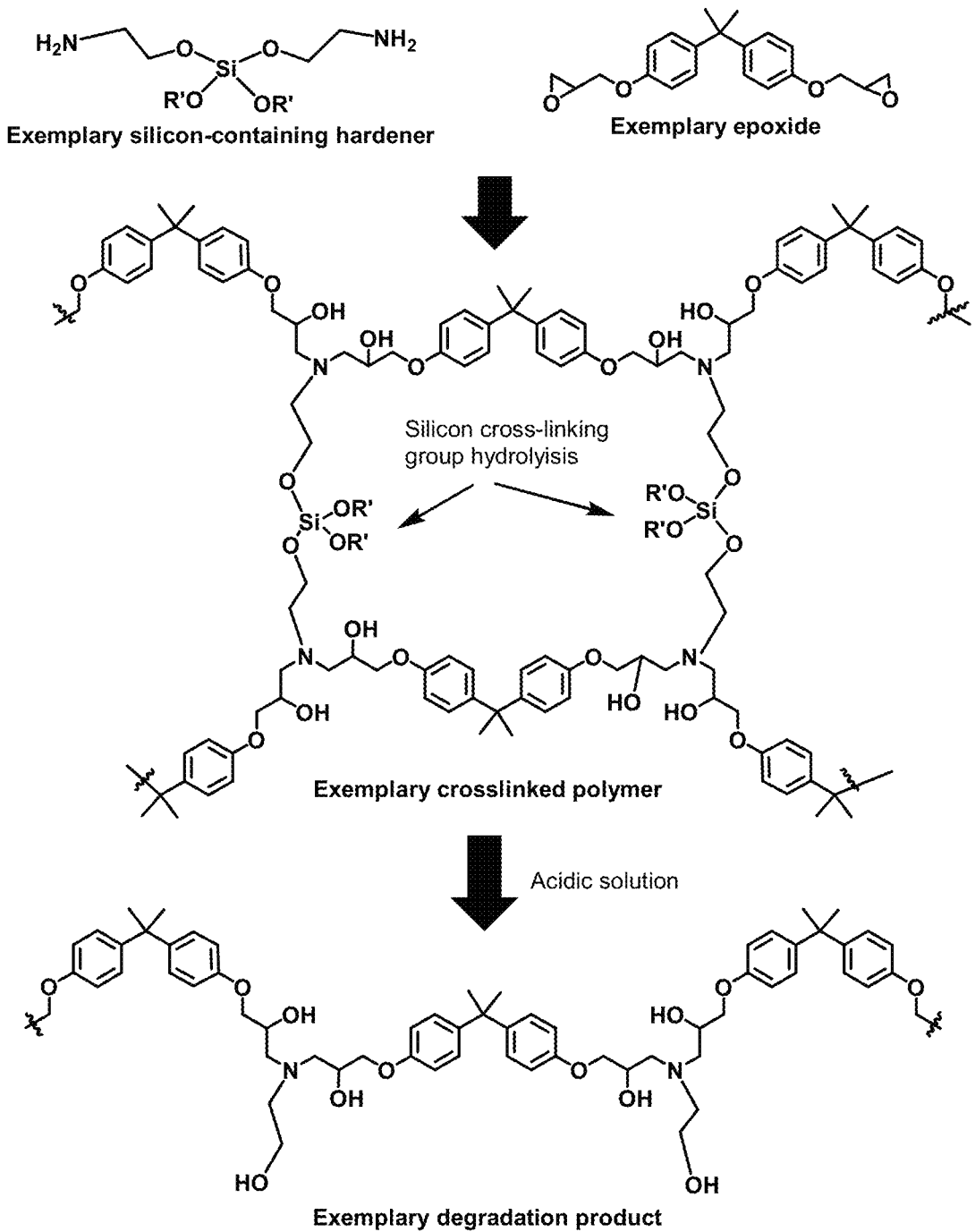
FIG. 1 depicts generic cross-linked epoxy product and generic epoxy degradation product.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

In an aspect, this invention describes silicon-containing compositions that, once cured, can be converted into its thermoplastic counterpart (i.e. non-cross-linked plastic) upon treatment with an acidic solution. Siloxy functionalities will enable the recycling of silicon-containing thermoset materials (e.g., products such as carbon fiber composites or glass fiber composites). This will enable OEMs to meet shifting regulatory end-of-life compliance, while also moving them toward "zero-landfill" operations via the possibility to recycle manufacturing waste. In an aspect, total composite recycling can be achieved of the silicon-containing compositions provided via specific, acid-based chemical recycling processes, whereby the fibers and thermoset can be separated, recovered, and reused. Additionally, the initial thermoset silicon-containing compositions may be recovered as a thermoplastic product. This degradation product could find use in plastic applications that rely, for example, on extrusion processes.

Silicon-Containing Polymer Compositions

Provided herein are silicon-containing polymer compositions comprising an acid-labile moiety (e.g., cured silicon-containing polymer compositions, cured and recyclable silicon-containing polymer compositions). The silicon-containing polymer compositions are formed from the curing of an epoxy resin (e.g., an epoxy resin as described herein) and a hardener or curing agent (e.g., a silicon-containing hardener or curing agent as described herein).

The silicon-containing polymer compositions can be used in a variety of applications, for example as composites, adhesives, and coating material.

The silicon-containing polymer compositions can disassemble under acid (e.g., mild acidic) conditions. The silicon-containing polymer compositions maintain mechanical and adhesive integrity at room temperature.

In an aspect, the silicon-containing polymer composition comprises a repeat unit (e.g., at least one repeat unit) of the Formula (III):

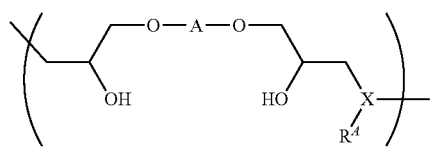

Formula (III)

wherein: A is an alkylene or arylene; and $XR^A$ is a curing agent (e.g., silicon-containing curing agent) as described herein. In some embodiments, the silicon-containing curing agent comprises a siloxy group.

In some embodiments, A is:

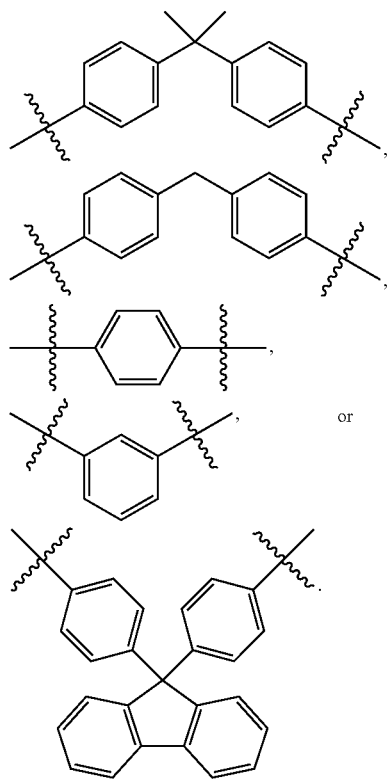

In some embodiments, the silicon-containing polymer composition additionally comprises at least one monomer of the Formula (III) wherein $XR^A$ is a hardener (e.g., a silicon-based hardener).

In some embodiments, the silicon-containing polymer composition additionally comprises at least one monomer of the Formula (III) wherein $XR^A$ is an acid degradable polyamine. In some embodiments, the acid degradable polyamine is selected from a compound having the Formula (II-A):

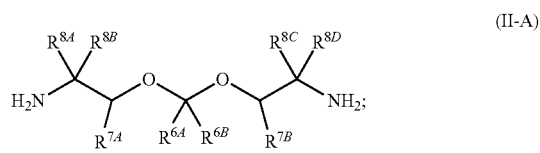

(II-A)

wherein: each of $R^{6A}$ and $R^{6B}$ is independently hydrogen or alkyl (e.g., methyl, ethyl, benzyl); and each of $R^{7A}$, $R^{7B}$, $R^{8A}$, $R^{8B}$, $R^{8C}$ and $R^{8D}$ is independently hydrogen or alkyl (e.g., methyl).

In some embodiments, the silicon-containing polymer composition additionally comprises a chain extender, wherein the chain extender is a primary monoamine or secdiamine compound. In some embodiments, the chain extender is selected from the group comprising monoethanolamine, diethanolamine, 3-aminopropanol, 2-aminopropanol, 2-aminobutanol, 1-amino-2-propanol, 2-amino-2-methyl-1-propanol, piperazine, benzylamine, aniline, p-anisidine, aminophenol, butylamine, and N,N'-dimethylethylenediamine, tert-butylamine, sec-butylamine, and combinations thereof.

In some embodiments, the silicon-containing polymer composition additionally comprises a combination of a hardener and a chain extender.

Compounds

Silicon-Containing Polyamine Curing Agents

Described herein are silicon-containing polyamine curing agents. In some embodiments, the polyamine curing agent comprises at least one silyl ether. In some embodiments, the polyamine curing agent comprises at least two silyl ethers. In some embodiments, the polyamine curing agent comprises 2, 3, or 4 silyl ethers. In some embodiments, the polyamine curing agent is a compound of Formula (I-A) or (I-B):

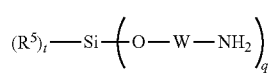

Formula (I-A)

Formula (I-B)

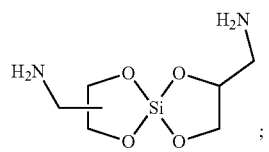

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each occurrence of $R^5$ is independently hydrogen, alkyl, cycloalkyl, heterocyclyl, alkenyl, alkynyl, cycloalkenyl, aryl, heteroaryl or $-OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, q is 3 or 4 and t is 1 or 0. In some embodiments, q is 3 and t is 1. In some embodiments, q is 4 and t is 0.

In some embodiments, the polyamine curing agent of Formula (I-A) is selected from a compound of Formula (I-A-i) or (I-A-ii):

Formula (I-A-i)

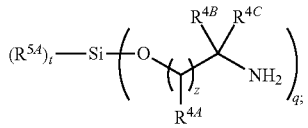

Formula (I-A-ii)

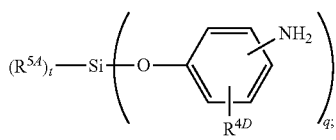

wherein: z is an integer from 1 to 6; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl (e.g., methyl, ethyl), cycloalkyl, aryl (e.g., phenyl, e.g., substituted phenyl), or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A) is a compound of Formula (I-A-iii):

Formula (I-A-iii)

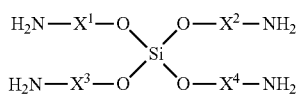

wherein: each of $X^1$, $X^2$, $X^3$, and $X^4$ is independently alkylene, cycloalkylene, heterocyclylene, alkenylene, alkynylene, cycloalkenylene, arylene, or heteroarylene.

In some embodiments, each of $X^1$, $X^2$, $X^3$, and $X^4$ is independently alkylene or arylene.

In some embodiments, each of $X^1$, $X^2$, $X^3$, and $X^4$ is independently unsubstituted or substituted $C_{1-3}$ alkylene. In some embodiments, each of $X^1$, $X^2$, $X^3$, and $X^4$ is independently unsubstituted $C_{1-3}$ alkylene.

In some embodiments, each of $X^1$, $X^2$, $X^3$, and $X^4$ is independently selected from an optionally substituted ethylene. In some embodiments, each of $X^1$, $X^2$, $X^3$, and $X^4$ is independently selected from ethylene, 1-methylethylene, 2-methylethylene, 1,1-dimethylethylene.

In some embodiments, each of $X^1$, $X^2$, $X^3$, and $X^4$ is independently selected from an optionally substituted propylene.

In some embodiments, each of $X^1$, $X^2$, $X^3$, and $X^4$ is independently selected from an optionally substituted arylene (e.g., 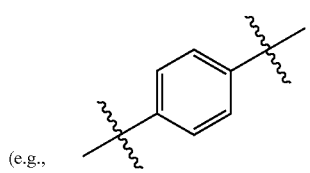, -continued

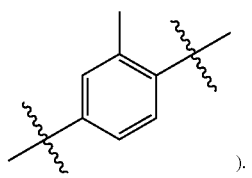

).

In some embodiments, the compound is a compound of Formula (III-A) or (IV-A):

Formula (III-A)

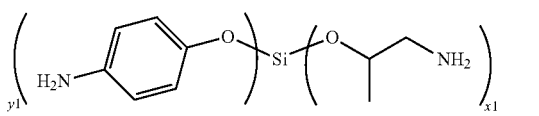

(Formula IV-A)

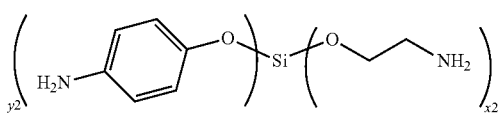

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments the compound of Formula (I-A) is:

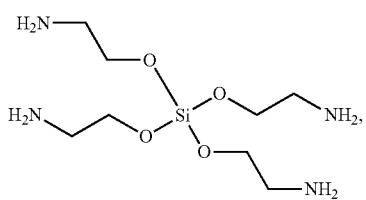

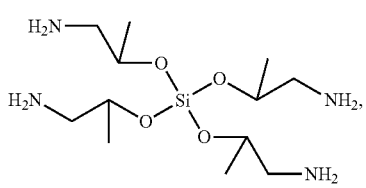

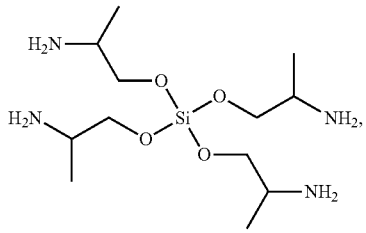

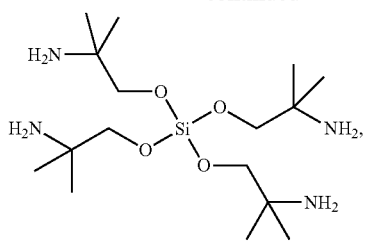
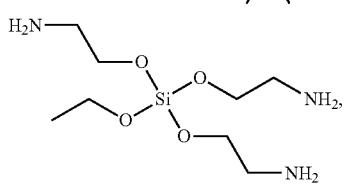
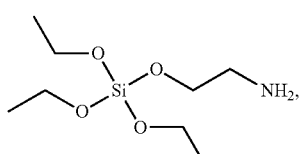
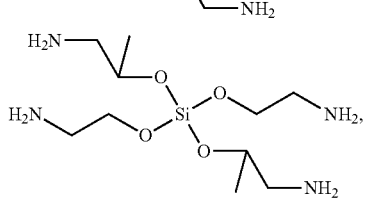
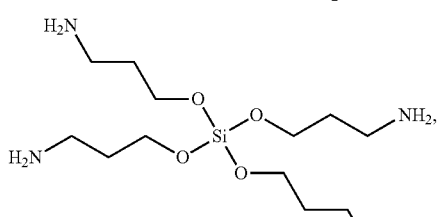
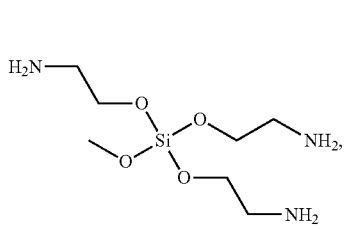
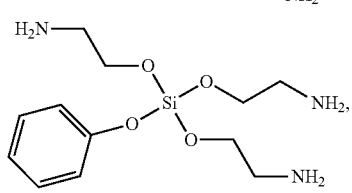
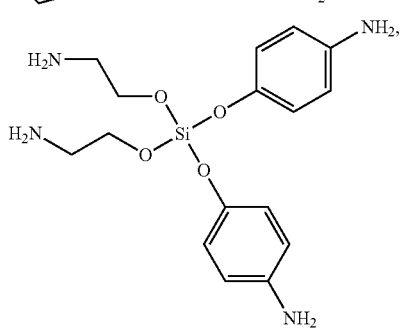
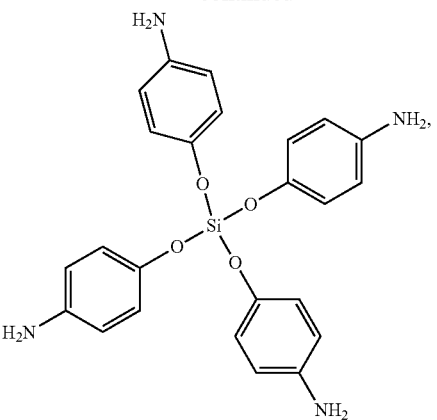
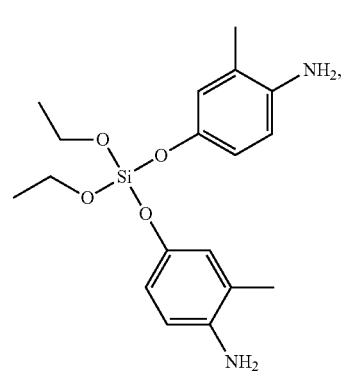
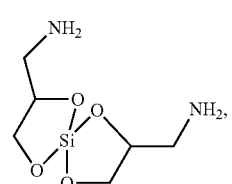
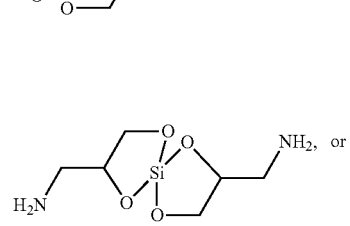
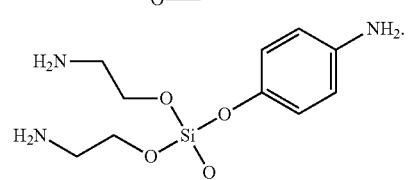
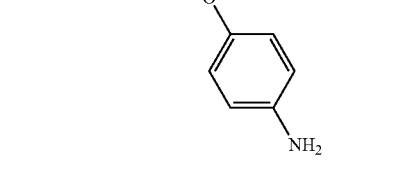

In an aspect, described herein is a compound of Formula (I-A-iv)

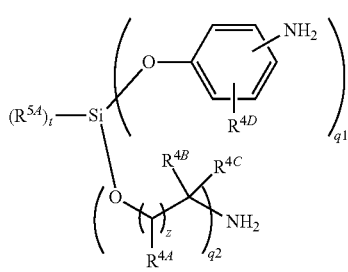

Formula (I-A-iv)

or a salt thereof, wherein: z is an integer from 1 to 6; t is an integer from 0 to 1; q1 is an integer from 1 to 4; q2 is an integer from 1 to 3; each of $R^{4A}$, $R^{4B}$, $R^{4C}$, and $R^{4D}$ is independently for each occurrence hydrogen or alkyl (e.g., methyl, ethyl); and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4, In some embodiments, the compound of Formula (I-A) is a compound of Formula (I-A-ii-1)

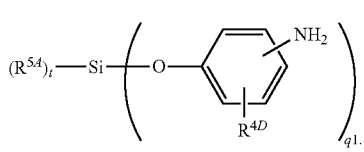

Formula (I-A-ii-1)

In some embodiments, q is 3, q2 is 0, and t is 1. In some embodiments, q1 is 4, q2 is 0, and t is 0. In some embodiments, q1 is 3, q2 is 1 and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, the compound is:

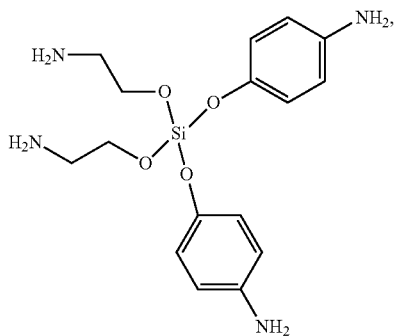

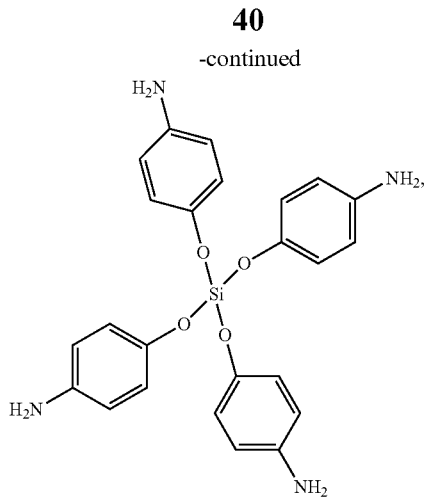

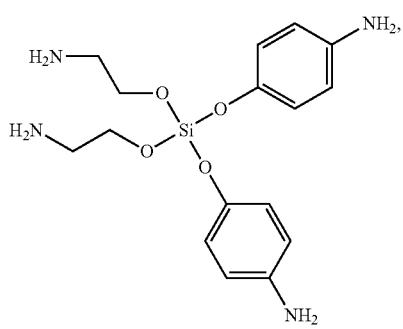

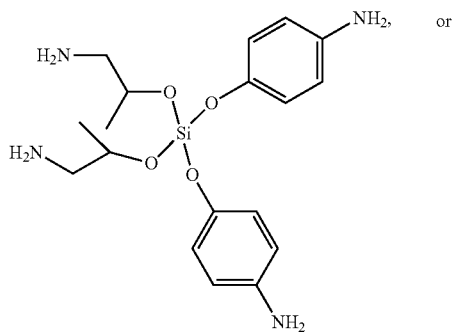

-continued
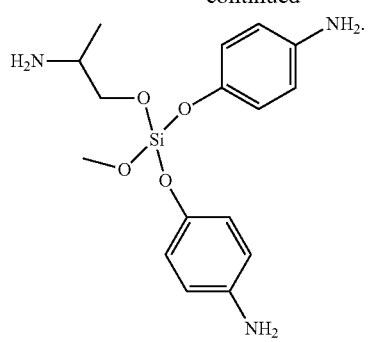
In some embodiments, the compound of Formula (I-A) is:
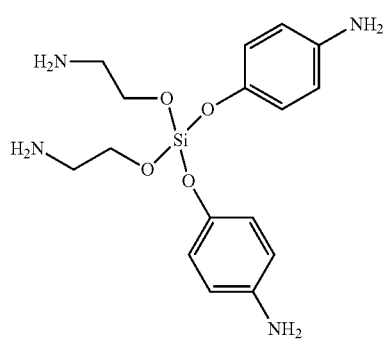
or
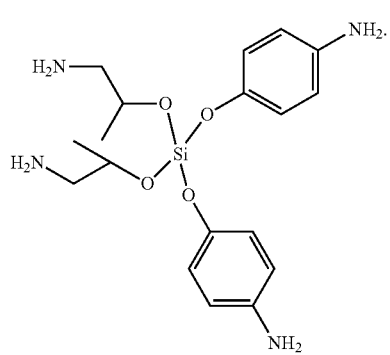
In an aspect, described herein is a compound having the structure:
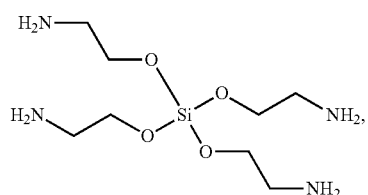
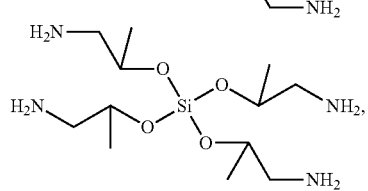
-continued
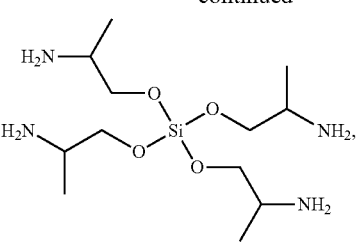
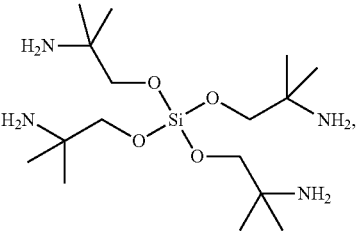
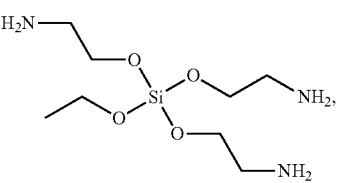
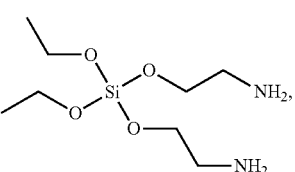
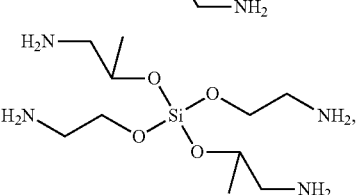
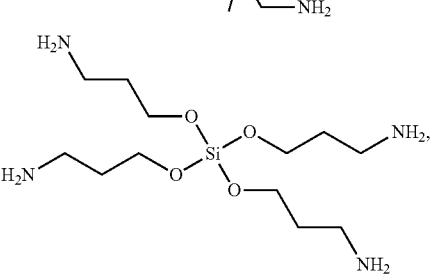
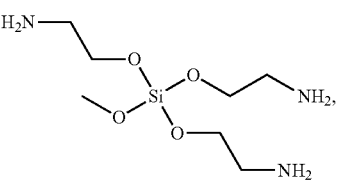
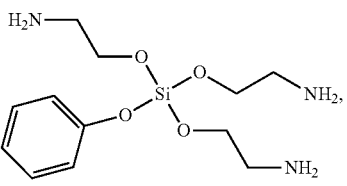

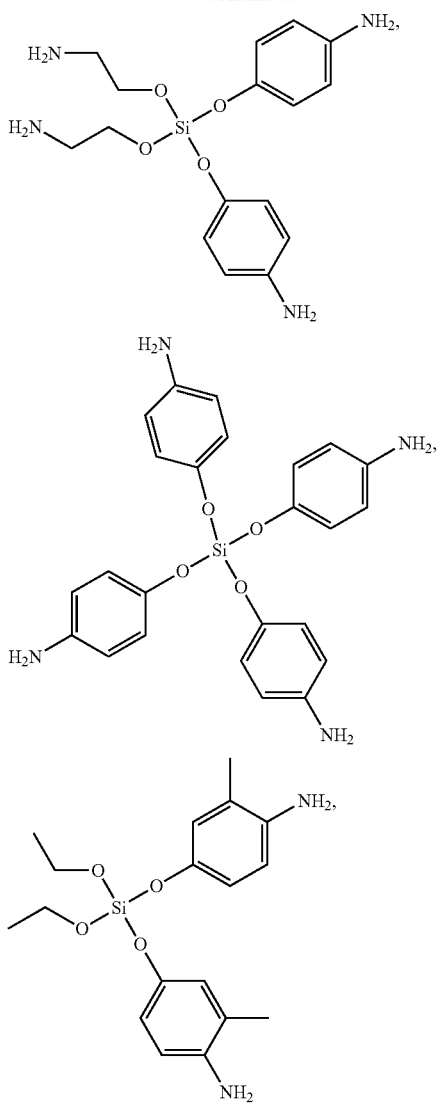
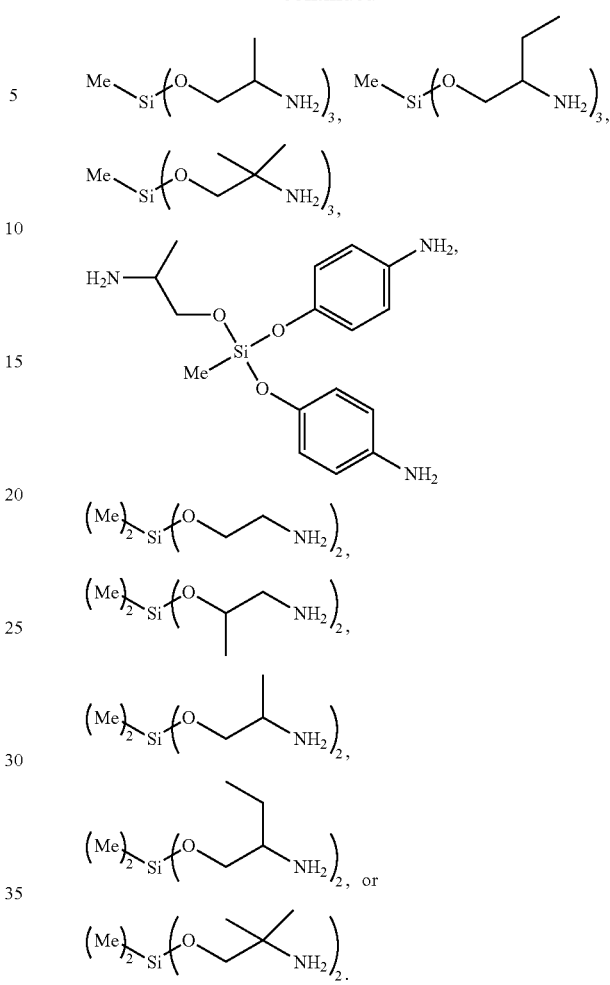
In some embodiments, the compound is
Other Curing Agents
In some embodiments, the polyamine curing agent is of a compound of Formula (II).

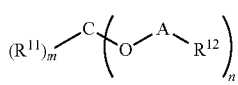
Formula (II)

wherein: m is 2, 1, or 0; n is 2, 3, or 4; the sum of m and n is 4; each occurrence of $R^{11}$ is independently hydrogen, alkyl, cycloalkyl, heterocycle, heterocycloalkyl, alkenyl, cycloalkenyl, aryl, heteroaryl, alkyloxyalkyl, or alkynyl; each A is independently alkyl, alkenene, alkylene-heteroalkylene, alkylene-heterocyclo-alkylene, alkylene, alkylene-oxy-alkylene, 1,4-alkyl substituted piperazine, carbonyl, thiocarbonyl, aryl, or heteroaryl; each occurrence of $R^{12}$ is independently —$NHR^3$, —SH, or heterocycloalkyl, wherein each $R^{13}$ is independently hydrogen, alkyl, aminoalkyl, alkylaminoalkyl, cycloalkyl, heterocycle, alkenyl, aryl, or heteroaryl; or, every two —O-A-$R^{12}$ groups, together with the carbon atom to which they are attached to, can independently form an dioxanyl ring with no less than 4 ring members and one or more of the ring carbon atom(s), other than the carbon atom to which the two —O-A-$R^1$2 groups are attached, are independently substituted with one or more independent amino group or aminoalkyl wherein each amino is independently a primary or secondary amino group.

In some embodiments, the polyamine curing agent of Formula (I) is a compound having the Formula (II-A-1):

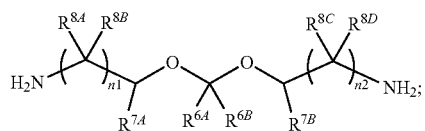

wherein: each of $R^{6A}$ and $R^{6B}$ is independently hydrogen or alkyl (e.g., methyl, ethyl, benzyl); each of $R^{7A}$, $R^{7B}$, $R^{8A}$, $R^{8B}$, $R^{8C}$ and $R^{8D}$ is independently for each occurrence hydrogen or alkyl (e.g., methyl or ethyl); and each of n1 and n2 is independently 1 or 2 (e.g., n1 and n2 are both 1).

In some embodiments, the polyamine curing agents of Formula (II) is a compound having the Formula (II-A):

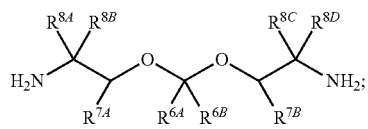

wherein: each of $R^{6A}$ and $R^{6B}$ is independently hydrogen or alkyl (e.g., methyl, ethyl, benzyl); and each of $R^{7A}$, $R^{7B}$, $R^{8A}$, $R^{8B}$, $R^{8C}$ and $R^{8D}$ is independently hydrogen or alkyl (e.g., methyl).

In some embodiments the compound of Formula (II) is:

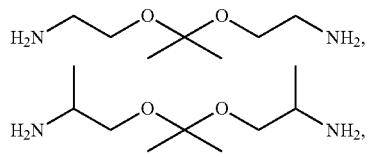

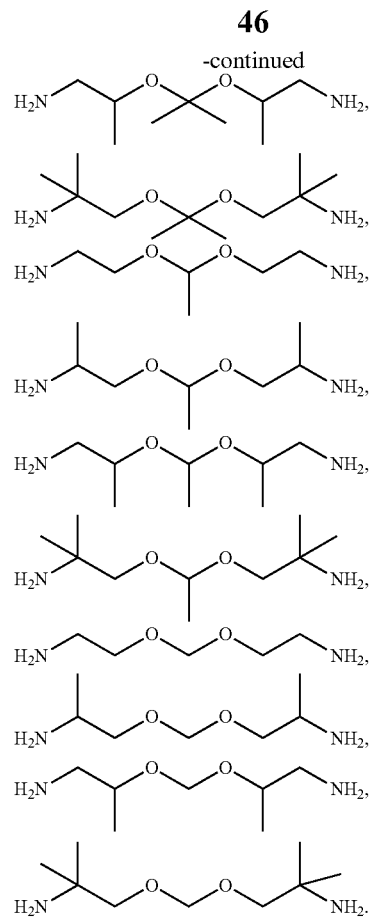

In some embodiments, the compound of Formula (II) is:

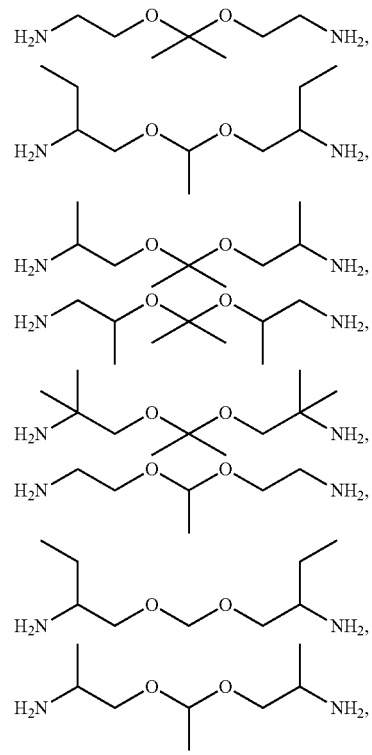

-continued

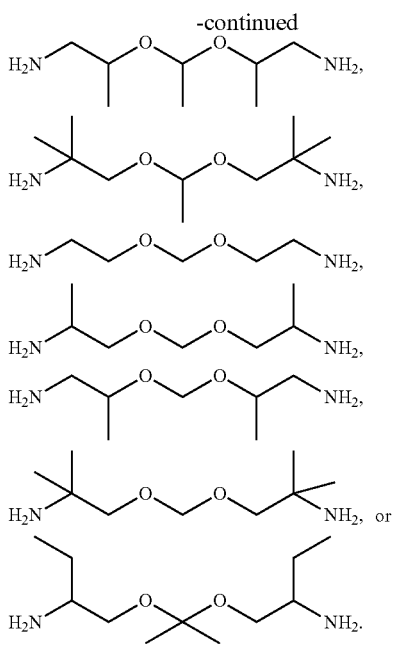

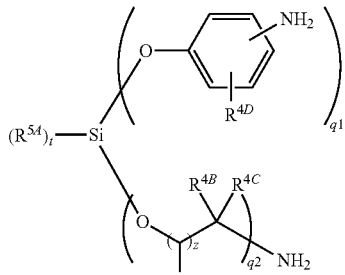

Formula (I-A-iv)

wherein: z is an integer from 1 to 6; t is an integer from 0 to 1; q1 is an integer from 1 to 4; q2 is an integer from 0 to 3; each of $R^{4A}$, $R^{4B}$, $R^{4C}$, and $R^{4D}$ is independently for each occurrence hydrogen or alkyl (e.g., methyl, ethyl); and each $R^{5A}$ is independently alkyl, cycloalkyl, aryl, or —OR, wherein $R^C$ is alkyl, cycloalkyl, heterocyclyl, alkenyl, alkynyl, cycloalkenyl, aryl or heteroaryl, provided that the sum of t, q, and q2 is 4.

In some embodiments, the compound of Formula (I-A) is a compound of Formula (I-A-ii-1)

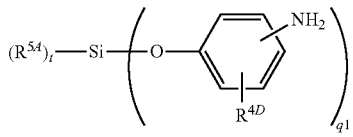

Formula (I-A-ii-1)

In some embodiments, q1 is 3, q2 is 0, and t is 1. In some embodiments, q1 is 4, q2 is 0, and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, the compound is a compound of Formula (III-A) or (IV-A):

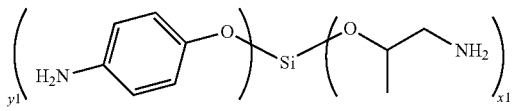

Formula (III-A)

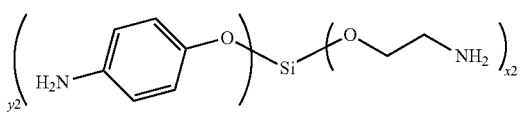

Formula (IV-A)

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some Other Chain Extenders In some embodiments, the silicon-containing composition described herein additionally comprises a chain extender, wherein the chain extender is a primary monoamine compound, or a secondary diamino compound. In some embodiments, the chain extender is selected from the group comprising monoethanolamine, diethanolamine, 3-aminopropanol, 2-aminopropanol, 2-aminobutanol, 1-amino-2-propanol, 2-amino-2-methyl-1-propanol, 2-amino-I-butanol, piperazine, benzylamine, aniline, p-anisidine, aminophenol, butylamine, and N,N'-dimethylethylenediamine, tert-butylamine, sec-butylamine, and combinations thereof. In some embodiments the chain extender is:

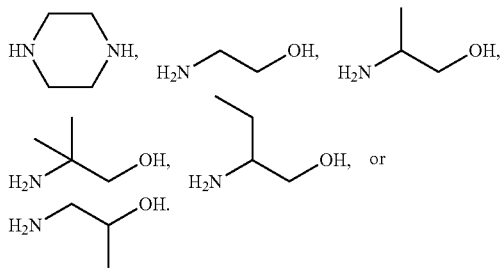

Compositions

The silicon-containing compositions provided herein result from reaction of an epoxy resin comprising an average of at least two epoxide groups per molecule. In some embodiments, the composition comprises an epoxy resin (e.g., an epoxy resin described herein) and a polyamino silicon compound herein (e.g., a compound of Formula (I-A)).

In one aspect, described herein is a composition comprising the reaction product of: an epoxy resin (e.g., an epoxy resin described herein); and a compound of Formula (I-A-iv):

embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound of Formula (I-A) is:

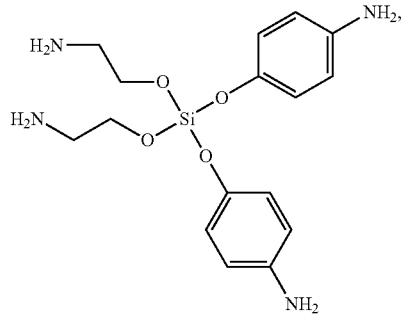

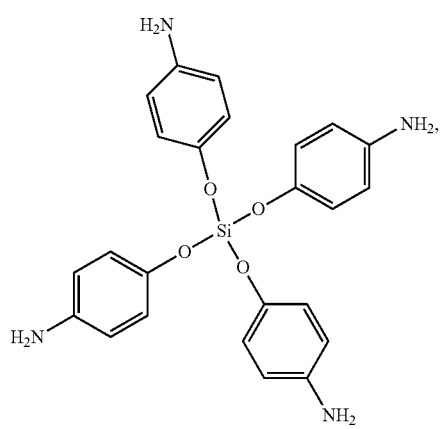

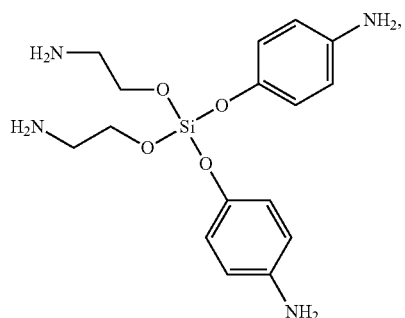

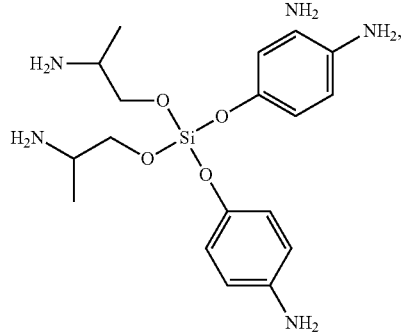

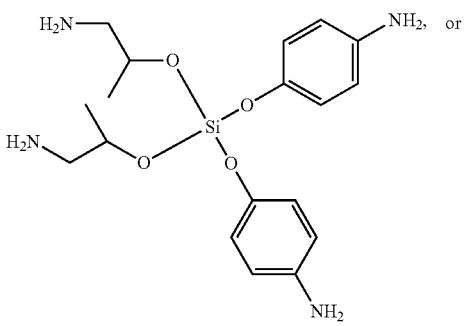

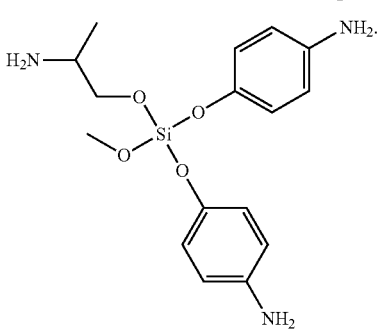 [SMILES: CO[Si](OCC(C)N)(Oc1ccc(N)cc1)Oc1ccc(N)cc1]

In some embodiments, the compound of Formula (I-A) is:

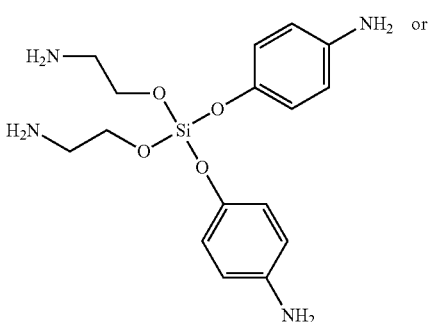

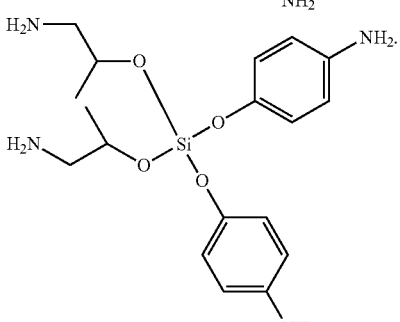

In some embodiments, the $T_g$ of the composition is from about 80° C. to 125° C. In some embodiments, the $T_g$ of the composition is greater than 82° C. In some embodiments, the $T_g$ of the composition is greater than 85° C. In some embodiments, the $T_g$ of the composition is greater than 90° C. In some embodiments, the $T_g$ of the composition is greater than 100° C. In some embodiments, the $T_g$ of the composition is greater than 120° C. In some embodiments, the tensile strength of the composition is from about 5,000 psi to about 7,500 psi. In some embodiments, the tensile strength of the composition is greater than 5,500 psi. In some embodiments, the tensile strength of the composition is greater than 7,000 psi.

In one aspect, described herein a composition comprising the reaction product of: an epoxy resin (e.g., an epoxy resin described herein); a compound of Formula (I-A);

Formula (I-A)

wherein: q is 4, 3, 2, or 1; t is 0, 1, 2, or 3; the sum of q and t is 4; each occurrence of W is independently alkylene, cycloalkylene, heterocyclylene, alkenylene, alkynylene, cycloalkenylene, arylene, or heteroarylene; and each $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl; and a compound having the Formula (II-A-1):

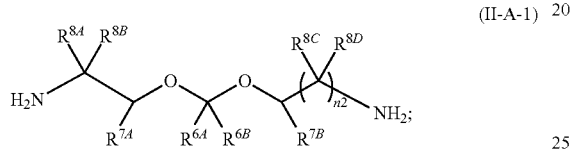

wherein: each of $R^{6A}$ and $R^{6B}$ is independently hydrogen or alkyl (e.g., methyl, ethyl, benzyl); each of $R^{7A}$, $R^{7B}$, $R^{8A}$, $R^{8B}$, $R^{8C}$ and $R^{8D}$ is independently for each occurrence hydrogen or alkyl (e.g., methyl or ethyl); and each of n1 and n2 is independently 1 or 2 (e.g. n1 and n2 are both 1).

In some embodiments, the compound of Formula (I-A) is a compound of Formula (I-A-iv)

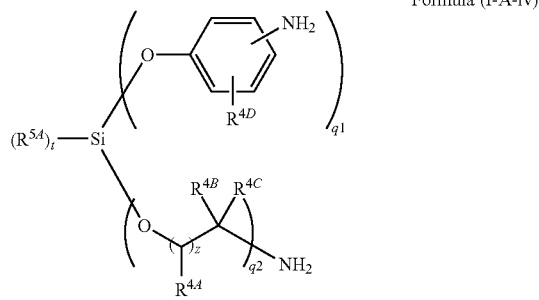

Formula (I-A-iv)

wherein: z is an integer from 1 to 6; t is an integer from 0 to 1; q1 is an integer from 0 to 4; q2 is an integer from 0 to 4; each of $R^{4A}$, $R^{4B}$, $R^{4C}$, and $R^{4D}$ is independently for each occurrence hydrogen or alkyl (e.g., methyl, ethyl); and each occurrence of $R^{8A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4.

In some embodiments, the compound of Formula (I-A) is a compound of Formula (I-A-i-1) or (I-A-ii-1):

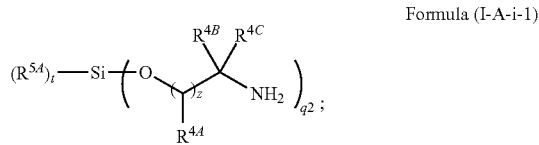

Formula (I-A-i-1)

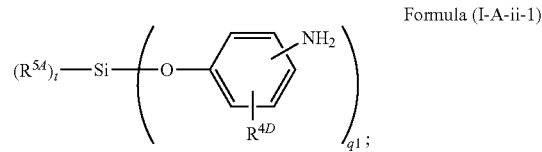

Formula (I-A-ii-1)

wherein: z is an integer from 1 to 6; each of $R^{4A}$, $R^{4B}$, $R^{4C}$, and $R^{4D}$ is independently for each occurrence hydrogen or alkyl (e.g., methyl, ethyl); and each $R^{5A}$ is independently alkyl (e.g., methyl, ethyl), cycloalkyl, aryl (e.g., phenyl, e.g., substituted phenyl), or —$OR^C$, wherein $R^C$ is alkyl (e.g., methyl, ethyl), cycloalkyl, heterocyclyl, alkenyl, alkynyl, cycloalkenyl, aryl (e.g., phenyl) or heteroaryl.

In some embodiments, the compound of Formula (I-A-iv-1) is a compound of Formula (I-A-i-1)

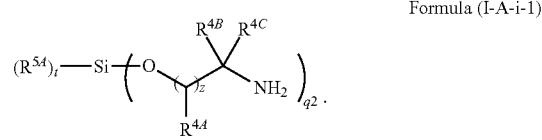

Formula (I-A-i-1)

In some embodiments, the compound of Formula (I-A-iv) is a compound of Formula (I-A-ii-1)

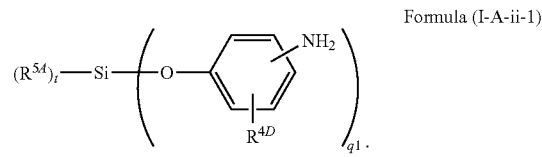

Formula (I-A-ii-1)

In some embodiments, the compound of Formula (I-A) is a compound of Formula (I-A-iii):

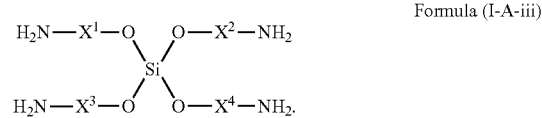

Formula (I-A-iii)

wherein: each of $X^1$, $X^2$, $X^3$, and $X^4$ is independently alkylene, cycloalkylene, heterocyclylene, alkenylene, alkynylene, cycloalkenylene, arylene, or heteroarylene.

In some embodiments, q is 2 and t is 2. In some embodiments, q is 3 and t is 1. In some embodiments, q1 is 3, q2 is 0, and t is 1. In some embodiments, q is 4, q2 is 0, and t is 0. In some embodiments, q1 is 2, q2 is 1, and t is 1. In some embodiments, q1 is 2, q2 is 2, and t is 0. In some embodiments, q1 is 1, q2 is 2, and t is 1. In some embodiments, $R^{4A}$ is hydrogen. In some embodiments, z is 1. In some embodiments, z is 2. In some embodiments, $R^{4A}$, $R^{4B}$, and $R^{4C}$ are hydrogen. In some embodiments, $R^{4A}$ is hydrogen and at least one of $R^{4B}$ and $R^{4C}$ is not hydrogen. In some embodiments, $R^{5A}$ is methyl (e.g., unsubstituted methyl) or ethyl (e.g., unsubstituted ethyl). In some embodiments, $R^{5A}$ is methyl (e.g., unsubstituted methyl). In some embodiments, $R^{5A}$ is ethyl (e.g., unsubstituted ethyl).

In some embodiments, at least one of $X^1$, $X^2$, $X^3$, and $X^4$ is arylene. In some embodiments, at least one of $X^1$, $X^2$, $X^3$, and X⁴ is phenylene optionally substituted with 1, 2, 3, or 4 occurrences of methyl (e.g., unsubstituted methyl). In some embodiments, X¹ and X³ is phenylene optionally substituted with 1 occurrence of methyl and X² and X⁴ is alkylene (e.g., unsubstituted $C_2$-$C_6$ alkylene, e.g., unsubstituted branched $C_2$-$C_6$ alkylene). In some embodiments, X¹ and X³ is unsubstituted phenylene and X² and X⁴ is alkylene (e.g., unsubstituted $C_2$-$C_6$ alkylene, e.g., unsubstituted branched $C_2$-$C_6$ alkylene).

In some embodiments, the compound is a compound of Formula (III-A) or (IV-A):

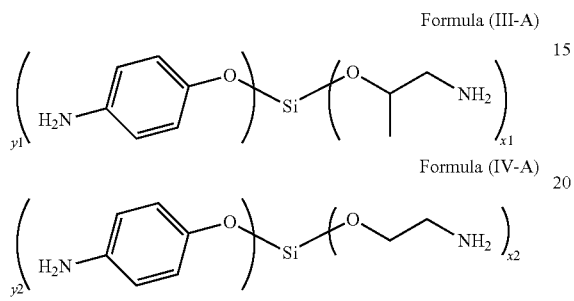

wherein each of x1, x2, y1, and y2 is independently 0, 1, 2, 3, or 4, provided that the sum of x1 and y1 is 4 and the sum of x2 and y2 is 4. In some embodiments, x1 and y1 are both 2. In some embodiments, x2 and y2 are both 2. In some embodiments, x1 is 1 and y1 is 3. In some embodiments, x2 is 1 and y2 is 3. In some embodiments, x1 is 0 and y1 is 4. In some embodiments, x2 is 0 and y2 is 4. In some embodiments, x1 is 3 and y1 is 1. In some embodiments, x2 is 3 and y2 is 1. In some embodiments, x1 is 4 and y1 is 0. In some embodiments, x2 is 4 and y2 is 0.

In some embodiments, the compound of Formula (I-A) is:

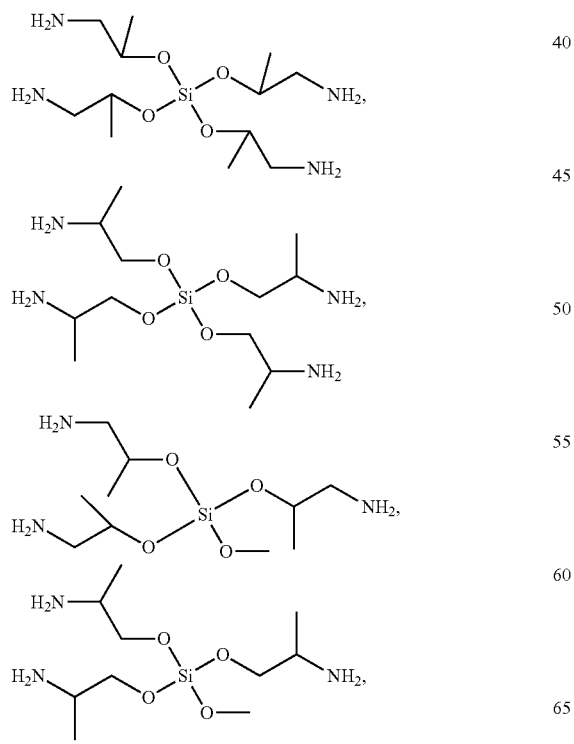

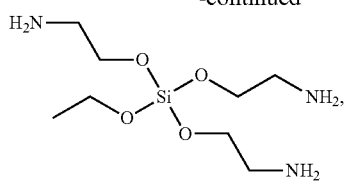

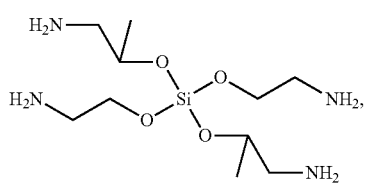

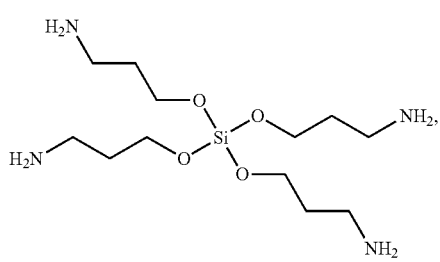

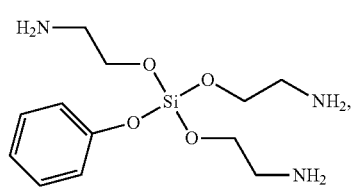

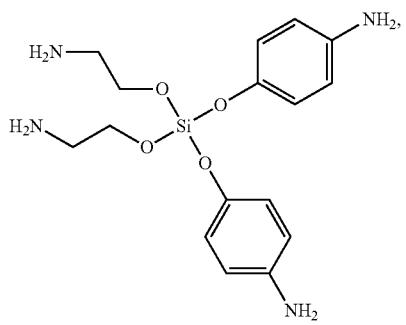

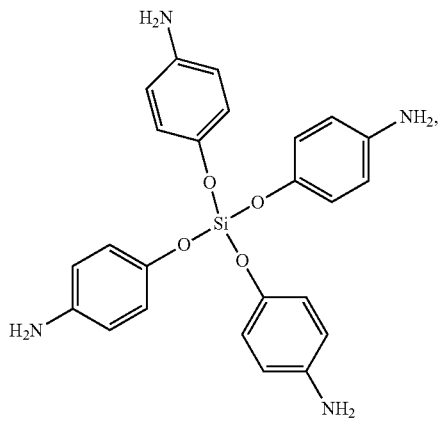

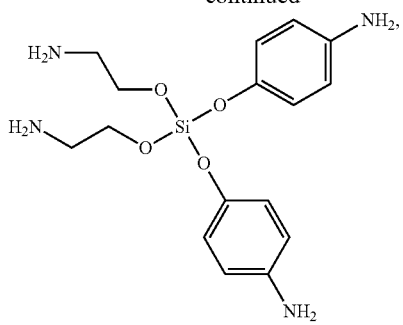
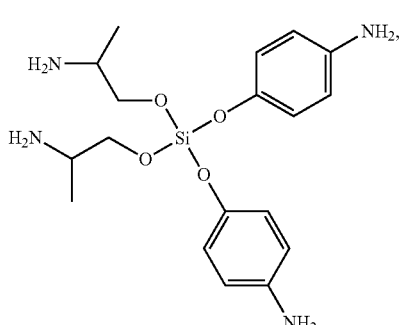
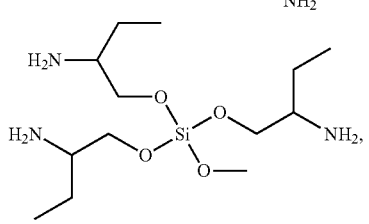
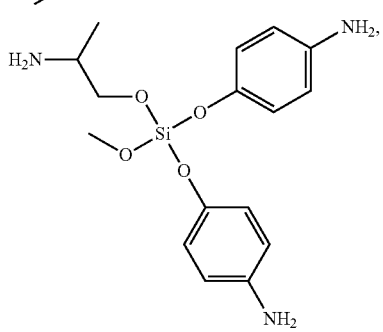
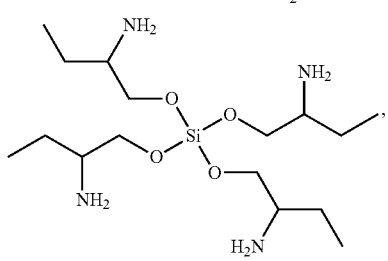
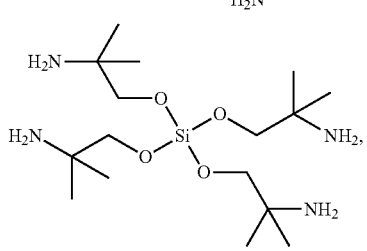
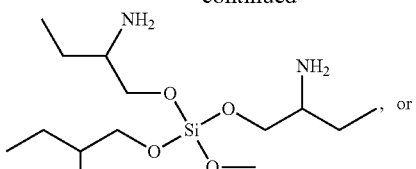
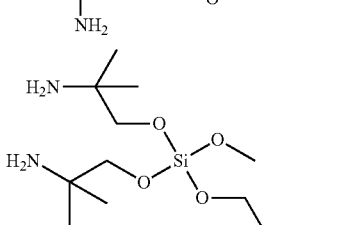
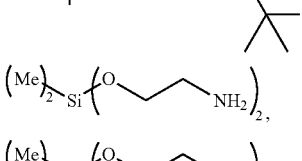
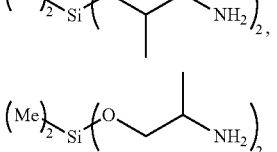
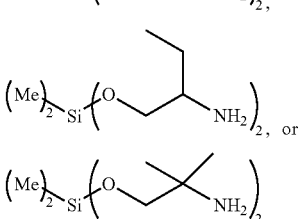
In some embodiments, the compound of Formula (I-A) is:
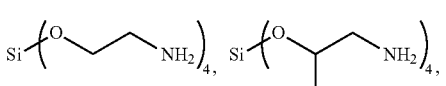
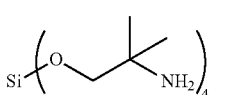
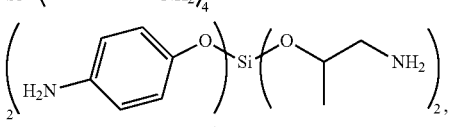
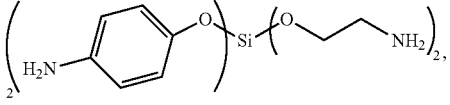
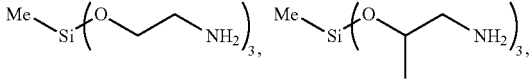
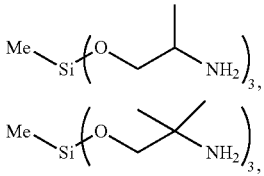

-continued
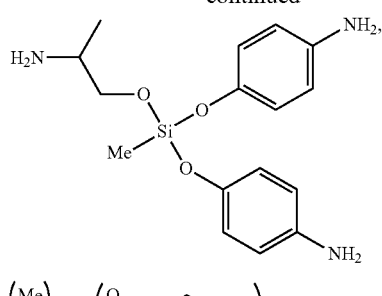
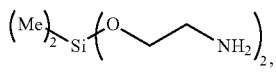
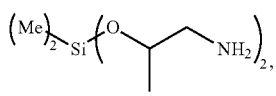
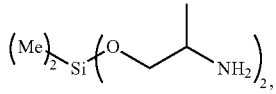
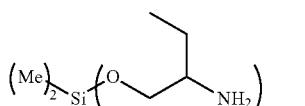
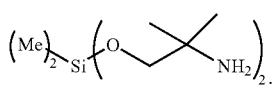
In some embodiments, the compound of Formula (I-A) is:
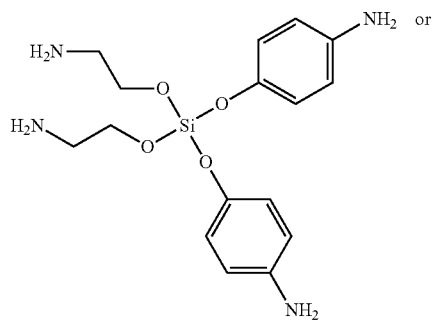
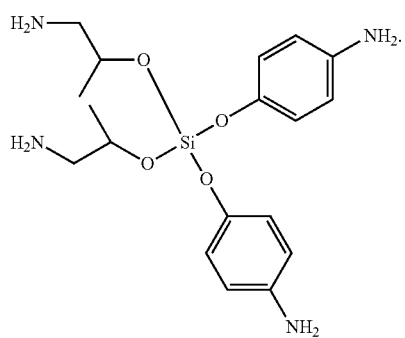
In some embodiments, the compound of Formula (I-A) is not:
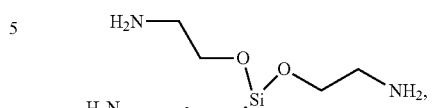
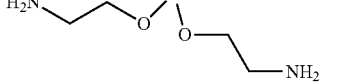
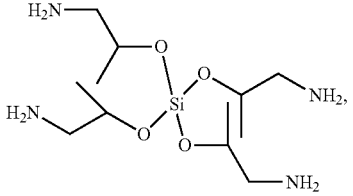
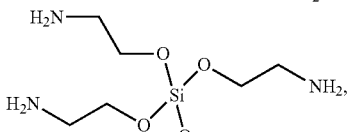
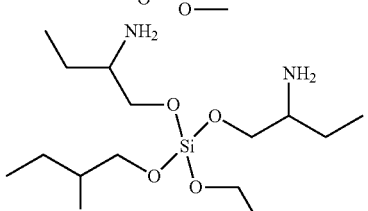
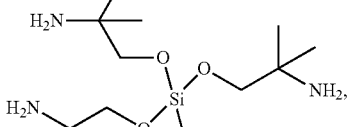
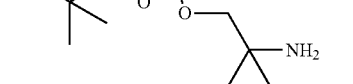
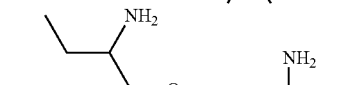
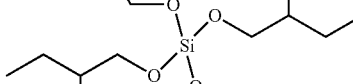
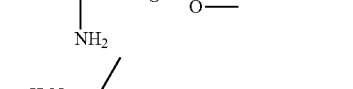
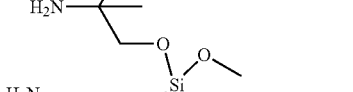
In some embodiments, the compound of Formula (II-A-1) is:

-continued

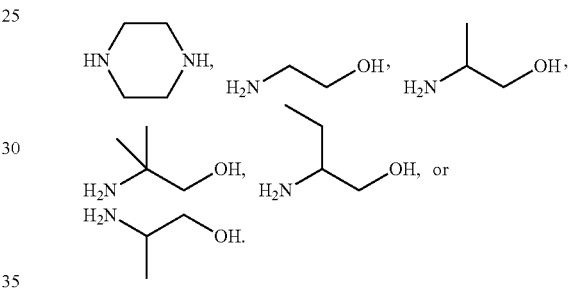

In some embodiments, the compound of Formula (II-A-1) is:

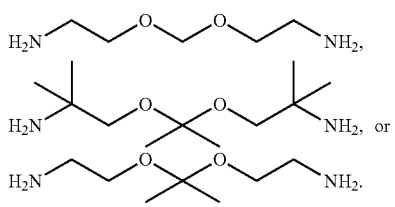

In some embodiments, the $T_g$ of the composition is from about 80° C. to 125° C. In some embodiments, the $T_g$ of the composition is greater than 82° C. In some embodiments, the $T_g$ of the composition is greater than 85° C. In some embodiments, the $T_g$ of the composition is greater than 90° C. In some embodiments, the $T_g$ of the composition is greater than 100° C. In some embodiments, the $T_g$ of the composition is greater than 120° C. In some embodiments, the tensile strength of the composition is from about 5,000 psi to about 7,500 psi. In some embodiments, the tensile strength of the composition is greater than 5,500 psi. In some embodiments, the tensile strength of the composition is greater than 7,000 psi.

In some embodiments, the composition comprises a chain extender. In some embodiments, the chain extender is a primary monoamine or secondary diamine compound. In some embodiments, the chain extender is monoethanolamine, diethanolamine, 3-aminopropanol, 2-aminopropanol, 1-amino-2-propanol, 2-amino-2-methyl-1-propanol, 2-amino-i-butanol, piperazine, benzylamine, aniline, p-anisidine, aminophenol, butylamine, and N,N'-dimethylethylenediamine, tert-butylamine, sec-butylamine, or a combination thereof.

In some embodiments, the chain extender is:

In some embodiments, the compound of Formula (II-A) is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %. In some embodiments, the compound of Formula (I-A) is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %. In some embodiments, the chain extender is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. %.

In some embodiments, the silicon-containing compositions provided herein includes an epoxy resin comprising a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin and combinations thereof. In some embodiments, the silicon-containing compositions provided includes an epoxy resin comprising a blend of a first bisphenol-based epoxy resin having an epoxide equivalent weight (EEW) in the range of 160 to 220. In some embodiments, the EEW is 188. In some embodiments, the silicon-containing compositions provided herein include an epoxy resin comprising a second bisphenol-based epoxy resin having an EEW in the range of 400 to 1500.

In some embodiments of the present invention, the silicon-containing compositions includes a blended epoxy resin. In one embodiment, epoxy resin blend includes a mixture of a diglycidyl ether of a bisphenol, especially bisphenol A, having an EEW of 150-195, typically 180-190, and a diglycidyl ether of a bisphenol, especially bisphenol A having an EEW of 400-1500, preferably 1200-1400. In one embodiment, epoxy resin blend includes a mixture of a diglycidyl ether of a bisphenol, especially bisphenol A, having an EEW of 150-195, typically 180-190, a diglycidyl ether of a bisphenol, especially bisphenol A, having an EEW of 400-1500, preferably 1200-1400, and an epoxy phenolic novalac resin with a functionality of 2.2 to 4, typically 3.6 or above, having an EEW of 170-190, preferably 174-180. In one embodiment, epoxy resin blend includes a mixture of a diglycidyl ether of a bisphenol, especially bisphenol A, having an EEW of 150-195, typically 176, a diglycidyl ether of a bisphenol, typically bisphenol A, having an EEW of 400-1500, preferably 1200-1400, and a tetra-functional epoxy having an EEW of 117-134.

Figure 2:
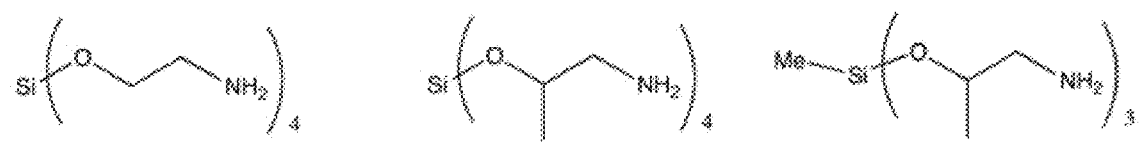
FIG. 2 depicts a comparison of polyaminosilane liquid surfaces after 1 hr exposure to ambient air.
Figure 2:

Various bisphenol-based epoxy resin blends may be used to make compositions of the present invention. In particular, in one embodiment the bisphenol-based epoxy resin is a blend based on the reaction products of epichlorohydrin and bisphenol A ("BPA") and/or bisphenol F ("BPF"). Bisphenol-based epoxy resins that are useful for the present invention include, but are not limited to, bisphenol A diglycidyl ether, ("BPADGE") and its oligomers and bisphenol F diglycidyl ether, ("BPFDGE") and its oligomers. FIG. 2 depicts various epoxy resins including generic structures for BPADGE and BPFDGE and their oligomers. In some embodiments, molecular weight of preferred oligomers of BPADGE and BPFDGE can be up to approximately 6000 g/mol. In one embodiment, the bisphenol-based epoxy resin based on bisphenol A has a molecular weight in the range of about 340 to about 6000 g/mol. In one embodiment, the bisphenol-based epoxy resin based on bisphenol F has a molecular weight in the range of about 310 to about 6000 g/mol. In some embodiments, the bisphenol-based epoxy resins have a molecular weight between and optionally including any two of the following values: 298, 300, 310, 340, 400, 600, 800, 1000, 1200, 1500, 1800, 2100, 2400, 2700, 3000, 3300, 3600, 3900, 4200, 4500, 4800, 5100, 5400, and 6000. Since the bisphenol-based epoxy resins have 2 epoxy groups per oligomer, the bisphenol-based epoxy resins have an epoxide equivalent weight (EEW) that is generally about half of the molecular weight of the oligomer. In one embodiment, the bisphenol-based epoxy resin is present from about 40 to about 95 wt %, based on the combined weight of the bisphenol-based epoxy resin, amine curing agent, and multi-epoxy reactive diluents. In another embodiment, the bisphenol-based epoxy resin is present from about 40 to about 95 wt %, based on the combined weight of the components in the curable composition. In some embodiments, the bisphenol-based epoxy resin is present in an amount between and optionally including any two of the following values: 40, 45, 50, 55, 60, 65, 70, 75, 80, 85, 90, and 95 wt %, based on the combined weight of the components in the curable composition. Specific, but non-limiting, examples of commercially available bisphenol A diglycidyl ether epoxy resins are Insulcast 503/504 BLK; Insulcast 504 Clear; Insulcast 125; Insulcast 333; Insulcast 136; and Insulcast 502, available (from ITW Polymer Technologies (Glenview, Ill., U.S.A.); Epon resins from Hexion Specialty Chemicals, Inc., now Momentive Specialty Chemicals, Inc., part of Momentive Performance Materials Holdings, Inc., (Columbus, Ohio, U.S.A.); D.$^{ERTM}$ resins from The DOW Chemical Company. Specific, but non-limiting, examples of commercially available include bisphenol F diglycidyl ether epoxy resins, including Araldite® GY285, Araldite® GY281, and Araldite® PY302-2 from Huntsman International, LLC (Salt Lake City, Utah, USA). Mixtures of bisphenol-based epoxy resins can be used in the curable composition described herein.

In some embodiments, reactive diluents are added to a bisphenol-based epoxy resin. In some embodiments, monofunctional epoxides are further blended with the bisphenol-based epoxy resin. Reactive diluents are common additives for influencing the viscosity of resin systems. Reactive diluents can also improve the surface qualities of coatings and composites. Specific, but non-limiting, examples of suitable reactive diluents include, $C_{12}$-$C_{14}$ alkyl glycidylethers, o-cresyl glycidylether, and butyl-glycidylether.

In some embodiments, the epoxy resin is DGEBPA or BPADGE:

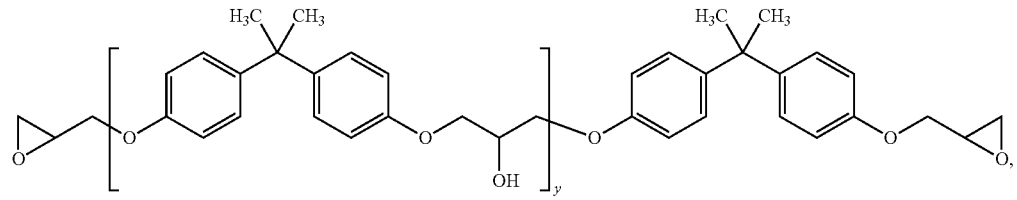

wherein y is an integer.

In some embodiments, the epoxy resin is DGEBPF or BPFDGE:

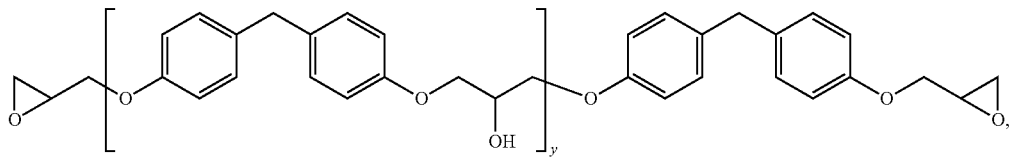

wherein y is an integer.

In some embodiments, the epoxy resin is a triepoxide resin. In some embodiments, the triepoxide resin is:

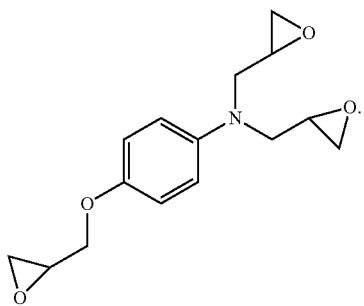 [SMILES: c1cc(N(CC2CO2)CC2CO2)ccc1OCC1CO1]

In some embodiments, the epoxy resin is a tetraepoxide resin. In some embodiments, the tetraepoxide resin is:

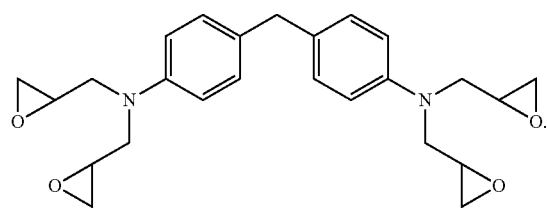 [SMILES: c1cc(N(CC2CO2)CC2CO2)ccc1Cc1ccc(N(CC2CO2)CC2CO2)cc1]

Epoxy curing involves at least two phenomena, polymerization and cross-linking. Each phenomenon is complex, and the two are often in competition during the overall curing process. Curing may be achieved by reacting epoxy with itself (e.g., homopolymerization) or with curing agents, e.g., curatives or hardeners. During the initial stage of curing, polymerization is typically favored as a result of the reactivity of curing agents (i.e., the reactive functional groups present in the curing agents). For example, where a curing agent has terminal primary amines or secondary amine groups, reactions of the primary amine groups with epoxy groups of the epoxy resin will be favored over reactions of the secondary amine groups (e.g., with epoxy groups). Therefore, generally polymerization of curing agents and epoxy resins precedes cross-linking reactions between them (e.g., reactions with the secondary amine groups). Such a polymerization reaction typically involves an addition reaction between an epoxide and an amine group, and thus would tend to follow a rate equation for addition polymerization. The molecular weight of the growing polymer increases (e.g., until the molecular weight approaches infinity), so that almost all monomers are connected by at least one bond and a polymeric network is formed. At this point, sometimes called the "gel point", the polymer possesses high molecular weight and few cross-links, and thus behaves much like a very high molecular weight thermoplastic (e.g., a plastic that is pliable or moldable above a specific temperature and returns to the solid state on cooling).

The second stage of the curing process, cross-linking, becomes the dominant phenomenon once the gel point is reached due to the lack of free monomers (i.e., monomer of the curing agent(s)). The cross-linking reaction involves interchain bonding of intrachain reactive sites, between either intrachain epoxides or secondary amine sites. Although cross-linking is a different phenomenon than polymerization, the rate of chemical conversion of the epoxide groups is unaffected (e.g., is similar or unchanged relative to the polymerization rate) in most epoxy systems. The cross-linking reactions produce a growing network and reduce the mobility of the chain segments. The growth of the network results in mechanical and thermal stabilization of the structure, resulting in increasing modulus and glass transition (Tg).

At a certain high degree of cross-linking, the increasing molecular weight of the structure exceeds the molecular weight which is thermodynamically stable as a rubber, and the material transforms into a glass, a process referred to as vitrification. In a glassy state, the mobility of reactants is severely restricted, reducing the rate of the reaction to a diffusion-controlled reaction, which is much slower. Further conversion is still possible, however, the rate is much slower since the process relies on diffusion rather than mobility to bring the reactants together. When the cross-linking reaction exhausts all the reactive sites available, the resulting structure is hard (i.e., has a high modulus) and insoluble due to a high degree of interchain bonding.

Since chemicals react in definite proportions, theoretically, a given weight of an epoxy resin will react with a given "equivalent," or "stoichiometric," amount of polyamine curing agent to form a polymeric product if the conditions are such that the reaction can proceed to completion. Therefore in general, with epoxies or epoxy resins, when the curing agent contains primary amine groups, as is the case with some embodiments of the cross-linking agents described herein (e.g., curing agents as described herein), the first step of the two stage curing process discussed above involves the oxirane ring in the epoxy resin undergoing a ring opening reaction with an amine group of the polyamine cross-linking agent to produce an aminoalcohol product. In the second step of the two-stage curing process the aminoalcohol product, a reacted amine nitrogen (i.e., as a "secondary" amine group), can react with yet another epoxy (i.e., oxirane ring) to form a higher molecular weight or branched polymer (e.g., to form a higher molecular weight and branched polymer). Thus, most or all of the —NH$_2$, or the primary amine groups of the polyamine cross-linking agent, will require two oxirane groups for complete reaction.

When the reactants are, for example, polyamine curing agent H-(1-1) and a typical bisphenol A-type epoxy resin, such as BPADGE, each molecule of polyamine curing agent H-(1-1), with its two primary amine groups, may react with four oxirane groups as shown in Scheme A below. Notably, epoxy resins such as BPADGE can, e.g., polymerize by homopolymerization and therefore not be present in the monomeric form depicted.

embodiments, an epoxy resin composition described herein includes an epoxy resin comprising a blend of a first bisphenol-based epoxy resin having an epoxide equivalent weight (EEW) in the range of 160 to 220 and a second bisphenol-based epoxy resin having an EEW in the range of 400 to 1500.

Analogously, amine hydrogen equivalent weight is defined by the following equation 2 (eq. 2):

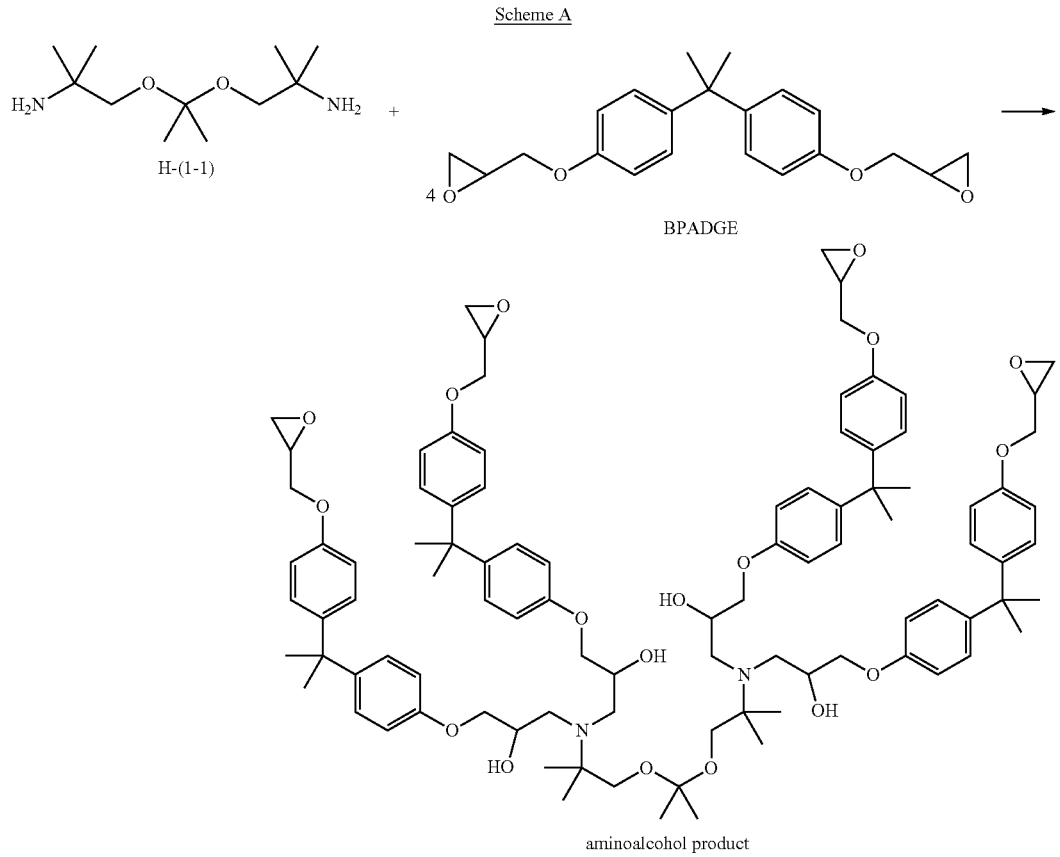

Scheme A

Therefore, in regard to chemical balancing, the optimum, proportions of reactants relative to epoxy systems can be obtained at least in of two ways: (1) by calculating the quantities involved from the chemical "equivalent" weights of all the reactants, or (2) by determining the balance empirically. Generally, epoxy resin's epoxide equivalent weight (EEW) is defined by the following equation 1 (eq. 1):

$$\text{Epoxy resin epoxide } eq. \text{ wt. (or } EEW) = \frac{(\text{MW of epoxy resin})}{(\text{no. of epoxides in the epoxy resin})} \qquad (eq. 1)$$

wherein MW of epoxy resin represents molecular weight of the epoxy resin.

In some embodiments, an epoxy resin composition described herein includes an epoxy resin comprising a blend of a bisphenol-based epoxy resin having an epoxide equivalent weight (EEW) in the range of 160 to 220. In some embodiments, an epoxy resin composition described herein includes an epoxy resin comprising a bisphenol-based epoxy resin having an EEW in the range of 400 to 1500. In some $$\text{Amine hydrogen } eq. \text{ wt. (or } AEW) = \frac{(\text{MW of amine})}{(\text{no. of active hydrogens})} \qquad (eq. 2)$$

wherein MW of amine represents molecular weight of the amine.

The stoichiometric ratio of an amine hardener to use with epoxy resin having a known or calculable epoxide equivalent weight EEW can be calculated using the following equation 3 (eq. 3):

$$\text{stoichiometric ratio of amine} = \frac{(\text{Amine } H \text{ } eq. \text{ wt} \times 100)}{(\text{Epoxide } eq. \text{ wt. of resin})} \qquad (eq. 3)$$

As an example, EEW of bisphenol A diglycidyl ether (BPADGE), AEW of H-(1-1), and stoichiometric ratio of H-(1-1) are calculated as follows.

H-(1-1) has a molecular weight of 218.34 atomic mass units (amu) and four active hydrogens. According to eq. 2, AEW of H-(1-1) equals 54.585 (or 218.34÷4). BPADGE has a molecular weight of 340.41 amu and two epoxides. According to eq. 1, EEW of BPADGE equals 170.205 (or 340.41÷2). According to eq. 3, the stoichiometric ratio of H-(1-1) to use with BPADGE equals 32.07 (or [54.585× 100]÷170.205). In other words, if one wishes to use a stoichiometric amount of H-(1-1) with BPADGE, one would need 32.07 parts H-(1-1) by wt. per 100 parts resin (BPADGE) or 32.07 g of H-(1-1) for every 100 g of BPADGE used.

Generally, the empirical (i.e., experimental, method of chemical balancing is preferred, e.g., at least because actual working conditions are used. However, in some embodiments, calculating the quantities involved from the chemical "equivalent" weights of all the reactants is used. Differences in the two calculating methods may arise from factors such as steric hindrance or catalytic effects. However, such differences may be easily corrected empirically through adjustments to the experimental conditions.

Examples of such epoxy applications include, but are not limited to, epoxy composites made via filament winding processes, epoxy composites made via filament winding type processes, epoxy composites made via pultrusion-type processes, epoxy composites made via prepreg-type processes, latent adhesive formulations, epoxy molding compounds and epoxy powder coatings. In some embodiments, the hardeners described herein include one or more cleavable links (e.g., a siloxy group, an acetal group or ketal group). Cleavable links such as a siloxy group, an acetal group or ketal group as described herein can provide ability to rework epoxy compositions.

As discussed above, epoxy resin curing involves polymerization and cross-linking. Generally, the polymerization of curing agents and epoxy resins precedes cross-linking reactions between them. During the polymerization step, the molecular weight of the growing polymer increases, so that almost all monomers are connected by at least one bond and a polymeric network is formed. The duration of time between initial mixing of the epoxy resin and the curing agent, and the mixture curing to an amorphous solid state is sometimes called the "gel time". The gel time of an epoxy composition at a given temperature is an essential parameter for applications that require the liquid state because after the mixed system hardens it is no longer pourable or otherwise useable.

As described herein, "working time" refers to the time it takes to for a 100 gram mass (or greater than a 100 gram mass) of epoxy resin composition to reach a solidified state at room temperature, wherein "room temperature" is defined by the temperature range of 22–27° C. "Gel-time," as described herein, is used interchangeably with "working time". Once the epoxy composition described herein reaches an amorphous solid state at room temperature, the epoxy composition is referred to as being in a "B-stage" state (i.e., it is not cross-linked), if that amorphous solids state is not a cross-linked state, and is still flowing or manipulable upon the application of greater temperature.

The silicon-containing compositions described herein should also find use in pipe repair applications (e.g., trenchless pipe repair applications). For example, the Cured in Place Pipe [CIPP] process involves inverting a resin saturated felt tube made of fiberglass and other materials inside a damaged pipe, and then curing the resin system, effectively making a pipe with in a pipe seal. Polyester thermosets, are commonly used for CIPP. For regulatory reasons, there is increasing momentum in the industry to switch a way from polyester resin systems, e.g., to epoxy-based systems. However, there has been a lack of suitable epoxy curatives that can be used for these purposes. The typical requirements of a resin systems are both that 1) the resin impregnated felt has to be easily pliable, e.g., for at last 24 hours after impregnation; and 2) the resin should cure in less than 24 hours (preferably less than 12 hours), e.g., at the temperature of the hot water passing through the pipe (usually <80° C.). Conventional epoxy curatives systems are not well suitable for either or both requirements.

For prepreg composite manufacturing, epoxy compositions must exhibit very slow cure rate at ambient temperature and/or cure to an intermediately stable state to be acceptable. This can be achieved with curing agents that cure the resin following a sequential course that entails, first, linear polymerization and subsequent cross-linking of the linear polymers. The cross-linking agents described herein are ideally suited for prepreg composite manufacturing. Certain epoxy resin compositions described herein provide long working time that keeps the epoxy resin composition flowing or manipulable for a long time and thus allows the epoxy composition to be shaped and processed over the long working time desired, e.g., for prepreg composite manufacturing. In some embodiments, the compositions are used for manufacturing prepreg composites.

Certain epoxy compositions described herein undergo (1) minimal reaction at ambient temperatures, but suitable reactivity at elevated temperatures; and (2) a slight linear polymerization which yields a glassy solid or metastable state, effectively slowing further linear polymerization or cross-linking, until reinitiated with introduction of energy, including heat at a higher temperature, to advance polymerization and cross-linking of the epoxy resin composition. One skilled in the art would recognize an epoxy composition in this netastable state as a "B-stage." One skilled in the art should also recognize that it is not typical for aliphatic polyamines curing agents to lead to B-staging epoxy resin compositions. As described herein, out-life or time in B-stage or B-state, are defined as the time to reach a partially cross-linked state (e.g., the time to reach a state wherein the epoxy composition is not capable of flowing, e.g., upon addition of elevated temperature; the time to reach a state wherein the epoxy composition is transformed to a partially or fully cross-linked polymer matrix).

In a typical prepreg process, an intermediate composite is formed, for example by coating a woven fiber (e.g. fiberglass, carbon fiber, aramid fiber, or natural fiber) with an epoxy resin and hardener mixture; and cured to an intermediate state. At the desired time, such prepreg sheets can be stacked and molded into a composite part by reestablishing the ductility of the epoxy composition and reinitiating the curing (e.g., by compression and heating). In order to make a good multilayered composite, the epoxy composition must be capable of "flow" for proper interpenetration between layers. The length of time a prepreg sheet can spend at room temperature before partial cross-linking of the epoxy resin composition occurs is known as the prepreg's "out-life." Premature cross-linking of a prepreg sheet effectively renders it useless for the manufacture of multilayered composites. After manufacturing, a prepreg sheet or roll may be stored in the freezer to extend its out-life prior to shipping or composite manufacture.

Generally, for an epoxy resin composition to be suitable for prepreg composite manufacturing, it should minimally have B-stage state of at least 1 week at room temperature. Ideally, the composition would have a B-stage state of infinity, however, in practice, commercial epoxy composition used in prepreg applications typically have a B-stage specification of months to 1 year.

Certain epoxy resin, compositions described herein exhibit a B-stage state of at least 2 days at room temperature. In some embodiments, the epoxy resin compositions exhibit a B-stage state from about 2 days to about 1 week at room temperature. In some, embodiments, the epoxy resin compositions exhibit a B-stage state from about 1 week to about 2 weeks at room temperature. In some embodiments, the epoxy resin compositions exhibit a B-stage state from about 2 weeks to about 1 month at room temperature. In some embodiments, the epoxy resin compositions exhibit a B-stage state from about 1 day, 2 days, 3 days, 4 days, 5 days, 6 days or more. In some embodiments, the epoxy resin compositions exhibit a B-stage state from about 1 week, 2 weeks, 3 weeks, 4 weeks, or more. In some embodiments, the epoxy resin compositions exhibit a B-stage state from about 1 month, 2 months, 3 months, 4 months, 5 months, 6 months, 7 months, 8 months, 9 months, 10 months, 11 months, or more. In some embodiments, the epoxy resin compositions exhibit a B-stage state from about 1 year, 2 years, or more. It should be understood by those skilled in the art, that the out-life of an epoxy resin compositions will be extended below room temperature, and shortened above room temperature.

Prepregs using certain epoxy resin compositions described herein may exhibit an out-life of at least 1 week at room temperature. In some embodiments, prepregs using the epoxy resin compositions exhibit an out-life of from about 1 week to about 2 weeks at room temperature. In some embodiments, prepregs using the epoxy resin compositions exhibit an out-life of from about 2 weeks to about 4 weeks at room temperature. In some embodiments, prepregs using the epoxy resin compositions exhibit an out-life of from about 1 day, 2 days, 3 days, 4 days, 5 days, 6 days or more. In some embodiments, prepregs using the epoxy resin compositions exhibit an out-life of from about 1 week, 2 weeks, 3 weeks, 4 weeks, or more. In some embodiments, prepregs using the epoxy resin compositions exhibit an out-life of from about 1 month, 2 months, 3 months, 4 months, 5 months, 6 months, 7 months, 8 months, 9 months, 10 months, 11 months, or more. In some embodiments, prepregs using the epoxy resin compositions exhibit an out-life of from about 1 year, 2 years, or more. For composites applications that utilize prepreg and/or filament winding processes, there are effectively three types of curing agents that are widely used with epoxy resins: 1) DICY type curing agents (often in combination with imidazole accelerators); 2) anhydride-based curing agents (often in combination with imidazole accelerators); and 3) aromatic amines such as MDA and DDS. The use of aromatic amines, in particular MDA, has fallen out of favor in the industry due to toxicity concerns. Although aliphatic-type amines represent the most widely used epoxy curatives in the epoxy industry as a whole, they are generally unsuitable for use in filament winding and prepreg applications. The primary reason for this is that aliphatic amines are too reactive. Certain aliphatic polyamine cross-linking agents described herein react much more slowly than the aliphatic amines currently used in composites industry. Accordingly, epoxy resin compositions described herein, containing these aliphatic polyamine cross-linking agents are much more suitable for filament winding and prepreg applications, than many current aliphatic primary amine curratives.

The epoxy compositions described herein should also find use in the infusion of large composite structures, such as the creation of fiberglass composite windmill blades. Typically, the commercially used epoxy systems for windmill blades have moderately working times on the order of a few hours, but not days. It is important for the epoxy composition to have a working time that is sufficiently long enough such that the composition does not cure, prematurely, during the infusion process. On the other hand, it is desirable for the setting time to not be too long after the infusion has be completed. Further, as most epoxy-based wind blades are post-cured in mold on the order of 80° C., then it is important for the epoxy composition to develop a high degree of cure (i.e >98% cure) under this curing temperatures. Certain epoxy compositions described under this invention are suitable to meet such processing requirements, with the added benefit of providing the feature of recyclability. An epoxy resin composition for the construction of a recyclable windmill blade is a specific, but non-limiting, example of an application.

Unlike thermoplastics, thermosetting plastics are generally not recyclable. Cross-linking reactions that occur with conventional epoxies are essentially irreversible, which means the cross-linked materials cannot be re-melted and re-shaped without decomposition. Moreover, the cross-linked materials cannot be readily dissolved in most solvents. As a result, epoxy-based materials such as fiber reinforced epoxies or epoxy-based composite materials are generally not amenable to standard recycling practices. Thus, the epoxy matrix and fibers cannot be readily separated, and/or recovered. As a result, such composite materials have historically been incinerated, land-filled, or ground and repurposed as filler material. As used herein, "recycled" or "recycling" refers to the reuse or recovery, e.g., of an epoxy resin composition. For example, the epoxy compositions described herein can have the ability to be removed, recycled, dissolved, or otherwise reworked after they have been cured. In one embodiment, an epoxy resin composition is recycled by chemically transforming a composition that otherwise behaves as a thermosetting composition into a thermoplastic composition, e.g., a thermoplastic composition with a number average molecular weight or weight average molecular weight of at least 10,000 Da. In one embodiment, the recycling of the composition, e.g., an epoxy composition described herein, is carried out in the presence of an acid.

However, epoxy resin compositions described herein are recyclable even when cross-linked. The reason for this is that cross-linking groups in the cross-linked epoxy polymers are cleavable by chemical means, e.g., including reaction with acid. The cross-linking agent described herein have at least one acid-labile functional group (e.g., a siloxy group, acetal or ketal group that is susceptible to cleavage under acidic conditions). Cross-linked epoxy polymers described herein contain these acid cleavable groups and therefore can be degraded for recycling purposes by treatment with acid.

The intractability of cured epoxy resins, stemming primarily, from their highly cross-linked network that is characteristic of known cured epoxy resins is not an issue with the cured epoxy resins described herein. Cured epoxy resins described herein can result in composites with links in a three-dimensional network structure which can be cleaved under controlled conditions, resulting in disassembly of the three-dimensional network structure into smaller, more soluble molecules and/or polymeric fragments. Degradable cured composites provide a way to recover any articles, reinforcement materials and the like that were in cured composite material. Replacing conventionally used epoxy hardeners with cleavable cross-linking agents described herein effectively solves the present recycling problem associated with epoxy based composites and materials.

Terms such as "hardenable" or "curable" are used interchangeably herein, and are intended to refer to any material that can be stably stored for an extended period of time in a first, malleable or flexible form without loss of flexibility, and transitionable into a second, hardened form after application of an initiating energy thereto. These terms are not intended to be limited to any specific mechanism of hardening. As will be understood by those of skill in the art, a variety of hardening mechanisms can be utilized, depending upon material selection, including for example, curing that is initiated by ultraviolet radiation, visible light, infrared radiation, radio frequency radiation, x-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation and the like.

In one embodiment, the epoxy resin composition comprises an epoxy resin that has an average of at least two epoxide groups per molecule. In one embodiment, the epoxy resin composition comprises a diepoxide resin. In one embodiment, the epoxy resin composition comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin, and combinations thereof.

In some embodiments, the epoxy resin composition comprises an epoxy resin that comprises a blend of epoxy resins. In one embodiment, the epoxy resin composition comprises a blend of bisphenol-based epoxy resins. In one embodiment, the epoxy resin composition comprises a blend of bisphenol-based epoxy resins having an epoxide equivalent weight (EEW) in the range of 160 to 220. In one embodiment, the epoxy resin composition comprises a blend of bisphenol-based epoxy resins having an epoxide equivalent weight (EEW) in the range of 400 to 1500.

In some embodiments, epoxy resins may be blended, filled, or modified with reactive and non-reactive components. In one such embodiment, it may be necessary to adjust the concentration of the curing polyamine agent to cure only the portion of the mix that is reactive; e.g., the resins and any reactive diluent present. In one embodiment, this may be done by calculating the epoxide equivalent weight (EEW) of the total mix and then applying equation 2 (eq. 2) to determine the amount of curing polyamine agent to add to 100 parts of the epoxy resin composition. As an example, an EEW of a blended epoxy resins may be calculated according to equation 4 (eq. 4).

$$EEW \text{ of mix} = \frac{(\text{Total Wt. of Mix})}{(Wta/(EEWa) + Wtb/(EEWb) + \ldots + Wtn/(EEWn))} \quad (\text{eq. 4})$$

wherein Total Wt. of Mix represents the molecular weight of the total mix and includes all materials, both reactive and non-reactive; a, b, . . . and n, are only the materials reactive with the aliphatic polyamine cross-linking agent and are characterized by an epoxy ring; EEWa represents EEW of reactive material a; EEWb represents EEW of reactive material b; and EEWn represents EEW of reactive material n.

In some embodiments, the epoxy resin composition includes a blended epoxy resin, and an aliphatic polyamine cross-linking agent of Formula (I-A) or (I-B) as can be calculated by eq. 3 above. In one embodiment, epoxy resin blend includes a mixture of a diglycidyl ether of a bisphenol, especially bisphenol A, having an EEW of 150-195, typically 180-190, and a diglycidyl ether of a bisphenol, especially bisphenol A having an EEW of 400-1500, preferably 1200-1400. In one embodiment, epoxy resin blend includes a mixture of a diglycidyl ether of a bisphenol, especially bisphenol A, having an EEW of 150-195, typically 180-190, a diglycidyl ether of a bisphenol, especially bisphenol A, having an EEW of 400-1500, preferably 1200-1400, and an epoxy phenolic novalac resin with a functionality of 2.2 to 4, typically 3.6 or above, having an EEW of 170-190, preferably 174-180. In one embodiment, epoxy resin blend includes a mixture of a diglycidyl ether of a bisphenol, especially bisphenol A, having an EEW of 150-195, typically 176, a diglycidyl ether of a bisphenol, typically bisphenol A, having an EEW of 400-1500, preferably 1200-1400, and a tetra-functional epoxy having an EEW of 117-134.

Various bisphenol-based epoxy resin blends may be used to make compositions described herein. In particular, in one embodiment the bisphenol-based epoxy resin is a blend based on the reaction products of epichlorohydrin and bisphenol A ("BPA") and/or bisphenol F ("BPF"). Bisphenol-based epoxy resins that are useful include, but are not limited to, bisphenol A diglycidyl ether, ("BPADGE") and its oligomers and bisphenol F diglycidyl ether, ("BPFDGE") and its oligomers. In some embodiments, molecular weight of preferred oligomers of BPADGE and BPFDGE can be up to approximately 6000 g/mol. In one embodiment, the bisphenol-based epoxy resin based on bisphenol A has a molecular weight in the range of about 340 to about 6000 g/mol. In one embodiment, the bisphenol-based epoxy resin based on bisphenol F has a molecular weight in the range of about 310 to about 6000 g/mol. In some embodiments, the bisphenol-based epoxy resins have a molecular weight between and optionally including any two of the following values: 298, 300, 310, 340, 400, 600, 800, 1000, 1200, 1500, 1800, 2100, 2400, 2700, 3000, 3300, 3600, 3900, 4200, 4500, 4800, 5100, 5400, and 6000. Since the bisphenol-based epoxy resins have 2 epoxy groups per oligomer, the bisphenol-based epoxy resins have an epoxide equivalent weight (EEW) that is generally about half of the molecular weight of the oligomer. In one embodiment, the bisphenol-based epoxy resin is present from about 40 to about 95 wt %, based on the combined weight of the bisphenol-based epoxy resin, amine curing agent, and multi-epoxy reactive diluents. In another embodiment, the bisphenol-based epoxy resin is present from about 40 to about 95 wt %, based on the combined weight of the components in the curable composition. In some embodiments, the bisphenol-based epoxy resin is present in an amount between and optionally including any two of the following values: 40, 45, 50, 55, 60, 65, 70, 75, 80, 85, 90, and 95 wt %, based on the combined weight of the components in the curable composition. In some embodiments, the bisphenol-based epoxy resin contains bromine atoms. Brominated epoxy resins are useful for applications that require flame retardantncy. Specific, but non-limiting, examples of commercially available bisphenol A diglycidyl ether epoxy resins are Insulcast 503/504 BLK; Insulcast 504 Clear; Insulcast 125; Insulcast 333; Insulcast 136; and Insulcast 502, available (from ITW Polymer Technologies (Glenview, Ill., U.S.A.); Epon resins from Hexion Specialty Chemicals, Inc., now Momentive Specialty Chemicals, Inc., part of Momentive Performance Materials Holdings, Inc., (Columbus, Ohio, U.S.A.); D.$^{ERTM}$ resins from The DOW Chemical Company. Specific, but non-limiting, examples of commercially available include bisphenol F diglycidyl ether epoxy resins, including Araldite® GY285, Araldite® GY281, and Araldite® PY302-2 from Huntsman International, LLC (Salt Lake City, Utah, USA). Mixtures of bisphenol-based epoxy resins can be used in the curable composition described herein.

In some embodiments, reactive diluents are added to a bisphenol-based epoxy resin. In some embodiments, monofunctional epoxides are further blended with the bisphenol-based epoxy resin. Reactive diluents are common additives for influencing the viscosity of resin systems. Reactive diluents can also improve the surface qualities of coatings and composites. Specific, but non-limiting, examples of suitable reactive diluents include, $C_{12}$-$C_{14}$ alkyl glycidylethers, o-cresyl glycidylether, and butyl-glycidylether.

In some embodiments, a less than stoichiometric amount of polyamine curing agent of Formula (I-A) or (I-B) is used in the epoxy resin composition described herein. In one embodiment, the epoxy resin composition contains 2% of the stoichiometric amount of polyamine curing agent of Formula (I-A) or (I-B). In one embodiment, the epoxy resin composition contains the cross-linking agent of Formula (I-A) or (I-B) in a percentage selected from the group consisting of about 4%, about 6%, about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, and about 98% of the stoichiometric amount of polyamine curing agent of Formula (I-A) or (I-B).

The curable resin composition described herein is obtained by uniformly mixing the above-described components. A process of obtaining a cured product described herein from the curable resin composition described in detail above may be in accordance with a commonly used curing process of a curable resin composition. The heating temperature condition can be appropriately selected in accordance with the type of curing agent used in the combination or application. In an example of the process, the curable resin composition described herein is heated in the temperature range of about 20° C. to 250° C. Examples of the form of the cured product include a laminate, a cast product, an adhesive layer, a coating film, and a film.

Pultrusion or filament winding generally consists of forming a resin mixture bath, immersion of a glass, carbon, aramid, natural, unnatural fiber (of from about 1-3 mm in diameter) in the mixture for a period of time (typically for about 1 sec), winding the wet fiber on a mandrel, and, subsequently, further curing with heat the composite, which includes the resin mixture and the fiber. The gel times of certain resin mixtures described herein are sufficiently long for filament winding purposes.

Unless otherwise stated herein, the terms "hardener", "curing agent", "cross-linking agent" are used interchangeable as synonyms of "cross-linking agent". As is the case with thermosetting epoxies, the processing properties (e.g. curing time, peak exotherm, mixed viscosity, etc.) and cured resin physical properties (Tg, tensile strength, flexibility modulus, chemical resistance, conductivity, adhesion, color, impact strength, etc.) can be modified by the addition of auxiliary materials to the base epoxy resin/hardener composition for the purposes of preparation of epoxy compositions tailored for a given application. Accordingly, in some embodiments, the epoxy resin composition further includes an auxiliary material selected from the group consisting of flame retardant, accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive and combinations thereof.

In some embodiments, amino molecules that contain 2, or less than 2, active N—H hydrogens can be used in combination with the aliphatic polyamine cross-linking agents of Formula (I-A) or (I-B). Primary monoamines, bis(secondary) diamine molecules, and other molecules that contain only two active N—H hydrogens are suitable for use in the epoxy resin composition described herein, e.g., as chain extenders. In one embodiment, the chain extenders are used to adjust the cross-link density of a cured epoxy resin in accordance with exemplary embodiments described herein. By adding these chain extenders to the polyamine curing agents of Formula (I-A) or (I-B), one can decrease the cross-linking density in the final cured epoxy matrix. Specific, but non-limiting, examples of chain-extendable molecules that contain only two active N—H hydrogens include monoethanolamine, 3-aminopropanol, 2-amino-1-butanol, 2-aminopropanol, 2-aminobutanol, 2-amino-2-methyl-1-propanol [AMP], benzylamine, aniline, p-anisidine, butylamine, piperazine, and N,N'-dimethylethylenediamine, tert-butylamine, and, sec-butylamine. In an embodiment, the epoxy resin composition described herein includes at least one amine chain extender in an amount ranging from about 0% to about 98% relative to weight of the aliphatic polyamine cross-linking agent of Formula (I-A) or (I-B).

One skilled in the art will recognize that the incorporation of chain extenders will alter the processing and mechanical properties of the epoxy composition from that of an epoxy composition that only uses Formula (I-A) or (I-B) as the reactive curing agent. In one embodiment, the use of a chain extender, e.g., because its combination with polyamine curing agent of Formula (2) does not interfere with the recyclability properties of the epoxy composition. In particular, the use of amino alcohols also has the effect of a cure accelerator.

In some embodiments, conventional, polyamino molecules that contain greater than 2 N—H hydrogens are used in combination with polyamine curing agents of Formula (I-A) or (I-B). The composition (e.g., formulation) of conventional epoxy curing agents with the polyamine curing agent of Formula (I-A) or (I-B) will increase the amount of non-degradable cross-links in the final cured epoxy matrix. This action will be, generally, detrimental to the removal and/or recycling of the epoxy composition; however may find use in applications where partial degradation is desired. In one embodiment, non-degradable polyamines in an amount of from about 1 wt. % to 25 wt. % is combined with the polyamine curing agent of Formula (I-A) or (I-B), e.g., to increase the amount of non-degradable cross-links in the final cured epoxy matrix. In one embodiment, non-degradable polyamine in an amount selected from the group consisting of about 1 wt. % to about 25 wt. %, about 2 wt. % to about 25 wt. %, about 3 wt. % to about 25 wt. %, about 4 wt. % to about 25 wt. %, about 5 wt. % to about 25 wt. %, about 6 wt. % to about 7 wt. %, about 8 wt. % to about 25 wt. %, about 9 wt. % to about 25 wt. %, about 10 wt. % to about 25 wt. %, about 11 wt. % to about 25 wt. %, about 12 wt. % to about 25 wt. %, about 13 wt. % to about 25 wt. %, about 14 wt. % to about 25 wt. %, about 15 wt. % to about 25 wt. %, about 16 wt. % to about 25 wt. %, about 17 wt.

% to about 25 wt. %, about 18 wt. % to about 25 wt. %, about 19 wt. % to about 25 wt. %, about 20 wt. % to about 25 wt. %, about 21 wt. % to about 25 wt. %, about 22 wt. % to about 25 wt. %, about 23 wt. % to about 25 wt. %, and about 24 wt. % to about 25 wt. % of the epoxy composition is combined with the polyamine curing agent of Formula (I-A) or (I-B), e.g., to increase the amount of nondegradable cross-links in the final cured epoxy matrix. Specific, but non-limiting examples of conventional polyamines include polyetheramines and ethyleneamines; and cycloaliphatic and aromatic classes of diamino and/or polyamino molecules.

In some embodiments, the epoxy resin composition further includes a reinforcing agent. In one embodiment, the reinforcing agent is selected from a group consisting of glass fiber, carbon fiber, carbon nanotube fiber, cellulose fiber, natural fiber, chemical fiber, and non-natural fiber. The fiber may be woven or non-woven, unidirectional or multi-directional, chopped matt or any combination thereof. The methods described herein is not limited to the method of applying the epoxy resin composition to the fiber. For example, infusion, wet lay-up, resin transfer molding, vacuum bagging, and other standard composite techniques may also be used In some embodiments, the epoxy resin composition further includes a non-fiber reinforcing agent. Specific, but non-limiting examples, of non-fiber reinforcing agents include carbon nanotube, carbon black, metal nanoparticle, organic nanoparticle, iron oxide, boron nitride, and combinations thereof.

The conventional aliphatic amines that are widely used in coatings and composite applications, like for example, polyethyleneamines, and cycloaliphatic amines (e.g., isophorone diamine) have gel times ranging from minutes to hours at room temperature and do not possess sufficient latency. This reactivity profile makes certain aliphatic amine molecules effectively unsuitable for applications such as filament winding and pultrusion.

Certain polyamino curing agents described herein (e.g., certain polyamino curing agents of Formula (I-A) or Formula (I-B) as described herein) overcome these limitations of conventional aliphatic amines used in the art in two major ways: 1) they have low reactivity with epoxy resins at ambient temperatures; and 2) the contain an acid labile linkages, allowing a cured epoxy to be transformed (i.e. removed and recycled) by simple immersion in an acidic recycling bath.

As described herein, a specific set of acid-labile and aliphatic amines is provided, e.g., a compound of Formula (I-A) or (I-B) as described herein, which possess suitable processing, mechanical, thermal, properties, e.g., for pultrusion, filament winding or large part infusion. These polyamine hardeners can be formulated to create epoxy composition suitable for the fabrication of composites that may serve as the structural materials or reinforcing materials. Furthermore, the curing agents provide a thermosetting epoxy matrix that enables the fabrication of inherently recyclable thermosetting materials. The structure of the cross-links in the cured epoxy matrix from the epoxy compositions disclosed herein is designed in such a way that they are programmed to cleave upon immersion in an acidic recycling bath. The acidic bath induces cleavage of the acid-labile linkages in the thermoset, converting into its thermoplastic counterpart. Both the concentration of acid, and the acid strength (i.e. pH) of the recycling bath can be used to modulate the conversion of the reworkable thermoset into a thermoplastic. The nature of the acid-labile ketal/acetals group can be used as a handle to control the recycling time. Polymers modified with acid-cleavable groups have been successfully implemented in both photoresist and drug delivery applications. The common premise in these cases is that acid-induced cleavage will result in a solubility change in the parent material. This change is then taken advantage of for a technological purpose. The concept of recyclable/reworkable epoxy is somewhat similar, albeit the desired change is to transform an otherwise intractable material into a tractable one that is of high inherent value. The cleavage groups in the programmed epoxy hardeners will exist at every cross-link point in the cured epoxy matrix. Immersion of the cured epoxy in a specific recycling bath will induce cleavage of the cross-links and conversion of the thermoset plastic into its thermoplastic epoxy counterpart. This transformation occurs at an appreciable rate only upon immersion of the thermoset in a solution of sufficient temperature, acid strength and concentration. Generally, most epoxy and composite applications operate in environments that are far away from what is required to trigger the programmed epoxy to convert (e.g., degrade, de-crosslink). The thermoplastic offset is completely insoluble in water, but may be solubilized into an acidic recycling solution because of protonation of the polymer backbone. Thus, any other articles in contact with the initial thermoset (fibers, metal, etc) may be physically removed from the recycling bath and then the dissolved epoxy thermoplastic recovered after a processing step such as evaporation or precipitation.

In some embodiments, the fibers, metals, copper sheet, additives, plastics, or any other articles that are insoluble under the acid bath, may be recovered by physical removal from the resultant/recycling solution. Further, if the converted thermoplastic is dissolved under the operation, it may be recovered from the solution via a simple precipitation or evaporation process. An advantage of the described epoxy resin compositions and methods is that essentially all of the high value input materials bonded together by the cured recyclable epoxy composition may be recovered via a simpler, and low energy recycling process, which is afforded by the use of Formula (I-A) or (I-B) cross-linking agents. Such a recycling process may be performed at the site of product manufacturing, whereby post-production thermoset article waste can be recycled instead of being thrown in the landfill. The described epoxy resin compositions and methods have important environmental and economic implications, as the development of a recyclable thermoset materials is a long-standing challenge of the industry.

As described herein, novel polyamine hardener Formula (I-A) or (I-B) when used with a typical epoxy resin makes it possible to fabricate epoxy laminates and composite structures, wherein the epoxy can be dissolved, separated and recovered. Among the embodiments of this invention is the incorporation of additional auxiliary material(s) to the base-epoxy composition (i.e., the "A-stage formulation"). The described epoxy resin compositions and methods have the distinct advantage that it enables the manufacture of recyclable products.

In an embodiment, the described epoxy resin compositions and methods have the distinct advantage that it provides epoxy compositions for the fabrication of more easily recycled epoxy-based products. The described epoxy resin compositions and methods are not limited with respect to the exact method used, e.g., to make the laminate or composite product that is used to make a final product. Specific, but non-limiting examples, of procedures for forming composites and laminates involve such operations (which are well known in the composite industry):

A) Wet lay up
B) Infusion
C) filament winding or pultrusion
D) Resin transfer molding, and its derivatives such as e.g., vacuum assisted resin transfer molding, high pressure resin transfer molding, and the like
E) compression molding and wet compression Furthermore, in order to exhibit flame retardancy, the curable resin composition described herein may contain a non-halogenated flame retardant that substantially contains no halogen atoms within the range that does not degrade reliability. Specific, but non-limiting examples of non-halogenated flame-retardants include phosphorus-based flame retardants, inorganic flame retardants, silicone-based flame retardants, inorganic flame retardants, and organic metal salt-based flame retardants. The use of such flame retardants may be used alone or in a plurality.

As the phosphorus-based flame retardants, both inorganic compounds and organic compounds can be used. Examples of the inorganic compounds include red phosphorus; ammonium phosphates such as monoammonium phosphate, diammonium phosphate, triammonium phosphate, and ammonium polyphosphate; and inorganic nitrogen-containing phosphorus compounds such as phosphoric acid amide.

Red phosphorus is preferably subjected to a surface treatment in order to prevent hydrolysis or the like. Examples of the process of the surface treatment include (i) a process of coating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a process of coating with a mixture of an inorganic compound such as magnesium hydroxide, aluminum hydroxide, zinc hydroxide, or titanium hydroxide and a thermosetting resin such as a phenolic resin, and (iii) a process of coating with a film composed of an inorganic compound such as magnesium hydroxide, aluminum hydroxide, zinc hydroxide, or titanium hydroxide and further coating the inorganic compound film with a film composed of a thermosetting resin such as a phenolic resin.

Examples of the organic phosphorus-based compound include general-purpose organic phosphorus-based compounds such as phosphate ester compounds, phosphonic acid compounds, phosphinic acid compounds, phosphine oxide compounds, phosphorane compounds, and organic nitrogen-containing phosphorus compounds. Examples further include cyclic organic phosphorus compounds such as 9,10-dihydro-9-oxa-10-phosphaphenanthrene-10-oxide, 10-(2,5-dihydroxyphenyl)-10H'9-oxa-10-phosphaphenanthrene-10-oxide, and 10-(2,7-dihydroxynaphthyl)-10H-9-oxa-10-phosphaphenanthrene-10-oxide; and derivatives obtained by allowing any of these compounds react with a compound such as an epoxy resin or a phenolic resin. Diethyl-aluminum phosphinates (e.g., Exolit® products from Clariant) are particularly efficacious halogen-free flame retardants.

The amount of the phosphorus-based flame retardant is appropriately selected in accordance with the type of phosphorus-based flame retardant, other components of the curable resin composition, and the degree of desired flame retardancy. For example, when red phosphorus is used as the non-halogen flame retardant in 100 parts by mass of a curable resin composition containing all components, such as an epoxy resin, a curing agent, a non-halogen flame retardant, and other fillers and additives, red phosphorus is preferably incorporated in an amount in the range of 0.1 to 2.0 parts by mass. When an organic phosphorous compound is used, similarly, the organic phosphorous compound is incorporated in an amount preferably in the range of 0.1 to 10.0 parts by mass, and particularly preferably in the range of 0.5 to 6.0 parts by mass.

When the phosphorous-based flame retardant is used, the phosphorous-based flame retardant may be used in combination with, for example, hydrotalcite, magnesium hydroxide, boron compounds, zirconium oxide, black dyes, calcium carbonate, zeolite, zinc molybdate, or activated carbon.

Examples of nitrogen-based flame retardants include triazine compounds, cyanuric acid compounds, isocyanuric acid compounds, and phenothiazine. In some embodiments, the nitrogen-based flame retardants are selected from triazine compounds, cyanuric acid compounds, or isocyanuric acid compounds.

Examples of triazine compounds include melamine, acetoguanamine, benzoguanamine, melon, melam, succinoguanamine, ethylenedimelamine, melamine polyphosphate, and triguanamine. Besides these compounds, examples thereof further include (i) aminotriazine sulfate compounds such as guanylmelamine sulfate, melem sulfate, and melam sulfate; (ii) co-condensates of a phenol such as phenol, cresol, xylenol, butylphenol, or nonylphenol, a melamine such as melamine, benzoguanamine, acetoguanamine, or formguanamine, and formaldehyde; (iii) mixtures of the cocondensate (ii) mentioned above and a phenolic resin such as a phenol-formaldehyde condensate; and (iv) those obtained by modifying the cocondensate (ii) or the mixture (iii) with, for example, tung oil or isomerized linseed oil.

Specific examples of the cyanuric acid compound include cyanuric acid and melamine cyanurate.

The amount of the nitrogen-based flame retardant is appropriately selected in accordance with the type of nitrogen-based flame retardant, other components of the curable resin composition, and the degree of desired flame retardancy. For example, the nitrogen-based flame retardant is preferably incorporated within the range of 0.05 to 10 parts by mass, and particularly preferably 0.1 to 5 parts by mass relative to 100 parts by mass of a curable resin composition containing all components, such as an epoxy resin, a curing agent, a non-halogen flame retardant, and other fillers and additives.

When the nitrogen-based flame retardant is used, for example, a metal hydroxide or a molybdenum compound may be used in combination.

The silicone-based flame retardants are not particularly limited so long as the flame retardant is an organic compound having a silicon atom. Examples thereof include silicone oil, silicone rubber, and silicone resins.

The amount of the silicone-based flame retardant is appropriately selected in accordance with the type of silicone-based flame retardant, other components of the curable resin composition, and the degree of desired flame retardancy. For example, the silicone-based flame retardant is preferably incorporated within the range of 0.05 to 20 parts by mass relative to 100 parts by mass of a curable resin composition containing all components, such as an epoxy resin, a curing agent, a non-halogen flame retardant, and other fillers and additives. When the silicone-based flame retardant is used, for example, a molybdenum compound or alumina may be used in combination.

Examples of the inorganic flame retardant include metal hydroxides, metal oxides, metal carbonate compounds, metal powders, boron compounds, and low-melting-point glass.

Specific examples of the metal hydroxide include aluminum hydroxide, aluminum oxide hydroxide, magnesium hydroxide, dolomite, hydrotalcite, calcium hydroxide, barium hydroxide, and zirconium hydroxide.

Specific examples of the metal oxide include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Specific examples of the metal carbonate compound include zinc carbonate, magnesium carbonate, calcium carbonate, barium carbonate, basic magnesium carbonate, aluminum carbonate, iron carbonate, cobalt carbonate, and titanium carbonate.

Specific examples of the metal powder include powders of aluminum, iron, titanium, manganese, zinc, molybdenum, cobalt, bismuth, chromium, nickel, copper, tungsten, and tin.

Specific examples of the boron compound include zinc borate, zinc metaborate, barium metaborate, boric acid, and borax.

Specific examples of the low-melting-point glass include Seaplea (Bokusui Brown Co., Ltd.), hydrated glass $SiO_2$—$MgO$—$H_2O$, $PbO$—$B_2O_3$-based, $ZnO$—$P_2O_5$—$MgO$-based, $P_2O_5$—$B_2O_3$—$PbO$—$MgO$-based, P—Sn—O—F-based, $PbO$—$V_2O_5$—$TeO_2$-based, $Al_2O_3$—$H_2O$-based, and lead borosilicate-based glassy compounds.

The amount of the inorganic flame retardant is appropriately selected in accordance with the type of inorganic flame retardant, other components of the curable resin composition, and the degree of desired flame retardancy. For example, the inorganic flame retardant is preferably incorporated within the range of 0.05 to 100 parts by mass, and particularly preferably from 5 to 30 parts by mass relative to 100 parts by mass of a curable resin composition containing all components, such as an epoxy resin, a curing agent, a non-halogen flame retardant, and other fillers and additives.

Examples of the organic metal salt-based flame retardant include ferrocene, acetylacetonate metal complexes, organometallic carbonyl compounds, organic cobalt salt compounds, organic sulfonic acid metal salts, and compounds obtained by ionic bonding or coordinate bonding of a metal atom and an aromatic compound, or a heterocyclic compound.

The amount of the organic metal salt-based flame retardant is appropriately selected in accordance with the type of organic metal salt-based flame retardant, other components of the curable resin composition, and the degree of desired flame retardancy. For example, the organic metal salt-based flame retardant is preferably incorporated within the range of 0.005 to 10 parts by mass relative to 100 parts by mass of a curable resin composition containing all components, such as an epoxy resin, a curing agent, a non-halogen flame retardant, and other fillers and additives.

The curable resin composition described herein may contain inorganic fillers, if necessary. Some specific, but non-limiting, examples of the inorganic filler include fused silica, fumed silica, crystalline silica, alumina, silicon nitride, and aluminum hydroxide, aluminum oxide hydroxide, talc, micro glass beds, etc. In consideration of flame retardancy, the filling ratio of the filler, is preferably high and is particularly preferably 0.20% by mass or more of the total amount of the curable resin composition. When the curable resin composition is used in the application of an electrically conductive paste or the like, an electrically conductive filler such as a silver powder or a copper powder can be used.

Various compounding agents such as a silane coupling agent, a mold release agent, a pigment, and an emulsifier may be optionally added to the curable resin composition described herein.

In some embodiments, epoxy resin composition described herein further includes a reinforcing agent. In one embodiment, reinforcing agent is selected from a group consisting of glass fiber, carbon fiber, natural fiber, and chemical fiber; and the non-fibrous material is at least one selected from a group consisting of carbon nanotube, carbon black, metal nanoparticle, organic nanoparticle, iron oxide, boron nitride, and combinations thereof.

In another aspect, described herein is a method of curing an epoxy resin composition described herein. In one embodiment, the method comprises heating an epoxy resin composition described herein to form a cured epoxy resin composition. In one embodiment, the epoxy resin composition is cured to a curing degree of at least 5% cure (e.g., as determined by infrared (IR) spectroscopy, differential scanning calorimetry (DSC), or other methods used by a person of skill in the art. In one embodiment, the epoxy resin composition is cured to a curing degree of at least 10%, 20%, 30%, 40%, 50%, 60%, 70%, 80%, 90%, 95% cure.

In some embodiments, the method of curing an epoxy resin composition described herein is used to produce reinforced composite. In one embodiment, the method of curing an epoxy resin composition described herein produces a composite reinforced with a reinforcing component selected from the group consisting of glass fibers, aramid fibers, graphite fibers, carbon fibers, natural fibers, non-natural fibers and combinations thereof.

In one embodiment, the cross-linked polymer matrix is reinforced with a reinforcing agent derived from a reinforcing component selected from the group consisting of glass fibers, aramid fibers, graphite fibers, carbon fibers, natural fibers, non-natural fibers and combinations thereof. In one embodiment, the cross-linked polymer matrix is a cross-linked epoxy resin, wherein the epoxy resin is selected from the group consisting of glycidyl ether epoxy resin, glycidyl ester epoxy resin, glycidyl amine epoxy resin, alicyclic epoxy resin, aliphatic epoxy resin, and phenolic epoxy resin. In one embodiment, the cross-linked polymer matrix is reinforced with the reinforcement material selected from the group consisting of a fibrous material and a non-fibrous material. In one embodiment, the cross-linked polymer matrix is reinforced with a fibrous material selected from a group consisting of glass fiber, carbon fiber, natural fiber, and chemical fiber. In one embodiment, the cross-linked polymer matrix is reinforced with a non-fibrous material selected from the group consisting of carbon nanotube, carbon black, metal nanoparticle, organic nanoparticle, iron oxide, and boron nitride. In one embodiment, the reinforced cross-linked polymer matrix includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, and gloss additive. In some embodiments, the reinforced cross-linked polymer matrix is prepared by at least one method selected from the group consisting of wet lay-up, vacuum infusion, filament winding, and resin transfer molding, prepreg, and compression molding.

In another aspect, described herein is a method for recycling a cross-linked polymer matrix described herein. FIG. 1 shows a non-limiting example of the method for recycling a cross-linked polymer matrix described herein. In one embodiment, the method for recycling the cross-linked polymer matrix comprises degrading the cross-linked polymer matrix with an acid in the presence of a solvent. In one embodiment, degrading the cross-linked matrix with an acid in the presence of a solvent is performed under a heating condition. In one embodiment, the cross-linked polymer matrix is degraded with an acid selected from a group consisting of hydrochloric acid, acetic acid, lactic acid, formic acid, propionic acid, citric acid, methane sulfonic acid, p-toluene sulfonic acid, sulfuric acid, benzoic acid, and phthalic acid. In one embodiment, the cross-linked polymer matrix is degraded with an acid in the presence of a solvent selected from the group consisting of methanol, ethanol, ethylene glycol, dimethyl sulfoxide, isopropyl alcohol, butyl alcohol, pentanol, hexanol, heptanol, octanol alcohol, nonyl alcohol, water, dimethylsulforide and combinations thereof. In one embodiment, the cross-linked polymer matrix is degraded with an acid in an amount ranging from about 2% to 90% by weight of the cross-linked polymer matrix.

In some embodiments, the method for recycling a cross-linked polymer matrix includes the step of recovering a degradation product of the cross-linked polymer matrix via a filtration process and/or a precipitation process.

In general, the diamino compounds of Formula (I-A) or (I-B) can be used as monomers and/or cross-linkers to make polymeric materials such as nylons, epoxies, polyurethanes, acrylamides or other type polymers or cross-linked polymers and/or materials. The diamino compounds of Formula (I-A) or (I-B) can also be used as monomers or cross-linkers for the preparation of designer materials that can further be imbued with the ability to degrade under acidic conditions. Polymer degradation can be accomplished with these materials because, inter alia, the incorporated siloxy, acetal and ketal linkages are susceptible to cleavage by various chemical means. For example, the siloxy, acetal and ketal linkages can be cleaved by hydrolysis under acidic conditions. Thus, use of the present compounds of Formula (I-A) or (I-B) as monomers produce polymeric structure that can be predictably degraded into smaller molecular fragments under acidic conditions.

In some embodiments, the epoxy resin composition disclosed herein can be used as an adhesive composition. In some embodiments, the epoxy composition disclosed herein can be used as a coating composition. In some embodiments, the epoxy composition disclosed herein can be used as an encapsulation material. In some embodiments, the epoxy composition disclosed herein can be used as epoxy flooring, to provide a recyclable floor. In some embodiments, the epoxy composition disclosed herein can be used as epoxy countertop, to provide recyclable countertop. In some embodiments, the epoxy composition disclosed herein can be used to create a recyclable windmill blade.

The present disclosure details cleavable compounds that provide epoxy resin compositions that are suitable for use in industrial composite manufacturing techniques such as filament winding, pultrusion, prepreg, which are process that are otherwise not applicable to epoxy compositions that contain aliphatic polyamines. The epoxy resin compositions described herein may be used in oil and gas-related applications, e.g., for Cured In Place Pipe Repair (CIPP). Additionally, the epoxy compositions described herein have the ability to be easily removed, recycled, dissolved, or otherwise reworked after they have been cured. In an embodiment, a fluid can pass through an industrial composite comprising the epoxy composition described herein. In an embodiment, a first, non-dissolving (e.g., non-acidic) fluid is passed through the industrial composite comprising the epoxy composition described herein. In an embodiment, a second, dissolving (e.g., acidic) fluid is pass through the industrial composite comprising the epoxy composition described herein (e.g., to dissolve or degrade the epoxy composition described herein). The epoxy compositions described herein can also not be recycled or reworked. Thus, the described epoxy resin compositions and methods should find industrial application that include, as non-limiting examples, removable coatings and encapsulates, recyclable carbon fiber thermoset composites, recyclable fiberglass thermoset composites. An example of an industrial application for the epoxy compositions described herein include repair of e.g., an underground pipe, e.g., by layering a fiberglass sleeve in the resin. In some embodiments, the epoxy resin composition has enhanced pliability (due to its steric hindrance). An epoxy resin composition for CIPP is a specific, but non-limiting, example of an application.

It will be appreciated by those skilled in the art that changes could be made to the exemplary embodiments shown and described above without departing from the broad inventive concept thereof. It is understood, therefore, that the described epoxy resin compositions and methods are not limited to the exemplary embodiments shown and described, but it is intended to cover modifications within the spirit and scope of the disclosure and as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the methods described herein should not be limited to the performance of their steps in the order written, and one skilled in the art can readily appreciate that the steps may be varied and still remain within the spirit and scope of the present invention.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-4}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl (C), and 3-pentanyl ($C_5$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and, "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), and the like. Exemplary substituted alkylene groups, e.g., substituted with one or more alkyl (methyl) groups, include but are not limited to, substituted methylene (—CH(CH$_3$)—, —(—C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH═CH—) and propenylene (e.g., —CH═CHCH$_2$—, —CH$_2$—CH═CH—). Exemplary substituted alkenylene groups, e.g., substituted with one or more alkyl (methyl) groups, include but are not limited to, substituted ethylene (—C(CH$_3$)═CH—, —CH═C (CH$_3$)—), substituted propylene (e.g., —C(CH$_3$) ═CHCH$_2$—, —CH═C(CH$_3$)CH$_2$—, —CH═CHCH (CH$_3$)—, —CH═CHC(CH$_3$)$_2$—, —CH(CH$_3$)—CH═CH—, —C(CH$_3$)$_2$—CH═CH—, —CH$_2$—C(CH$_3$) ═CH—, —CH$_2$—CH═C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Fused aryl" refers to an aryl having two of its ring carbon in common with a second aryl or heteroaryl ring or with a carbocyclyl or heterocyclyl ring.

"Amino" refers to the radical —$NH_2$.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

As used herein, the term "PASi" refers to polyamino silicon.

As used herein, a "salt" of a compound refers to a compound having at least one anionic charge, cationic charge, or both, where each charge has associated with it a counterion. "Counterion" refers to an ion that balances the compound's anionic or cationic charge. Non-limiting exemplary counterions are anions such as chloride, bromide, fluoride, iodide, acetate, carboxylate, hydrogen sulfate, nitrate, and phenolate, sulfonate, sulfate, and phosphate.

EXAMPLES

In order that the invention described herein may be more fully understood, the following examples are set forth. The examples described in this application are offered to illustrate the aspects of the invention and their embodiments provided herein and are not to be construed in any way as limiting their scope.

For some exemplary PASi compounds described below where, in one instance, two different types of aminophenol and/or aminopropanol or ethanolamine substituents are attached to the silicon (e.g., the aminophenol and aminopropanol or ethanolamine substituents of the compounds of Examples 4, 5, and 11), the reaction used to synthesize these PASi compounds can also produce a mixture of other PASi compounds with varying degrees of substitution of each different type of aminophenol and/or aminopropanol or ethanolamine substitutent (e.g., as a mixture of compounds wherein each compound is represented by the compounds of Formula (III-A) and Formula (IV-A) as described herein) and can be isolated as such a mixture. For example, the PASi compounds according to Examples 4 and 5 (i.e., bis(4-aminophenyl) bis(2-aminoethyl) orthosilicate and bis(4-aminophenyl) bis(1-aminopropan-2-yl) orthosilicate, respectively) are drawn in these examples to represent the relative molar amount of the aminophenol and aminopropanol or ethanolamine substituents used in the reaction (i.e., a 1:1 ratio as represented by the equal number aminophenol and aminopropanol or ethanolamine substitutions). One skilled in the art would understand these reactions may also result in the production of other PASi compounds with other degrees of substitution of each aminophenol, aminopropanol, or ethanolamine substitutent (e.g., other PASi compounds in the ratios described in Examples 4 and 5 below). The compositions described in the below examples can also comprise the reaction products resulting from a mixture of PASi compounds with an epoxy resin, even though only one structure of the PASi is depicted to reflect the relative molar amount of the aminophenol, aminopropanol, and ethanolamine substitutents used (e.g., the PASi compounds described by Examples 4 and 5).

I. Synthesis of Polyamino Silicon (PASi) Compounds

Synthesis of examples of polyaminosilicon compounds of type Formula

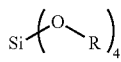

Example 1. Synthesis of tetrakis(2-aminoethyl) orthosilicate

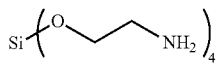

A round-bottom-flask was equipped with an efficient rectification column with a distillation condenser, a thermocouple, and a heating mantle. The flask was charged with 104 g (0.5 mole) of triethoxysilane, 188 g (2.1 moles) of ethanolamine. The temperature of the reaction mixture was gradually increased until boiling. Once distillation of low boiling components started, the heat was increased further until temperature of the flask reached ~200° C. while distilling off. At this temperature a vacuum of about 100 mmHg was applied and heating was continued while distilling and vacuum was increased to ~1 mmHg. When the temperature of distillation head reached 180° C. @ 1-2 mmHg, the product was collected (recorded boiling point of 179° C. @ 2 mmHg) while keeping the pot temperature below 200° C. Yield of the product was 54 g (40% theoretical yield). $^{29}$Si NMR and $^1$H NMR conformed to structure. $^1$H NMR (400 MHz, CDCl$_3$) δ 2.34-2.36 (m, 8H, 4×NCH$_2$), 3.28-3.36 (m, 8H, 4×OCH$_2$). $^{29}$Si NMR (79 MHz, CDCl$_3$) δ −82.18 (s).

Example 2. Synthesis of tetrakis(1-aminopropan-2-yl) orthosilicate

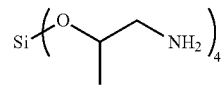

A distillation unit was configured as follows: a 50-liter steel round bottom flask was equipped with a very efficient rectification column (3 ft tall, 2 in diameter) packed with Raschig rings, a distillation condenser, a reflux regulator and a 22 L receiver, thermocouple and a heating mantle. The flask was charged with 28.05 kg (373.5 moles, 4.5 eq.) of isopropanolamine (93% purity with 7-10% of 2-amino-1-propanol), 12.6 kg (83 moles) of tetramethylorthosilicate and 20 g of titanium (IV) isopropoxide. The system was purged with nitrogen and the temperature of the reaction mixture was gradually increased until boiling. Once distillation of low boiling components started, the heat was increased further until temperature of the flask reached 162° C. while continuously distilling off low boiling components over 2 days. A total of 8.12 kg of distillate was collected at reflux ratio of 4:1 and the head temperature was maintained at 58-60° C., which corresponds to boiling point of methanol. The reaction mixture was allowed to cool down to room temperature overnight. A vacuum of about 5-20 mmHg was then applied and heating was continued while distilling for 8 hours until temperature of the flask reached 150° C. and the temperature of the head reached 78° C. An additional 5.2 kg of the distillate was collected. The crude product (25.5 kg) was collected from the distillation unit and transferred in portions to a 20 L round-bottom flask equipped with a short path distillation head and an efficient condenser with a receiver: The title product was flash-distilled at internal flask temperature of 184-202° C. and a distillation head temperature of 159-184° C. @ 0.25-1 mmHg. The isolate yield of the product was 22.1 kg (82% theoretical yield). $^{29}$Si NMR and $^1$H NMR conformed to the title structure comprising of ~3:1 ratio of Si(OCH(CH$_3$)CH$_2$NH$_2$)$_4$ and CH$_3$OSi(OCH(CH$_3$)CH$_2$NH$_2$)$_3$. As the commercially available isopropanolamine used in this reaction contained ~90:10 ratio of 1-aminopropanol:2-aminopropanol, products containing 2-aminopropanol also appeared <10% in the spectrum. The title compound Si(OCH(CH$_3$)CH$_2$NH$_2$)$_4$: $^{29}$Si NMR (CDCl$_3$) δ −85.89 (s); $^1$H NMR (400 MHz, CDCl$_3$) δ 1.10-1.24 (m, 20H, 4×CCH$_3$, 4× NH$_2$), 2.60-2.74 (m, 8H, 4× CH$_2$), 4.00-4.10 (m, 4H, 4× CH). A minor compound CH$_3$OSi(OCH(CH$_3$)CH$_2$NH$_2$)$_3$: $^{29}$Si NMR (CDCl$_3$) δ −85.06 (s). a minor compound Si(OCH$_2$CH(CH$_3$)NH$_2$)(OCH(CH$_3$)CH$_2$NH$_2$)$_3$: $^{29}$Si NMR (CDCl$_3$) δ −85.85 (s).

Example 3. Synthesis of tetrakis(2-amino-2-methylpropyl) orthosilicate

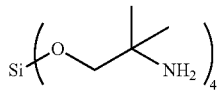

A 3-neck round-bottom-flask was equipped with a very efficient rectification column with a distillation condenser, a thermocouple and a heating mantle. The flask was charged with 458 g (2.2 moles) of triethoxysilane, 802.3 g of 2-amino-2-methylpropanol (9 moles) and 0.5 g titanium (IV) isopropoxide. The reaction mixture was stirred at room temperature for 1-2 hours and the heating was gradually increased until boiling over 2-3 hours. Once distillation of low boiling components started, the heat was increased further until temperature of the flask reached 150° C. while distilling off. At this temperature vacuum of about 100 mmHg was applied and heating was continued while distilling over 5 hours and then the vacuum was changed to ~1 mmHg. When the temperature of distillation head reached ~100° C. @ 1-2 mmHg, the product was collected (recorded boiling point of 150° C. @ 0.7 mmHg) while keeping the pot temperature below 200° C. Yield of the product was 630 g (75% theoretical yield). $^{29}$Si NMR and conformed to structure: $^{29}$Si NMR (79 MHz, CDCl$_3$) δ −83.07.

Example 4. Synthesis of bis(4-aminophenyl) bis(2-aminoethyl) orthosilicate

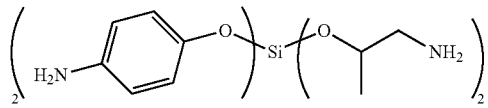

A distillation unit was configured as follows: a 50-liter steel round bottom flask was equipped with a very efficient rectification column (3 ft tall, 2 in diameter) packed with Raschig rings, a distillation condenser, a reflux regulator and a 22 L receiver, thermocouple and a heating mantle. The flask was charged with 17.2 kg (157.6 moles, 2 eq.) of 4-aminophenol and flushed with nitrogen. 25.58 kg (78.8 moles) of distilled tetrakis(2-aminopropyl) orthosilicate was added. The system was purged again, and high vacuum was applied. The temperature of the reaction mixture was gradually increased until the temperature of the flask reached 176° C. while continuously distilling off low boiling components over 2 days. A total of 11.3 kg of distillate was collected at a head temperature at 65-67° C. @ 4-17 mmHg, which corresponds to boiling point of isopropanolamine. The reaction mixture was allowed to cool down to room temperature overnight and the title product (30.8 kg) was collected from the distillation unit (100% theoretical yield). $^{29}$Si NMR and $^1$H NMR conformed to structure comprising of 1:2:1 ratio of Si(OCH(CH$_3$)CH$_2$NH$_2$)(OC$_6$H$_4$NH$_2$)$_3$, Si(OCH(CH$_3$)CH$_2$NH$_2$)$_2$(OC$_6$H$_4$NH$_2$)$_2$, and Si(OCH(CH$_3$)CH$_2$NH$_2$)$_3$(OC$_6$H$_4$NH$_2$). $^1$H NMR (400 MHz, CDCl$_3$) δ 1.17-1.21 (m, 6H, 2× CH$_3$), 1.20-1.45 (br, 4H, 2× NH$_2$), 2.60-2.70 (m, 8H, 4× CH$_2$), 3.40-3.60 (br, 4H, 2× PhNH$_2$), 4.09-4.15 (m, 4H, 4× CH), 6.50-6.60 (m, 4H, ArH), 6.80-6.85 (m, 4H, ArH). $^{29}$Si NMR (79 MHz, CDCl$_3$) δ −95.86 (s, Si(OCH(CH$_3$)CH$_2$NH$_2$)(OC$_6$H$_4$NH$_2$)$_3$; −92.16 (s, Si(OCH(CH$_3$)CH$_2$NH$_2$)$_2$(OC$_6$H$_4$NH$_2$)$_2$; −88.67 (s, Si(OCH(CH$_3$)CH$_2$NH$_2$)$_3$(OC$_6$H$_4$NH$_2$). The tetrakis(2-aminopropyl) orthosilicate used in this reaction was prepared from commercially available propanolamine that contained a 10:1 ratio of 1-aminopropanol:2-aminopropanol. The products formed by 1-aminopropanol appeared <10% in the spectrum: $^{29}$Si NMR (79 MHz, CDCl$_3$) δ −91.27 (s), −87.75 (s).

Example 5. Synthesis of bis(4-aminophenyl) bis(1-aminopropan-2-yl) orthosilicate

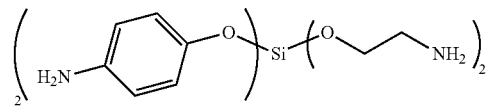

A 0.5-liter glass round bottom flask was equipped with a very efficient rectification column (1 ft tall, 1 in diameter) packed with Raschig rings, a distillation head with condenser, and a 2 L receiver, thermocouple and a heating mantle. The flask was charged with 672 g (11 moles, 2 eq.) of ethanolamine, 1200 g (11 moles, 2 eq.) of 4-aminophenol, 837.2 g (5.5 moles, 1 eq.) of tetramethyl orthosilicate and 1.5 g titanium (IV) isopropoxidepoxide. The system was purged with nitrogen and temperature of the reaction mixture was gradually increased. At 35° C. reaction mixture homogenized. Total of 252 g of distillate was collected when the temperature of the flask reached 120° C. while continuously distilling off low boiling components over 10 hours. At this time distillation was switched to vacuum and additional 212 g was distilled until the internal flask temperature reached 150° C. High vacuum was applied and 180 g was distilled until pot temperature stabilized at 150° C. A total of 644 g of distillate was collected. Theoretical amount of distillate is 704 g (corresponds to 22 moles of methanol). The reaction mixture was allowed to cool down to room temperature overnight and the title product (1.9 kg) was collected from the distillation unit (95% theoretical yield). The NMR conformed to structure comprising of a 1:2:1 ratio of Si(OCH$_2$CH$_2$NH$_2$)(OC$_6$H$_4$NH$_2$)$_3$, Si(OCH$_2$CH$_2$NH$_2$)$_2$(OC$_6$H$_4$NH$_2$)$_2$, and Si(OCH$_2$CH$_2$NH$_2$)$_3$(OC$_6$H$_4$NH$_2$). $^1$H NMR (400 MHz, CDCl$_3$) δ 1.10-1.50 (br, 4H, 2× NH$_2$), 2.68-2.83 (m, 4H, 2× CH$_2$N), 3.30-3.70 (br, 4H, PhNH$_2$), 3.80-3.90 (m, 4H, 2×OCH$_2$), 6.47-6.60 (m, 4H, C$_6$H$_4$), 6.70-6.80 (m, dH, C$_6$H$_4$). $^{29}$Si NMR (79 MHz, CDCl$_3$) δ −95.16 (s, Si(OCH$_2$CH$_2$NH$_2$)(OC$_6$H$_4$NH$_2$)$_3$); −90.59 (s, Si(OCH$_2$CH$_2$NH$_2$)$_2$(OC$_6$H$_4$NH$_2$)$_2$; −86.13 (s, Si(OCH$_2$CH$_2$NH$_2$)$_3$(OC$_6$H$_4$NH$_2$).

II. Synthesis of Examples of Polyaminosilicon Compounds of Type Formula

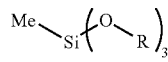

Example 6. Synthesis of 2,2',2"-((methylsilanetriyl)tris(oxy))triethanamine

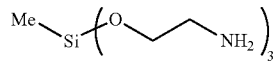

A 3-neck round-bottom-flask was equipped with a very efficient rectification column with a distillation condenser, a thermocouple and a heating mantle. The flask was charged with 120.2 g (1 mole) of trimethoxymethylsilane, 213.8 g of ethanolamine (3.5 moles). The reaction mixture was stirred at room temperature for 1-2 hours and the heating was gradually increased until boiling over 2-3 hours. Once distillation of low boiling components started, the heat was increased further until temperature of the flask reached ~150° C. while distilling off (82 g of distillate was collected). At this temperature, a vacuum of about 100 mmHg was then applied and heating was continued while distilling about and additional 15 g, and then the vacuum was changed to ~1-2 mmHg and a further 48 g of distillate was collected. When the temperature of distillation head reached ~100° C. @ 1-2 mmHg the title product was collected (recorded boiling point of 109° C. @ 1.2 mmHg) while keeping the pot temperature below 250° C. Yield of the product was 99 g (75% theoretical yield). $^{29}$Si NMR and $^1$H NMR conformed to structure. $^1$H NMR (400 MHz, CDCl$_3$) δ −0.19 (s, 3H, Si—CH$_3$), 0.94 (s, 6H, 3× NH$_2$), 2.43-2.46 (m, 6H, 3× NCH$_2$), 3.38-3.40 (m. 6H, 3×OCH$_2$). $^{29}$Si NMR (79 MHz, CDCl$_3$) δ −40.84 (s, SiCH$_3$).

Example 7. Synthesis of 2,2',2"-((methylsilanetriyl)tris(oxy))tris(propan-1-amine)

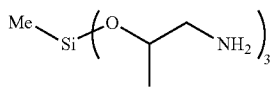

A 3-neck round-bottom-flask was equipped with a very efficient rectification column with a distillation condenser, a thermocouple and a heating mantle. The flask was charged with 360.7 g (3 moles) of trimethoxymethylsilane and 675 g of isopropanolamine (3.5 moles) containing ~10:1 ratio of 1-aminopropanol:2-aminopropanol. The reaction mixture was stirred at room temperature for 1-2 hours and the heating was gradually increased until boiling over 2-3 hours. Once distillation of low boiling components started, the heat was increased further until temperature of the flask reached ~150° C. while distilling off (208 g of distillate was collected). At this temperature vacuum of about 100 mmHg was applied and heating was continued while distilling and then the vacuum was changed to ~1-2 mmHg and a further distillate was collected. When the temperature of distillation head reached ~100° C. @ 1-2 mmHg the product was collected (recorded boiling point of 108° C. @ 0.4 mmHg) while keeping the pot temperature below 200° C. Yield of the product was 471 g (59% theoretical yield). $^{29}$Si NMR and $^1$H NMR conformed to structure. $^1$H NMR (400 MHz, CDCl$_3$) δ −0.50 (s, 3H, Si—CH$_3$), 0.49 (d, J=8.0 Hz, 9H, 3× CH$_3$) 0.56 (br, 6H, 3× NH$_2$), 1.19-2.00 (m, 6H, 3× CH$_2$), 3.27-3.31 (m, 3H, 3× CH). $^{29}$Si NMR (79 MHz, CDCl$_3$) δ −45.86. The products formed by reaction of trimethoxysilane with 2-aminopropanol appeared as <10% in the spectrum. $^1$H NMR (400 MHz, CDCl$_3$) δ −0.51 (s, Si—CH$_3$), 0.33 (d, J=6.4 Hz, CCH$_3$), 2.30-2.34 (m, CH), 2.73 (dd, J=7.2 Hz, 9.6 Hz, OCH$_2$), 2.94 (dd, J=4.4 Hz, 10 Hz, OCH$_2$). $^{29}$Si NMR (79 MHz, CDCl$_3$) δ −44.69.

Example 8. Synthesis of 1,1',1"-((methylsilanetriyl)tris(oxy))tris(propan-2-amine)

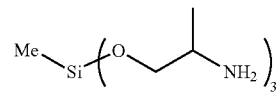

A 3-neck round-bottom-flask was equipped with a very efficient rectification column with a distillation condenser, a thermocouple and a heating mantle. The flask was charged with 272.4 g (2 moles) of trimethoxymethylsilane, 300.4 g of 2-amino-1-propanol (4 moles) and 0.5 g titanium (V) isopropoxide. The reaction mixture was stirred at room temperature for 1-2 hours and the heating was gradually increased until boiling over 2-3 hours. Once distillation of low boiling components started, the heat was increased further until temperature of the flask reached ~150° C. At this temperature, a vacuum was then applied, and heating was continued while distilling over 24 hours. When the temperature of distillation head reached ~100° C. @ 1-2 mmHg the product was collected (recorded boiling point of 106° C. @ 1.3 mmHg). Yield of the product was 258 g (49% theoretical yield). $^{29}$Si NMR and $^1$H NMR conformed to structure. $^1$H NMR (400 MHz, CDCl$_3$) δ −0.31 (s, 3H, Si—CH$_3$), 0.56 (d, J=6.4 Hz, 9H, 3× C≡CH$_3$), 0.88 (s, 6H, 3× NH$_2$), 2.52-2.60 (m, 3H, 3× CH), 2.94-3.00 (m, 3H, 3×OCH$_2$), 3.17-3.20 (m, 3H, 3×OCH$_2$). $^{29}$Si NMR (79 MHz, CDCl$_3$), δ −42.08.

Example 9. Synthesis of 1,1',1"-((methylsilanetriyl)tris(oxy))tris(butan-2-amine)

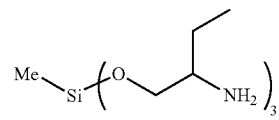

A 3-neck round-bottom-flask was equipped with a very efficient rectification column with a distillation condenser, a thermocouple and a heating mantle. The flask was charged with 240.4 g (1.75 moles) of trimethoxymethylsilane, 534.8 g of 2-amino-1-butanol (6 moles) and 0.5 g titanium (IV) isopropoxide. The reaction mixture was stirred at room temperature for 1-2 hours and the heating was gradually increased until boiling over 2-3 hours. Once distillation of low boiling components started, the heat was increased further until temperature of the flask reached ~150° C. At this temperature, a vacuum was applied, and heating was continued while distilling over 24 hours. When the temperature of distillation head reached ~100° C. @ 1-2 mmHg, the product was collected. $^{29}$Si NMR and $^1$H NMR conformed to structure. $^1$H NMR (400 MHz, CDCl$_3$) δ −0.41 (s, 3H, Si—CH$_3$), 0.38 (t, 9H, J=8.0 Hz, 3×CCH$_3$), 0.66-0.92 (m, 12H, 3× CH$_2$, 3× NH$_2$), 2.17-2.22 (m, 3H, 3× CH), 2.91 (dd, J=7.2 Hz, 9.6 Hz, 3H, 3×OCH$_2$), 3.15 (dd, J=4.0 Hz, 9.6 Hz, 3H, 3×OCH$_2$). $^{29}$Si NMR (79 MHz, CDCl$_3$) δ −42.00.

Example 10. Synthesis of 1,1',1"-((methylsilan-etriyl)tris(oxy))tris(2-methylpropan-2-amine)

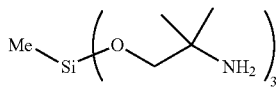

A 3-neck round-bottom-flask was equipped with a very efficient rectification column with a distillation condenser, a thermocouple and a heating mantle. The flask was charged with 272.4 g (2 moles) of trimethoxymethylsilane, 534.8 g of 2-amino-2-methylpropanol (6 moles) and 0.5 g titanium (IV) isopropoxide. The reaction mixture was stirred at room temperature for 1-2 hours and the heating was gradually increased until boiling over 2-3 hours. Once distillation of low boiling components started, the heat was increased further until temperature of the flask reached ~150° C. At this temperature, a vacuum was applied, and heating was continued while distilling over 24 hours. When the temperature of distillation head reached ~100° C. @ 1-2 mmHg the product was collected. $^{29}$Si NMR and $^1$H NMR conformed to structure. $^1$H NMR (400 MHz, CDCl$_3$) δ −0.16 (s, 3H, Si—CH$_3$), 0.75 (s, 18H, 6× CH$_3$), 0.91 (s, 6H, 3× NH$_2$), 3.14 (s, 6H, 3× OCH$_2$). $^{29}$Si NMR (79 MHz, CDCl$_3$) δ −42.42 (s).

Example 11. Synthesis of 4,4'(((1-aminopropan-2-yl)oxy))(methyl)silanediyl)bis(oxy))dianiline

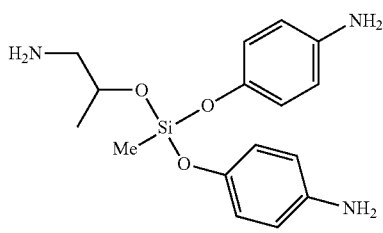 [SMILES: CC(CN)O[Si](C)(Oc1ccc(N)cc1)Oc1ccc(N)cc1]

A 3-neck round-bottom-flask was equipped with a very efficient rectification column with a distillation condenser, a thermocouple and a heating mantle. The flask was charged with 265.4 g (1 mole) of 2,2',2"-((methylsilanetriyl)tris (oxy))tris(propan-1-amine), and 218.3 g (2 moles) of 4-aminophenol. The reaction mixture was stirred at room temperature for 1-2 hours and heating was gradually increased until boiling over 2-3 hours. Once distillation of low boiling components started, the heat was increased further until temperature of the flask reached ~150° C. At this temperature vacuum was applied and heating was continued while distilling over 24 hours until the theoretical amount of isopropanolamine was distilled off (150 g). The title product was collected from the reaction flask. $^{29}$Si NMR and $^1$H NMR conformed to structure comprising of a 2:3:1 mixture of compounds Si(CH$_3$)(OC$_6$H$_4$NH$_2$)$_3$, Si(CH$_3$)(OC$_6$H$_4$NH$_2$)$_2$(OCH(CH$_3$)CH$_2$NH$_2$), and Si(CH$_3$)(OCH(CH$_3$)CH$_2$NH$_2$)$_3$. $^1$H NMR (400 MHz, CDCl$_3$) δ 0.20-0.40 (m, 3H, SiCH$_3$), 1.10-1.30 (m, 3H, CCH$_3$), 2.50-2.70 (m, 2H, NCH$_2$), 3.15-3.60 (br, 6H, NH$_2$), 4.00-4.20 (m, 1H, CH), 6.49-6.52 (m, 4H, ArH), 6.73-6.75 (m, 4H, ArH). $^{29}$Si NMR (CDCl$_3$) δ −51.19 (s, Si(CH$_3$)(OC$_6$H$_4$NH$_2$)$_3$; −49.08 (s, Si(CH$_3$)(OC$_6$H$_4$NH$_2$)$_2$(OCH(CH$_3$)CH$_2$NH$_2$); −45.71 (s, Si(CH$_3$)(OCH(CH$_3$)CH$_2$NH$_2$)$_3$.

III. Synthesis of Examples of Polyaminosilicon Compounds of Type Formula

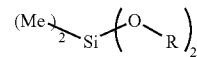

Example 12. Synthesis of 2,2'-((dimethylsilanediyl)bis(oxy))diethanamine

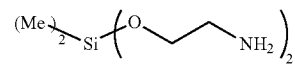

A 3-neck round-bottom-flask was equipped with a very efficient rectification column with a distillation condenser, a thermocouple and a heating mantle. The flask was charged with 60 g (0.5 mole) of dimethoxydimethysilane, 62.5 g (1.025 moles) of ethanolamine and 1 g sodium methanolate (30% in methanol). The reaction mixture was stirred at room temperature for 5 minutes and became homogeneous. The heating was gradually increased until boiling over 2-3 hours. Once distillation of low boiling components started, the heat was increased further until temperature of the flask reached ~150° C. At this temperature vacuum was applied and heating was continued while distilling product at 116° C. @ 20 mmHg. $^{29}$Si NMR and $^1$H NMR conformed to structure. $^1$H NMR (400 MHz, CDCl$_3$) δ 0.04 (s, 6H, Si(CH$_3$)$_2$, 0.78 (s, 4H, 2× NCH$_2$), 2.27-2.31 (br s, 4H, 2× NH$_2$), 3.20-3.31 (br s, 4H, OCH$_2$). $^{29}$Si NMR (CDCl$_3$) δ −1.97 (s).

Example 13. Synthesis of 2,2'-((dimethylsilanediyl)bis(oxy))bis(propan-1-amine)

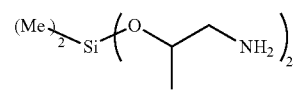

A 3-neck round-bottom-flask was equipped with a very efficient rectification column with a distillation condenser, a thermocouple and a heating mantle. The flask was charged with 240.5 g (2 moles) of dimethyldimethoxysilane, 301 g of isopropanolamine (4 moles) and 0.5 g titanium (IV) isopropoxide. The reaction mixture was stirred at room temperature for 1-2 hours and the heating was gradually increased until boiling over 24 hours. Once distillation of low boiling components started, the heat was increased further until temperature of the flask reached ~150° C. At this temperature vacuum was applied and heating was continued while distilling over 24 hours. When the temperature of distillation head reached ~80° C. @ 1-2 mmHg, the product was collected (recorded boiling point of 83° C. @ 3 mmHg). Yield of the product was 80 g (19% theoretical yield). $^{29}$Si NMR and $^1$H NMR conformed to structure comprising of a 1:1 mixture of diastereoisomers: $^1$H NMR (400 MHz, CDCl$_3$) δ −0.26 (s, 6H, Si(CH$_3$)$_2$, 0.73-0.79 (m, 6H, 2×CCH$_3$), 2.16-2.26 (m, 4H, 2× CH$_2$), 3.46-3.50 (m, 2H, 2× CH). $^{29}$Si NMR (79 MHz, CDCl$_3$) δ −5.89 (s), −5.92 (s). The isopropanolamine used in the reaction contained 1-aminopropanol:2-aminopropanol in 10:1 ratio. The products formed by the reaction of dimethyldimethoxysilane with 1-aminopropanol showed <10% in the spectrum. $^1$H NMR (400 MHz, CDCl$_3$) δ 0.60 (s, Si(CH$_3$)$_2$), 2.56-2.57 (m, CCH$_3$)), 2.90-2.94 (m, CH), 3.10-3.20 (m, OCH$_2$)$_2$$^9$Si NMR (79 MHz, CDCl$_3$) δ -4.26 (s).

Example 14. Synthesis of 1,1'-((dimethylsilanediyl)bis(oxy))bis(propan-2-amine)

A 3-neck round-bottom-flask was equipped with a very efficient rectification column with a distillation condenser, a thermocouple and a heating mantle. The flask was charged with 240.5 g (2 moles) of dimethyldimethoxysilane, 450 g of 2-aminopropanol (6 moles) and 3 g titanium (IV) isopropoxide. The reaction mixture was stirred at room temperature for 1-2 hours and the heating was gradually increased until boiling over 24 hours. Once distillation of low boiling components started, the heat was increased further until temperature of the flask reached ~150° C. At this temperature, a vacuum was applied, and heating was continued while distilling over 24 hours. When the temperature of distillation head reached ~60° C. @ 1-2 mmHg, the product was collected (recorded boiling point of 62°-69° C. @ 2 mmHg). $^{29}$Si NMR and $^1$H NMR conformed to structure. $^1$H NMR (400 MHz, CDCl$_3$) δ 0.04 (s, 6H, Si(CH$_3$)$_2$), 0.93 (s, 6H, 2× CCH$_3$), 1.24 (br s, 4H, 2× NH$_2$), 2.88-2.93 (m, 2H, 2×NCH), 3.22-3.27 (m, 2H, OCH$_2$). 3.47-3.51 (m, 2H, OCH$_2$). $^{29}$Si NMR (79 MHz, CDCl$_3$) δ -2.63 (s).

Example 15. Synthesis of 1,1'-((dimethylsilanediyl)bis(oxy))bis(butan-2-amine)

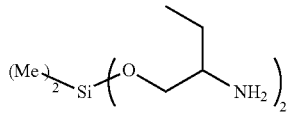

A 3-neck round-bottom-flask was equipped with a very efficient rectification column with a distillation condenser, a thermocouple and a heating mantle. The flask was charged with 296.6 g (2 moles) of dimethyldiethoxysilane, 450 g of 2-aminobutanol (6 moles) and 3 g titanium (IV) isopropoxide. The reaction mixture was stirred at room temperature for 1-2 hours and the heating was gradually increased until boiling over 24 hours. Once distillation of low boiling components started, the heat was increased further until temperature of the flask reached ~150° C. At this temperature, a vacuum was applied, and heating was continued while distilling over 24 hours. When the temperature of distillation head reached ~80° C. @ 1-2 mmHg, the product was collected (recorded boiling point of 880° C.-92° C. @ 1.5 mmHg). $^{29}$Si NMR and $^1$H NMR conformed to structure. $^1$H NMR (400 MHz, CDCl$_3$) δ 0.04 (s, 6H, Si((CH$_3$)$_2$), 0.84 (t, J=7.2 Hz, 6H, 2×CCH$_3$), 1.10-1.37 (m, 8H, 2×CCH$_2$, 2× NH$_2$), 2.63-2.67 (m, 2H, 2×NCH), 3.27-3.31 (m, 2H, OCH$_2$), 3.53-3.57 (m, 2H, OCH$_2$). $^{29}$Si NMR (79 MHz, CDCl$_3$) δ -2.48 (s).

Example 16. Synthesis of 1,1'-((dimethylsilanediyl)bis(oxy))bis(2-methylpropan-2-amine)

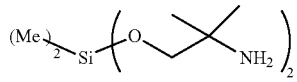

A 3-neck round-bottom-flask was equipped with a very efficient rectification column with a distillation condenser, a thermocouple and a heating mantle. The flask was charged with 240.5 g (2 moles) of dimethyl dimethoxysilane, 356.5 g of 2-amino-2-methylpropanol (4 moles) and 3 g titanium (IV) isopropoxide. The reaction mixture was stirred at room temperature for 1-2 hours and the heating was gradually increased until boiling over 24 hours. Once distillation of low boiling components started, the heat was increased further until temperature of the flask reached ~150° C. At this temperature, a vacuum was applied, and heating was continued while distilling over 24 hours. When the temperature of distillation head reached ~60° C. @ 1-2 mmHg, the product was collected (recorded boiling point of 63° C. @ 3 mmHg). $^{29}$Si NMR and $^1$H NMR conformed to structure. $^1$H NMR (400 MHz, CDCl$_3$) δ 0.00 (s, 6H, Si(CH$_3$)$_2$), 0.93 (s, 12H, 2× C(CH$_3$)$_2$), 1.14 (br s, 4H, 2× NH$_2$), 3.25 (s, 4H, 2× CH$_2$). $^{29}$Si NMR (CDCl$_3$) δ -2.76 (s).

IV. Qualification of "Usability" of Polyamino Silicon Compounds for General Epoxy Applications Polyamines such as ethyleneamines, polyetheramines, aromatic amines, and cycloaliphatic amines are commonly used as epoxy curing agents in industrial applications. The selection of a particular polyamine hardener is usually a reflection of the need to balance both processing conditions and the physical properties required of the final epoxy-based, or epoxy-containing product. The blending of such conventional polyamines allows the formulator to create different epoxy compositions, spanning a wide processing range; e.g., from slow curing compositions with long working times to fast curing composition with shorter working times; and final properties, e.g., from lower T$_g$ (i.e., <90 C) to higher T$_g$ (<150 C). In general, such polyamines have good "usability," meaning that they can be exposed to the ambient environment {prior to curing} for varied periods of times, without detriment. Nevertheless, the reaction of amino compound with carbon dioxide in the ambient is known in the art as "amine blush". This process is more prevalent with polyamine compounds that have higher reactivity. In general, the trend for amine blush is: ethyleneamine>cycloaliphatic amine >polyetheramine >>aromatic amine. The practical consequence of this is that polyamines with a greater propensity for amine blush are used more minimally in applications that entail long exposure of the epoxy composition {prior to curing} to the ambient environment (e.g., such as coatings, and wet-layup). The usability to polyamines is less of an issue in situations where mixing of the epoxy composition is done in a "closed" system and application/curing of the composition is isolated from the environment during curing (e.g., preparation of a composite in a mold).

Polyaminosilicon compounds are subject to amine blush by virtue of containing NH$_2$ groups. However, as disclosed in this invention polyaminosilicon cross-linking agents are also subject to an additional decomposition pathway, presumably by virtue of containing hydrolyzable Si—O bonds. In aspect, it is the hydrolyzable Si—O bonds that enable cured epoxy compositions containing polyaminosilanes to be recyclable. In another aspect, polyaminosilicon compounds that provide recyclability of the cured epoxy composition, but also have extended usability are preferred.

It has been found that upon standing in the ambient air, a crust may form on the surface of the polyaminosilicon compounds. This crust that we refer to herein as a "skin," presumably occurs via hydrolysis of the polyaminosilicon compound with ambient moisture in the air, leading to release of amino alcohol and the formation of a polysiloxane (eq 1). FIG. 1 illustrates how the skinning effect is dependent on the molecular structure of the polyaminosilicon compound.

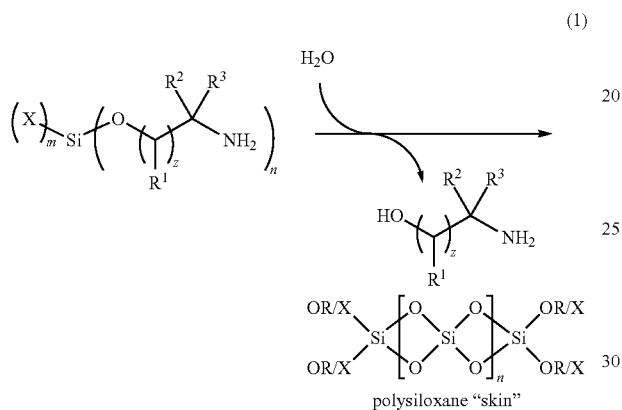

(1)

If the rate of this PASi decomposition the ambient environment can be managed, then PASi compounds can serve to expand the application horizon of recyclable epoxy technology beyond the scope of polyaminoacetals as recently described (for example, as described in U.S. Pat. Nos. 9,631,049 and 9,862,797). To understand the structural activity relationship on usability of PASi molecules in the ambient, the rate of skin formation was measured for various PASi compounds.

Example 17. General Procedure for Measuring PASi Skin Formation 10 g of the PASi compound was weighed into a 3" diameter aluminum weigh dish, at ambient temperature and humidity, and the "skin formation time" was determined, wherein the skin formation time is defined by the time it takes for at least 10% of the surface to be crusted over. The results for different PASi compounds is provided in Table 1.

TABLE 1

The rate of polysiloxane skin formation after pouring.

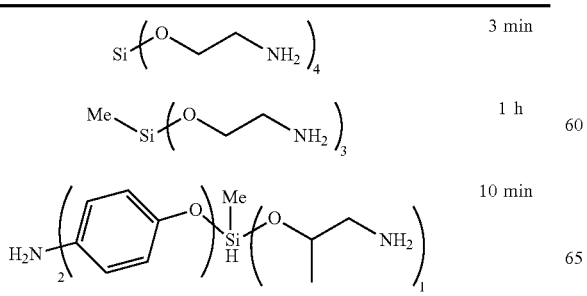

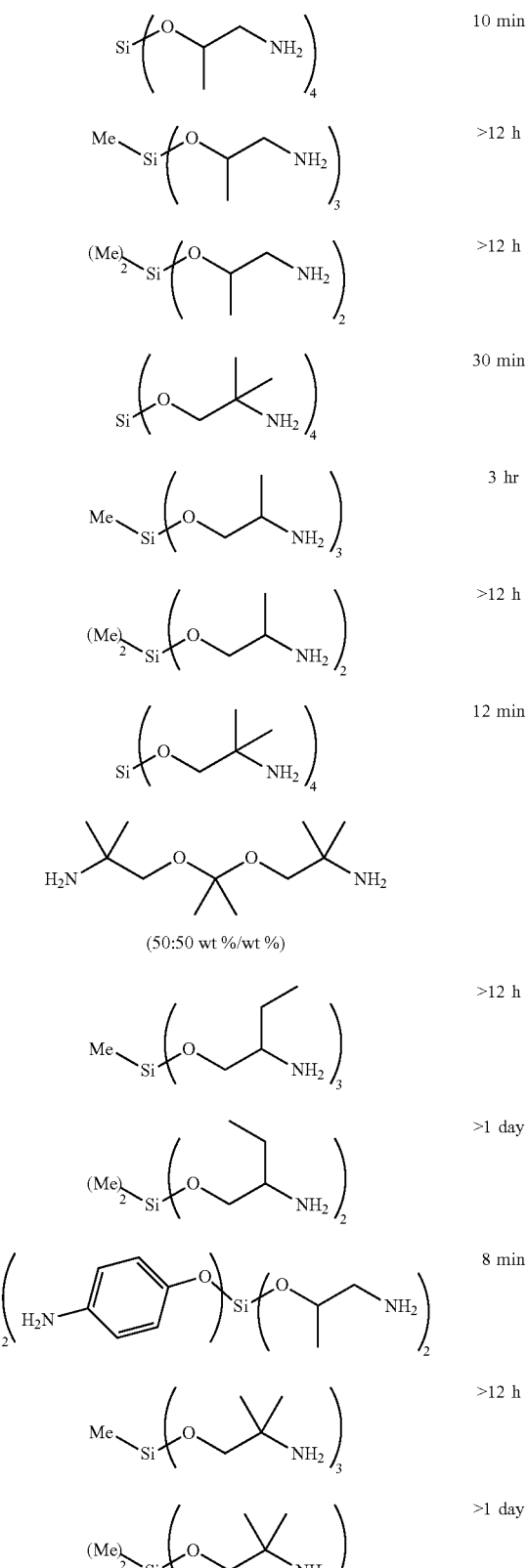

TABLE 1-continued

The rate of polysiloxane skin formation after pouring.

(H₂N-C₆H₄-O)₂-Si-(O-CH(CH₃)-CH₂-NH₂)₂ : 20 min

H₂N-CH₂-CH₂-O-C(CH₃)-O-CH₂-CH₂-NH₂ :

H₂N-CH₂-CH(OH)-CH₃

(71:24:5 wt %/wt %/wt %)

(H₂N-C₆H₄-O)₁.₅-Si(Me)(H)-(O-CH₂-CH₂-NH₂)₁.₅  6 min (H₂N-C₆H₄-O)₂-Si(Me)(H)-(O-CH(CH₃)-CH₂-NH₂)₁ : 20 min

H₂N-CH₂-CH₂-O-C(CH₃)-O-CH₂-CH₂-NH₂ :

H₂N-CH₂-CH(OH)-CH₃

(71:24:5 wt %/wt %/wt %)

As the data in Table 1 reveals, the rate of skin formation is dependent on two factors: 1) the number of —OR groups on the central silicon atom; and 2) the steric hindrance around the central silicon atom. Notably, the former appears to most important as it was discovered that aminosilanes having at least one Si—CH₃ group have much higher stability towards the moisture in the air than tetraamino orthosilicates, e.g., the skin formation rate:

$$\text{Si}\left(\text{O-C}(R^2)(R^3)_z\text{-NH}_2\right)_4 \gg \text{Me-Si}\left(\text{O-C}(R^2)(R^3)_z\text{-NH}_2\right)_3 \approx \text{(Me)}_2\text{Si}\left(\text{O-C}(R^2)(R^3)_z\text{-NH}_2\right)_2 \quad (2)$$

Consequently, for open use epoxy applications, the attenuated skin formation on PASi compounds that contain a silicon carbon bond and have better usability than PASi compounds that contain only Si—O bonds.

V. Epoxy Compositions Containing Polyaminosilicon Compounds and their Properties General. For the purposes of comparison, a general purpose epoxy resin (Super Sap 300; EEW=188; Entropy Resins, Inc) was used as the epoxy resin for all entries, unless otherwise noted. The mix ratio of hardener, or formulation of hardeners, was determined by balancing the amine equivalent weight (or AEW) with the epoxide equivalent weight (or EEW) of the resin. Typically, the resin and hardener were mixed for 2-5 minutes using a speed mixer, and then cast and cured as appropriate. For chemical resistance, glass transition temperature (Tg), and recycling experiments, the epoxy composition was cast into 3" diameter aluminum weighing dishes and cured to yield 20 g epoxy disks. The standard cure profile used was: room temperature (overnight or until epoxy setting), then 125° C. for 3 hours. For mechanical properties the epoxy composition was cast into a mold according to ASTM standards.

Example 18. Glass Transition Temperature of Polyaminosilicon Containing Epoxy Compositions In an aspect, this invention discloses the use of certain polyamino silicon compounds, and blends of polyaminosilicon compounds with polyaminoacetals and amino alcohols, as curing agents for epoxy resins, to create recyclable epoxy compositions. In yet another aspect, while the epoxy compositions are recyclable under certain set of conditions, compositions may be created that possess satisfactory $T_g$ values, e.g., they provide a similar $T_g$ value range as do non-recyclable epoxy compositions created from liquid, polyamine curing agents.

This example demonstrates, vis-a-via the $T_g$ values of non-limiting examples of polyaminosilicon containing epoxy compositions in Table 2 and Table 3, that a wide range of $T_g$ values are achievable.

TABLE 2

Glass transition of general epoxy resin cured with polyamiosilicon compounds

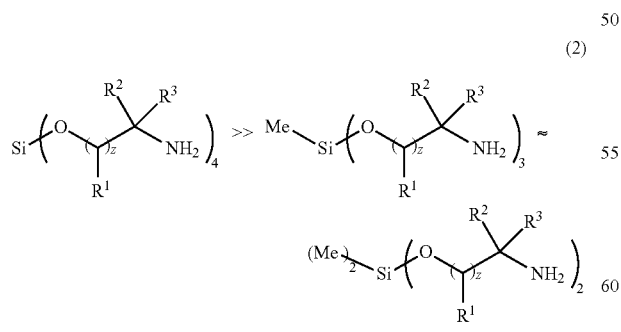

| Curing Agent | $T_g$ |
|---|---|
| Si(O-CH₂-CH₂-NH₂)₄ | 124° C. |
| Me-Si(O-CH₂-CH₂-NH₂)₃ | 105° C. |
| (H₂N-C₆H₄-O)₂-Si-(O-CH(CH₃)-CH₂-NH₂)₁ | 152° C. |
| Si(O-CH(CH₃)-CH₂-NH₂)₄ | 126° C. |
| Me-Si(O-CH(CH₃)-CH₂-NH₂)₃ | 117° C. |
| (Me)₂-Si(O-CH(CH₃)-CH₂-NH₂)₂ | 92° C. |

TABLE 2-continued

Glass transition of general epoxy resin cured with polyamiosilicon compounds

| Curing Agent | $T_g$ |
|---|---|
| 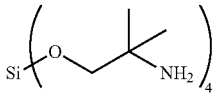 | 134° C. |
| 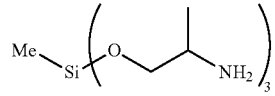 | 116° C. |
| 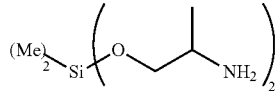 | 77° C. |
| 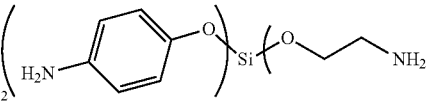 | 147° C. |
| 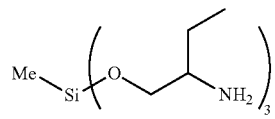 | 116° C. |

TABLE 2-continued

Glass transition of general epoxy resin cured with polyamiosilicon compounds

| Curing Agent | $T_g$ |
|---|---|
| 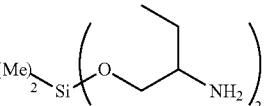 | 92° C. |
| 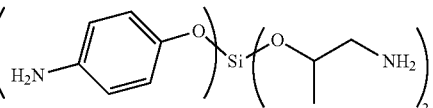 | 140° C. |
| 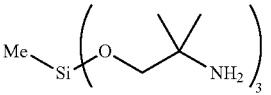 | 126° C. |
| 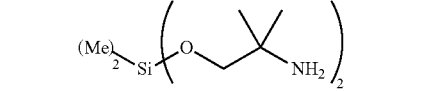 | 101° C. |
| 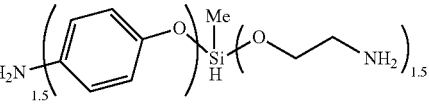 | 130° C. |

TABLE 3

Glass transition of general epoxy resin cured with blends of polyaminosilicon compounds and polyamioacetals and amino alcohols

| Polyaminosilicon (H1) | Polyaminoacetal (H2) | amino alcohol (H3) | H1:H2:H3 (wt Ratio) | Glass Transition Temperature (° C.) |
|---|---|---|---|---|
| 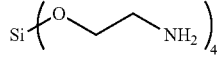 | — | ethanolamine | 66:12 | 120 |
| 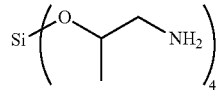 |  | — | 61:50 | 115 |
| 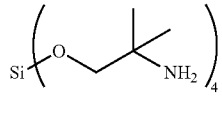 |  | — | 50:50 | 125 |
| 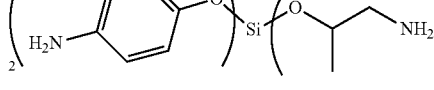 |  |  | 71:25:5 | 129 |
| 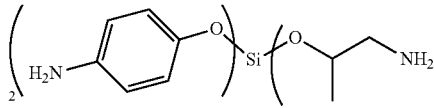 | 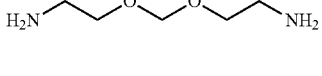 | — | 75:25 | 129 |
| 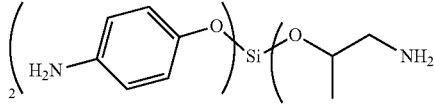 | 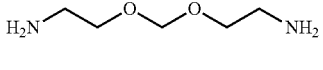 | — | 50:50 | 117 |

TABLE 3-continued

Glass transition of general epoxy resin cured with blends of polyaminosilicon compounds and polyamioacetals and amino alcohols

| Polyaminosilicon (H1) | Polyaminoacetal (H2) | amino alcohol (H3) | H1:H2:H3 (wt Ratio) | Glass Transition Temperature (° C.) |
|---|---|---|---|---|
| (H2N-C6H4-O)2-Si-(O-CH(CH3)-CH2-NH2)2 | H2N-CH2CH2-O-CH2-O-CH2CH2-NH2 | — | 25:75 | 110 |
| (H2N-C6H4-O)2-Si-(O-CH(CH3)-CH2-NH2)2 | H2N-CH2CH2-O-C(CH3)2-O-CH2CH2-NH2 | — | 75:25 | 119 |
| (H2N-C6H4-O)2-Si-(O-CH(CH3)-CH2-NH2)2 | H2N-C(CH3)2-CH2-O-C(CH3)2-O-CH2-C(CH3)2-NH2 | HO-CH(CH3)-CH2-NH2 | 71:25:5 | 133 |

Example 19. Mechanical Properties of Epoxy Compositions

In an aspect, this invention discloses the use of certain polyaminosilicon compounds, and blends of polyaminosilicon compounds with polyaminoacetals and amino alcohols, as curing agents for epoxy resins, to create recyclable epoxy compositions. In yet another aspect, while the epoxy compositions are recyclable under certain set of conditions, compositions may be created that possess satisfactory mechanical properties, e.g., they provide a similar mechanical property as do non-recyclable epoxy compositions created from liquid, polyamine curing agents.

This example demonstrates, the mechanical properties of non-limiting examples of polyaminosilicon containing epoxy compositions in Table 4.

TABLE 4

Mechanical properties of epoxy resin cured with different polyaminosilicon containing hardener formulations

| | Tensile Properties[1] | | | Flexural Properties[2] | |
|---|---|---|---|---|---|
| Curing Agent | strength/ psi | % elongation | modulus/ psi | strength/ psi | modulus/ psi |
| Me-Si-(O-CH2CH2-NH2)3 | 9,495 | 6.20 | 388,224 | 15,997 | 401,326 |
| Me-Si-(O-CH(CH3)-CH2-NH2)3 | 9,590 | 5.70 | 398,715 | 15,423 | 405,604 |
| Me-Si-(O-CH2-CH(CH3)-NH2)3 | 5,527 | 1.60 | 409,477 | 18,002 | 430,733 |
| Me-Si-(O-CH2-CH(Et)-NH2)3 | 5,673 | 1.60 | 411,222 | 15,909 | 407,487 |
| Me-Si-(O-CH2-C(CH3)2-NH2)3 | — | — | — | 19,186 | 415,298 |
| (H2N-C6H4-)1.5(-O-Si(Me)(H)-O-CH2CH2-NH2)1.5 | 11,790 | 6.10 | 457,127 | 20,488 | 434,238 |

TABLE 4-continued

Mechanical properties of epoxy resin cured with different polyaminosilicion containing hardener formulations

| Curing Agent | Tensile Properties[1] | | | Flexural Properties[2] | |
| --- | --- | --- | --- | --- | --- |
| | strength/ psi | % elongation | modulus/ psi | strength/ psi | modulus/ psi |
| [structure 1] | 9,704 | 3.40 | 472,659 | 26,146 | 894,179 |
| [structure 2] (65:35 wt/wt) | 7,490 | 2.2 | 492,700 | — | — |
| [structure 3] (75:25 wt/wt) | 8,230 | 2.5 | 499,400 | — | — |
| [structure 4] (75:25 wt/wt) | 8,140 | 2.1 | 528,520 | — | — |
| [structure 5] (75:25 wt/wt) | 8,220 | 2.4 | 502,520 | — | — |
| [structure 6] (71:24:5 wt/wt/wt) | 10,810 | 4.3 | 515,480 | — | — |

TABLE 4-continued

Mechanical properties of epoxy resin cured with different polyaminosilicion containing hardener formulations

| Curing Agent | Tensile Properties[1] | | | Flexural Properties[2] | |
|---|---|---|---|---|---|
| | strength/ psi | % elongation | modulus/ psi | strength/ psi | modulus/ psi |
| (H₂N–C₆H₄–O)₂Si(O–CH(CH₃)–CH₂–NH₂)₂ : H₂N–CH₂CH₂–O–C(CH₃)₂–O–CH₂CH₂–NH₂ : H₂N–CH(CH₃)–CH₂OH (71:24:5 wt/wt/wt) | 8,060 | 2.2 | 460,420 | — | — |

[1]Tensile properties determined according to ASTM D638, on fully cured (>98% cure) epoxy compositions.
[2]Flexural properties determined according to ASTM D790, on fully cured (>98% cure) epoxy compositions.

Example 20. Fast Curing Epoxy Formulations

The wide-scale adoption of composites for automotive applications will be contingent on effective cost-reduction strategies. The advent High Pressure Resin Transfer Molding (HP-RTM), and other advanced manufacturing processes has helped move the thermoset composite industry towards this goal, enabling composite part cycle times of minutes. Key to HP-RTM is the precise mixing and injection of the epoxy composition into a heated mold containing the fabric (e.g. fiberglass; e.g., carbon fiber). An ideal epoxy composition would set only after the fabric is infused, and then develop $T_g$ rapidly until it is fully cured (i.e., >97% cured). Then the composite part demolded from the press (while still hot) and then the next part fabricated. It should be noted, that the $T_g$ values obtained from such a rapid curing process are usually lower by 10° C. or more, relative to when the epoxy composition is set and cured under a slower and more gradual temperature ramp profile. Today, state of the art, non-recyclable, HP-RTM epoxy compositions, develop >98% cure in 1-5 minutes at mold temperatures in the range of 100-140° C. With regard to $T_g$ values, a specification of >95° C. is acceptable, provided that the part is not located near an internal combustion area.

This example serves to demonstrate that epoxy compositions of this invention can be used to create fast curing, recyclable epoxy compositions suitable for use in the fabrication of composite parts. The demold $T_g$ values in Table 5 refers to a small sample (i.e., mg quantity) of epoxy composition cured in a differential scanning calorimeter, at different temperature and time intervals. This method tends to overestimate the time required to reach 98% cure, relative to the fabrication of actual composite parts, where there is a large mass of epoxy.

TABLE 5

Fast curing epoxy compositions and their Tg values after short curing cycles at elevated temperatures

| Polyaminosilicon (H1) | Polyaminoacetal (H2) | amino alcohol (H3) | H1:H2:H3 wt ratio | Resin | Demold $T_g$ (% cure) | |
|---|---|---|---|---|---|---|
| | | | | | 120° C./5 min | 140° C./5 min |
| (H₂N–C₆H₄–O)₂Si(O–CH(CH₃)–CH₂–NH₂)₂ | — | — | 100 | Super Sap 300 | 116° C. (96.6%) | 129° C. (99.4%) |
| (H₂N–C₆H₄–O)₂Si(O–CH(CH₃)–CH₂–NH₂)₂ | H₂N–CH₂CH₂–O–C(CH₃)₂–O–CH₂CH₂–NH₂ | HO–CH₂–CH(CH₃)–NH₂ | 75:25:5 | Epikote 6000 + 1 part IMR | 103° C. (97.6%) | 111° C. (99.1.%) |
| (H₂N–C₆H₄–O)₂Si(O–CH(CH₃)–CH₂–NH₂)₂ | H₂N–CH₂CH₂–O–CH₂–O–CH₂CH₂–NH₂ | HO–CH₂–CH(CH₃)–NH₂ | 75:25:5 | Epikote 6000 + 1 part IMR | 99° C. | 113° C. |

TABLE 5-continued

Fast curing epoxy compositions and their Tg values after short curing cycles at elevated temperatures

| Polyaminosilicon (H1) | Polyaminoacetal (H2) | amino alcohol (H3) | H1:H2:H3 wt ratio | Resin | Demold $T_g$ (% cure) 120° C./5 min | 140° C./ 5 min |
|---|---|---|---|---|---|---|
| (H2N-C6H4-O)2-Si(-O-CH(CH3)-CH2-NH2)2 | H2N-CH2-CH2-O-CH2-O-CH2-CH2-NH2 | — | 75:25 | Epikote 6000 + 1 part IMR | 94° C. | 109° C. |
| Si(-O-CH(CH3)-CH2-NH2)4 | — | — | 100 | Super Sap 300 | 97° C. (98%) | 108° C. (99.6%) |

IMR = internal mold release.

Example 21. Use of Epoxy Resin Compositions in HP-RTM to Create Composites and Comparison of Composite Mechanical Data with a Non-Recyclable Epoxy System Traditional resin transfer molding is a slow process. A fabric preform is prepared in advance and held to the final desired shape within a mold. A liquid polymer base is combined with a reactive agent and impregnated through the fabric preform typically with the aid of a pressurization system and vacuum. The final part may take hours or days to cure and may require the use of an autoclave to speed the process. However, HP-RTM is designed to impregnate the preform in seconds such that highly reactive polymer systems can be used and cured within minutes, with new systems approaching the minute cycle time regime: Material recipes based on epoxy have high potential to satisfy customers' increasing performance requirements, while fulfilling shorter part cycle times using rapid cure systems.

The HP-RTM schematic, shown in FIG. 2, depicts the equipment used to fabricate composite with the epoxy compositions of this inventions. Two reactive components (e.g. epoxy resin and polyamine curing agent formulation) are combined at high pressure (60-180 bar) and injected into a closed mold under vacuum at high flow rate (20-120 g/s). The recirculation components, in this case resin and hardener, operate at elevated temperature to reduce their viscosity and reduce thermal shock entering a hot tool. The high-pressure recirculation also prevents the water hammer effect due to sudden changes of pressure during injection. The third stream (not shown) is configured to run an internal mold release [IMR] injected into the resin stream during the mold filling.

Equipment used in the preparation of composites:
HP-RTM Line —RTM Rimstar Thermo 8/4/8 with 2 Mixing Heads
Internal mold release system can be used for third injection component
Precision dosing between 0.05-2.0 g/s
Mixing pressures between 60 and 180 bar
Resin flow rates: 20-120 g/s
Active pressure/flow monitoring
Hydraulic press—Dieffenbacher CompressPlus DCP-U 2500
Parallel motion control system
Maximum closing force of 25,000 kN (using full parallel motion control force)
Minimum closing force of 250 kN
Rapid motion up to 800 mm/s ram speed
Precision closing speeds up to 80 mm/s at low force and 20 mm/s at high force
Mold—Flat plaque mold with full fiber clamp
Center-fed fan gate injection inlet
Vacuum-assisted injection
Dimensions: 900×550 mm (inner area) [35.4×21.7 inches]
Adjustable part thickness 1.2-6.4 mm
Flexible tool platform using separate mold/manifold design
System Setup A 0.8 mm orifice was used for the resin. A 0.6 mm orifice was used for the hardener. Using these orifices the pressures at the mix head were set to be 120 bar. The pressures at the press were 1500 kN during the injection and 4500 kN during the curing for composite panels. Materials Two select, but non-limiting, polyaminosilicon containing curing agent formulations were used to create epoxy compositions used in the fabrication of fiberglass and carbon fiber composites. As a control, composite panels were also fabricated with a commercial epoxy system, at present used in HP-RTM composite applications and is non-recyclable. The IMR used for this example was Heloxy 112 (Hexion corporation). The resin used in this example was Epikote 6000 (Hexion corporation), a blend of bis A/F resins. The control resin composition is Hexion 6150 system. The resin tank was set to 60° C., then hardener and IMR tanks were set to 35° C. This example provides a specific, but non-limiting, illustration of use of polyaminosilicon containing epoxy compositions for the fabrication on composites, and recyclable composites. This invention is not limited by a particular composite manufacturing technique. This particular example illustrates the use of compositions in resin transfer molding, and specifically, high pressure resin transfer molding. However, the compositions described herein, could be used in other composites manufacturing techniques, such as, for example, pultrusion, filament winding, infusion, and the like.

TABLE 6

Epoxy compositions used to fabricate carbon and fiberglass composite using HP-RTM

| Composition | Polyaminosilicon (H1) | Polyaminoacetal (H2) | Amino alcohol (H3) | H1:H2:H3 wt ratio | Resin | PPW hardener: resin:IMR |
|---|---|---|---|---|---|---|
| 1 | (H2N-C6H4-O)2-Si-(O-CH(CH3)-CH2-NH2)2 | H2N-CH2CH2-O-C(CH3)2-O-CH2CH2-NH2 | HO-CH2-CH(NH2)-CH3 | 75:25:5 | Epikote 6000 | 24.5:100:1 |
| 2 | (H2N-C6H4-O)2-Si-(O-CH(CH3)-CH2-NH2)2 | H2N-CH2CH2-O-CH2-O-CH2CH2-NH2 | HO-CH2-CH(NH2)-CH3 | 75:25:5 | Epikote 6000 | 23.2:100:1 |
| Control | | Hexion 6150 system | | | | 24:100:1.2 |

PPW = part by weight

Both fiberglass and carbon fiber panels were fabricated. For fiberglass composites, a three-layer stack of U14EU970-01190-T2640-125000 (Saertex) or L120/07A12 M C3000/1012 (Owens Corning) unidirectional fabric was used. For carbon composites, carbon fiber fabric was obtained from SGL, already pre-formed: the unidirectional pre-form stack UD 1.2 ([0]$_6$ {300 gsm; dry thickness 2.2 mm; and the multidimensional pre-form stack MD 2 (+45, −45, 0, 0, −45, +45; dry thickness 2.1 mm; 0=600 gsm; T45=150 gsm).

Composite Panel Fabrication

The gel time of the compositions were recorded by collecting a sample from the mixing system and pouring a small sample directly on to the open, heated mold. The gel time is the time it takes the liquid composition to set, or the point at which resin flow has be arrested. The recorded gel time for Composition 1 was 52 sec and 27 sec, at mold temperatures of 120° C. and 140° C., respectively. The recorded gel time for Composition 2 was 42 sec and 36 sec, at mold temperatures of 130° C. and 140° C., respectively.

Table 7 provides, specific examples of processing profile conditions for the fabrication of fiberglass and carbon fiber composite panels. With press temperatures of 140° C., parts fabricated with Composition 1 & 2, could be demolded in as little as 1 minute. With press temperatures of 120° C., parts fabricated with Composition 1 & 2, could be demolded in as little as 2 minutes. Expectedly, longer cure times resulted in parts with a higher degree of cure. The majority of panel listed in table had a degree of cure >95% upon demold. As a control, UD 1.2 and MD 2 panels were also made using Hexion 6150 system.

TABLE 7

Selected examples composite panels fabricated using HP-RTM processing

| Part ID # | injection mass [g] | fiber type | injection speed [g/s] | Vacuum time [min] | injection pressure [bar] | Cure pressure [bar] | Press temp [° C.] | Cure time [min] |
|---|---|---|---|---|---|---|---|---|
| Recyclable Epoxy Composition 1 | | | | | | | | |
| 2 | 820 | glass | 60 | 1 | 1500 | 4500 | 120 | 5 |
| 3 | 840 | glass | 60 | 1 | 1500 | 4500 | 120 | 4 |
| 4 | 840 | glass | 60 | 1 | 1500 | 4500 | 120 | 3 |
| 5 | 840 | glass | 60 | 1 | 1500 | 4500 | 120 | 2 |
| 10 | 940 | glass | 60 | 1 | 1500 | 4500 | 140 | 2 |
| 11 | 940 | glass | 60 | 1 | 1500 | 4500 | 140 | 1.5 |
| 16 | 720 | MD 2 | 60 | 2 | 1500 | 4500 | 120 | 4 |
| 17 | 725 | UD 1.2 | 60 | 2 | 1500 | 4500 | 120 | 4 |
| 18 | 725 | MD 2 | 60 | 2 | 1500 | 4500 | 120 | 5 |
| 19 | 725 | UD 1.2 | 60 | 2 | 1500 | 4500 | 120 | 5 |
| 20 | 725 | MD 2 | 60 | 2 | 1500 | 4500 | 120 | 5 |
| 23 | 725 | UD 1.2 | 60 | 2 | 1500 | 4500 | 130 | 3 |
| 24 | 725 | MD 2 | 60 | 2 | 1500 | 4500 | 130 | 3 |
| 28 | 725 | MD 2 | 60 | 2 | 1500 | 4500 | 140 | 2 |
| 29 | 725 | UD 1.2 | 70 | 2 | 1500 | 5000 | 140 | 2 |
| 30 | 735 | MD 2 | 70 | 2 | 1500 | 5000 | 140 | 3 |
| 31 | 735 | UD 1.2 | 70 | 2 | 1500 | 5000 | 140 | 3 |
| 32 | 735 | MD 2 | 70 | 2 | 1500 | 5000 | 140 | 5 |
| 33 | 735 | UD 1.2 | 70 | 2 | 1500 | 5000 | 140 | 5 |
| Recyclable Epoxy Composition 2 | | | | | | | | |
| 37 | 735 | MD 2 | 70 | 2 | 1500 | 4500 | 130 | 5 |
| 38 | 735 | UD 1.2 | 70 | 2 | 1500 | 4500 | 130 | 5 |
| 39 | 725 | MD 2 | 70 | 2 | 1500 | 4500 | 130 | 3 |
| 40 | 725 | UD 1.2 | 70 | 2 | 1500 | 4500 | 130 | 3 |
| 41 | 725 | MD 2 | 70 | 2 | 1500 | 5000 | 140 | 2 |
| 42 | 725 | UD 1.2 | 70 | 2 | 1500 | 5000 | 140 | 2 |

TABLE 7-continued

Selected examples composite panels fabricated using HP-RTM processing

| Part ID # | injection mass [g] | fiber type | injection speed [g/s] | Vacuum time [min] | injection pressure [bar] | Cure pressure [bar] | Press temp [° C.] | Cure time [min] |
|---|---|---|---|---|---|---|---|---|
| 44 | 725 | UD 1.2 | 70 | 2 | 1500 | 5000 | 140 | 5 |
| 45 | 725 | MD 2 | 70 | 2 | 1500 | 5000 | 140 | 5 |
| Control Epoxy System | | | | | | | | |
| 47 | 725 | MD 2 | 50 | 1 | 1500 | 4500 | 120 | 5 |
| 48 | 735 | UD 1.2 | 50 | 1 | 1500 | 4500 | 120 | 5 |

Mechanical characterization of select UD 1.2 and MD 2 composites for Composition 1 (panel ID #32 & 33) and Composition 2 (panel ID #44 & 45), and compared against the non-recyclable control system (panel ID #47 & 48). The data obtained for tensile 90 according to the DIN EN 2597 test method and tensile 0° according to the DIN EN 2561 test method is provided in TABLE 8, demonstrating the recyclable Composition 1 & Composition 2 is at par with the non-recyclable epoxy control system. Tensile 90° properties we also compared after the immersion of the composite test specimens in solvents at room temperature for 7 Days. Noteworthy is the fact that even though Composition 1 and Composition 2 are recyclable under an acidic condition, the tensile properties of the UD 1.2 composites were not deteriorated after conditioning in acid solvents for 1 week.

TABLE 8

Tensile 0° and 90° property comparison of UD 1.2 carbon composite with and without solvent conditions

| | Control | | | Composition 2 | | | Composition 1 | | |
|---|---|---|---|---|---|---|---|---|---|
| | Tensile strength [MPa] | Failure strain | Modulus [MPa] | Tensile strength [MPa] | Failure strain | Modulus [MPa] | Tensile strength [MPa] | Failure strain | Modulus [MPa] |
| [1]Tensile 0° | | | | | | | | | |
| Average | 1403.5 | 0.0115 | 119784.0 | 1643.4 | 0.0139 | 112355.5 | 1465.8 | 0.0131 | 103190.7 |
| Std Dev | 71.9 | 0.0006 | 8059.6 | 97.8 | 0.0006 | 4587.7 | 42.1 | 0.0004 | 5307.4 |
| [2]Tensile 90° | | | | | | | | | |
| Average | 43.0 | 0.0048 | 9006.2 | 46.4 | 0.0048 | 9318.2 | 53.8 | 0.0068 | 8271.0 |
| Std Dev | 3.3 | 0.0007 | 626.9 | 6.1 | 0.0007 | 247.4 | 7.3 | 0.0012 | 448.4 |
| [2]Tensile 90° (Gasoline; 7 d immersion) | | | | | | | | | |
| Average | 50.8 | 0.0057 | 8871.4 | 57.2 | 0.0065 | 8976.7 | 56.6 | 0.0069 | 8296.8 |
| Std Dev | 4.2 | 0.0005 | 137.2 | 3.1 | 0.0005 | 374.5 | 3.2 | 0.0005 | 244.9 |
| [2]Tensile 90° (1% sulfuric acid; 7 d immersion) | | | | | | | | | |
| Average | 52.1 | 0.0064 | 8391.7 | 55.1 | 0.0064 | 8877.2 | 53.1 | 0.0067 | 8272.0 |
| Std Dev | 4.9 | 0.0007 | 122.4 | 6.4 | 0.0008 | 75.5 | 3.9 | 0.0007 | 472.7 |
| [2]Tensile 90° (%5 acetic acid; 7 d immersion) | | | | | | | | | |
| Average | 53.1 | 0.0064 | 8443.4 | 56.6 | 0.0065 | 8900.1 | 55.9 | 0.0071 | 8118.8 |
| Std Dev | 5.6 | 0.0008 | 217.9 | 3.9 | 0.0007 | 516.8 | 4.3 | 0.0008 | 263.2 |

[1]Test Method DIN EN 2561
[2]Test Method Din EN 2597

TABLES 9 provide a comparison of Compression, Flexural, and Shear properties according to ASTM or DIN test methods. The data reveals that Recyclable Compositions to be in some cases at par, or in some cases, superior to the state of the art, non-recyclable system.

TABLE 9

Compression 0° and 90° property comparison of UD 1.2 carbon composite

| | Control | | | Composition 2 | | | Composition 1 | | |
|---|---|---|---|---|---|---|---|---|---|
| | compress strength [MPa] | compress strain | Modulus [MPa] | compress strength [MPa] | compress strain | Modulus [MPa] | compress strength [MPa] | compress strain | Modulus [MPa] |
| | | | | [1]Compresion 0° | | | | | |
| Average | 581.7 | 0.0076 | 92977.2 | 682.3 | 0.0092 | 94547.6 | 557.4 | 0.0071 | 86115.0 |
| Std Dev | 55.1 | 0.0032 | 10410.5 | 37.0 | 0.0025 | 12226.3 | 44.2 | 0.0028 | 8023.2 |
| | | | | [1]Compresion 90° | | | | | |
| Average | 117.0 | 0.0101 | 9503.3 | 116.9 | 0.0170 | 7632.0 | 134.0 | 0.0179 | 8156.4 |
| Std Dev | 11.1 | 0.0095 | 769.9 | 4.6 | 0.0042 | 1956.4 | 12.8 | 0.0085 | 1326.2 |

[1]ASTM D 3410/D 3410M-03

TABLE 10

Flexural property comparison of MD 2 carbon composite at room temperature and elevated temperature

| | Control | | | Composition 2 | | | Composition 1 | | |
|---|---|---|---|---|---|---|---|---|---|
| | flexure strength [MPa] | elongation at break | flexure modulus [MPa] | flexure strength [MPa] | elongation at break | flexure modulus [MPa] | flexure strength [MPa] | elongation at break | flexure modulus [MPa] |
| | | | | [1]Flexure at room temperature | | | | | |
| Average | 728.2 | 0.0304 | 27471.3 | 717.2 | 0.0302 | 26492.8 | 771.9 | 0.0324 | 26735.7 |
| Std Dev | 31.4 | 0.0023 | 2553.2 | 41.2 | 0.0018 | 2175.5 | 50.2 | 0.0005 | 1833.1 |
| | | | | [1]Flexure at 80° C. | | | | | |
| Average | 529.9 | 0.0223 | 26533.2 | 316.8 | 0.0168 | 20892.3 | 446.3 | 0.0218 | 22649.8 |
| Std Dev | 10.8 | 0.0005 | 979.9 | 14.4 | 0.0003 | 745.6 | 18.8 | 0.0007 | 1119.9 |

[1]ASTM D 7264/D 7264M-07

TABLE 11

Short beam shear comparison of MD 2 composites

| | Control ILSS [MPa] | Composition 2 ILSS [MPa] | Composition 1 ILSS [MPa] |
|---|---|---|---|
| | [1]Testing at room temperature | | |
| Average | 51.13 | 50.67 | 50.92 |
| Std Dev | 1.71 | 2.04 | 1.44 |
| | [1]Testing at 80° C. | | |
| Average | 36.35 | 28.96 | 31.20 |
| Std Dev | 1.42 | 0.84 | 1.64 |

[1]ASTM D 2344/D 2344M-13

Example 22. Slow Curing Epoxy Compositions

Historically, certain epoxy composite manufacturing process have preferred epoxy compositions with long-working times (e.g. long pot-lifes, e.g. slower curing compositions) because the lay-up or infusion of fabrics in complex geometries, has been relatively timing consuming. Slower amine/epoxy reactivity is important in applications that require longer epoxy composition working times prior to curing (e.g., the infusion of a very large composite structures). Additionally, a mitigated or latent reactivity is important for manufacturing processes that require a large volume of the epoxy compositions to be used (e.g, pultrusion, e.g., filament winding), as the exotherm that develops in the resin bath will be less. Typically, if a process application requires the use of large volumes of epoxy composition (mixed resin+curing agent) and requires a resin bath working times of greater than 3-5 hr, then curing agents such as anhydrides are typically preferred over polyamine-based curing gents because the reactivity of the amino group with epoxy is too high. In an aspect, polyaminosilicon containing epoxy compositions, can be created with extended pot-lifes and working times, wherein the amine group reactivity is polyaminosicon is attenuated by steric hindrance.

Figure 3:
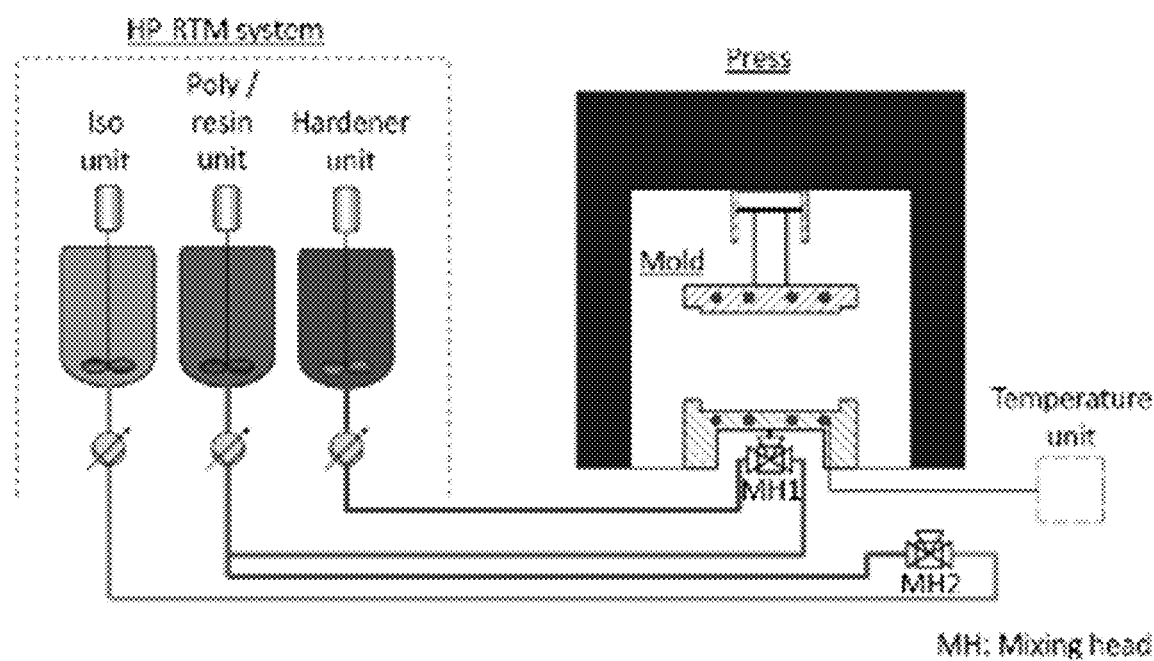
FIG. 3 depicts an exemplary schematic of HP-RTM used to manufacture composites with epoxy compositions.

This example demonstrates, vis-a-via the pot-life values of non-limiting examples of polyaminosilicon containing epoxy compositions in Table 12 that slow-curing epoxy compositions can be created. The pot-life values in the table corresponds to 100 g mass of resin+hardener at room temperature (20-23° C.). For comparison purposes, the pot-life of the widely used polyamine Jeffamine® D230 is also included in the table. Additionally, as working time is not solely related to the pot-life; it should be noted that certain compositions according to this invention demonstrate a slow build in mixed viscosity. For example, as illustrated in FIG. 3, the specific composition maintains a viscosity of <2000 cp for 2 hours at 25° C., and maintains a viscosity of <2000 cp for 4 hours at 35° C. The data in FIG. 3 was obtained with a 15 g mass using a Brookfield DV3 viscometer.

TABLE 12

Examples of slow curing epoxy compositions

| Polyamine Hardener Comparison | 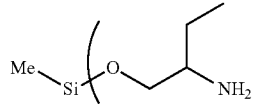 | 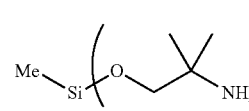 | 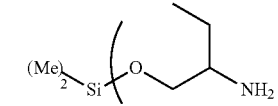 |
|---|---|---|---|
| AEW | 51.25 | 51.25 | 58.61 |
| PPH amine/100 part resin[2] | 27.26 | 27.26 | 31.17 |
| Pot Life, min (100 g mass, 21° C.) | >12 h | >24 h | >24 h |

[1] Jeffamine ® D -230

| Polyamine Hardener Comparison | 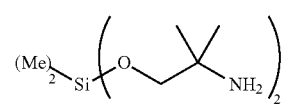 | 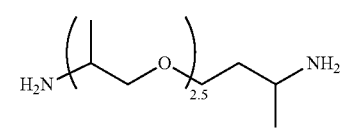 |
|---|---|---|
| AEW | 58.61 | 60 |
| PPH amine/100 part resin[2] | 31.17 | 32 |
| Pot Life, min (100 g mass, 21° C.) | 3 days | >4 h |

Example 23. Properties of Recycled Epoxy Products

Unlike thermoplastics, thermosetting plastics such as epoxies, are generally not recyclable. Cross-linking reactions that occur with conventional epoxies are essentially irreversible, which means the cross-linked materials cannot be re-melted and re-shaped without decomposition. Moreover, the cross-linked materials cannot be readily dissolved in most solvents. As a result, epoxy-based materials such as fiber reinforced epoxies or epoxy-based composite materials are generally not amenable to standard recycling practices. Thus, the epoxy matrix and fibers cannot be readily separated, and/or recovered. As result, such composite materials have historically been incinerated, land-filled, or ground and repurposed as filler material.

Figure 4:
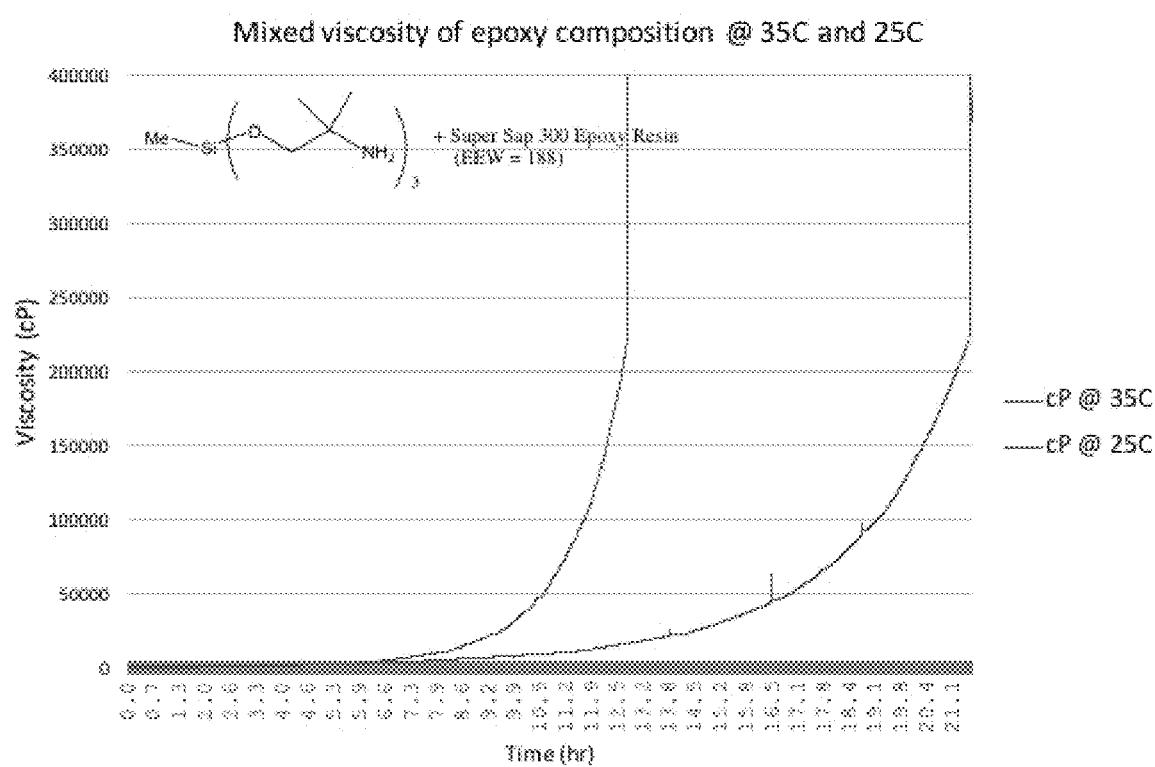
FIG. 4 depicts an example of a long working time recyclable epoxy composition.
Figure 5:
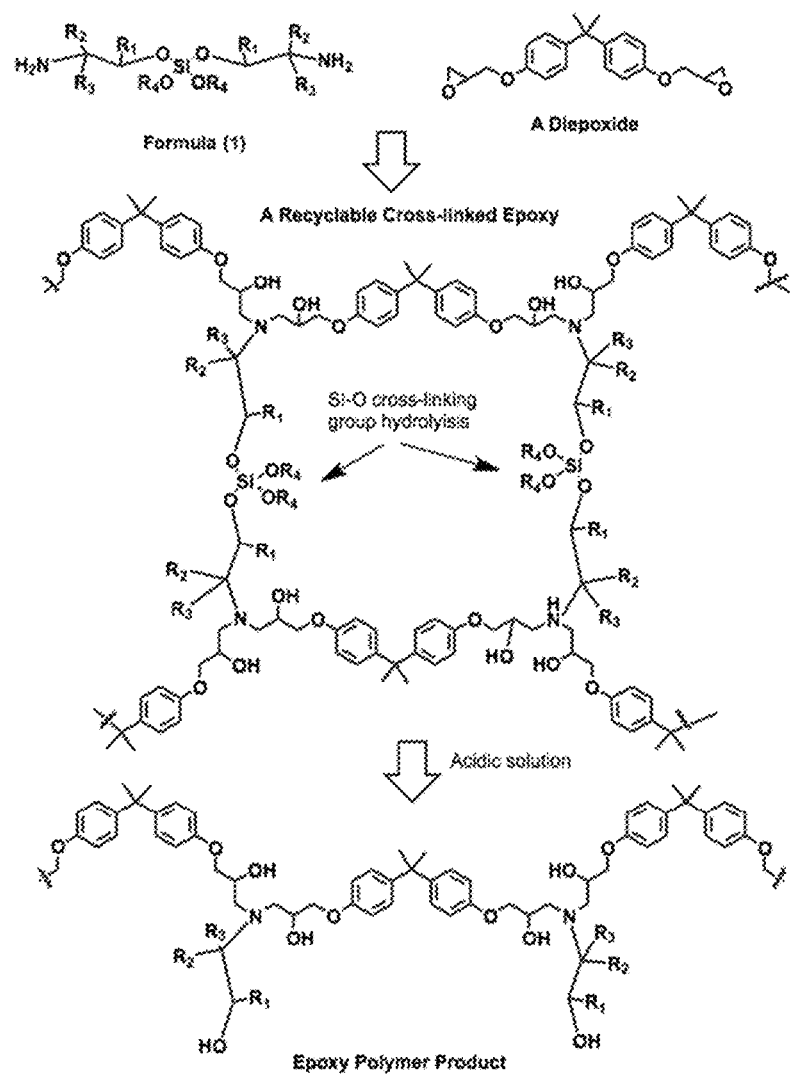
FIG. 5 depicts an exemplary recyclable epoxy composition example with polyamino Silicon cross-linker.
Figure 6:
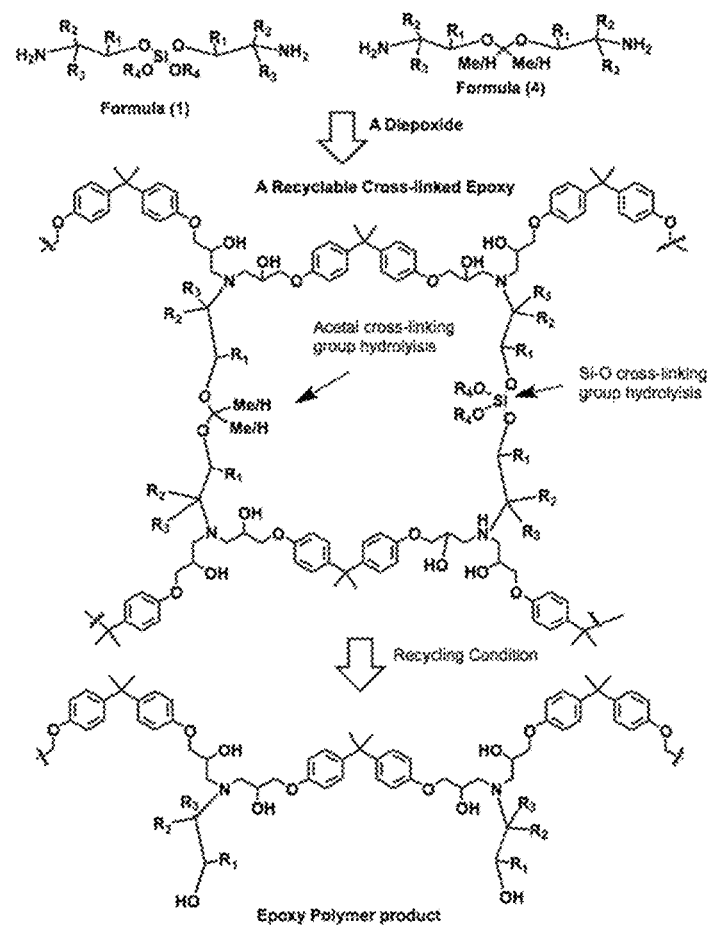
FIG. 6 depicts an exemplary recyclable epoxy composition example with polyamino silicon cross-linker and polyaminoacetal cross-linker.

However, epoxy resin compositions described herein are recyclable even when cross-linked. The reason for this is that cross-linking groups in the cross-linked epoxy polymers are cleavable by chemical means, e.g., including reaction with acid. The polyaminosilicon cross-linking agent described herein have at least two silicon-oxygen bonds that are susceptible to cleavage under hydrolytic conditions. Additionally, the polyaminosilicon cross-linking agent maybe be combined with an aliphatic polyamine cross-linking agent described herein (i.e. a polyaminoacetal), having at least one acetal or ketal group that is susceptible to cleavage under acidic conditions. Recyclable epoxy compositions may be created via the use of a polyaminosilicon cross-linking agent (FIG. 4) or the use of a combination of polyamino silicon cross-linking agent and polyaminoacetal cross-linking agent (FIG. 5), as the plurality of the cross-links in the thermoset matrix will be cleavable. Cross-linked epoxy polymers described herein contain these cleavable groups and therefore can be transformed for recycling purposes by hydrolytic treatment facilitated further with acid.

The intractability of cured epoxy resins, stemming primarily, from their highly cross-linked network that is characteristic of known cured epoxy resins is not an issue with the cured epoxy resins described herein. Cured epoxy resins described herein can result in composites with links in a three-dimensional network structure which can be cleaved under controlled conditions, resulting in disassembly of the three-dimensional network structure, and transformation of the thermoset into its polymeric or thermoplastic counterpart. The use of recyclable thermosetting compositions to make composites, provides a way to recover any articles, reinforcement materials and the like that were in cured composite material. Replacing conventionally used epoxy hardeners with cleavable cross-linking agents described herein effectively solves the present recycling problem associated with epoxy-based composites and materials, facilitates the disassembly of articles bonded together with epoxy glues, and would facilitate the removal and recovery of epoxy-based coatings.

Herein we define the term "recyclable epoxy" (or "recyclable epoxy composition") as a thermosetting composition containing at least an epoxy resin and a cross-linking agent (e.g curing agent; e.g., hardener) that after curing, may be converted into a thermoplastic epoxy, wherein the MW of the thermoplastic epoxy polymer is >1000. In order for the recoverable polymer to be most useful in applications, such as reconfiguration into thermoplastic part or thermoplastic composite part, it is preferable if the MW of the recoverable polymer is at least 10,000.

The use of 25 wt % acetic acid and optionally heat (Condition A) is one exemplary condition to convert the epoxy compositions of this invention into a thermoplastic polymer. For cure epoxy compositions that are less amenable to thermoset to thermoplastic conversion under Condition A, then the combination of DMSO, water, sulfuric acid and optionally heat (Condition B), is another condition. With the right balance of recycling solvent and temperature, it possible to cleave and also dissolve the epoxy composition according to this invention. Under this scenario, articles in contact with the recyclable epoxy composition will be released, and are recoverable. The resultant thermoplastic polymer in solution can then be further processed, if desired, by for example, stripping of the solution or, for example, obtained in powdered form via a precipitation process. The precipitated polymer, may be further dried, extruded into pellets, optionally compounded with other plastic and fibers, and then be used in thermoplastic applications e.g., injection molded, compression molded, extruded into a film, and the like. Table 13 provides some specific, but non-limiting, examples of the properties thermoplastic polymers obtained via the recycling of epoxy compositions of this invention. The thermoplastics were obtained in >95% yield via precipitation from the recycling solution via the addition of caustic and drying.

TABLE 13

Properties of recovered thermoplastic polymers derived from select recyclable epoxy compositions

| Curing agent | Recyclable Yes/No | Recycling Condition | Thermoplastic Tg (DSC) | [1]Thermoplastic MW (MW/MN) |
|---|---|---|---|---|
| Me–Si(–O–CH$_2$–CH$_2$–NH$_2$)$_3$ | Yes | A | 84° C. | nd |
| Si(–O–CH(CH$_3$)–CH$_2$–NH$_2$)$_4$ | Yes | A | 66° C. | 39,400 (2.76) |
| Me–Si(–O–CH$_2$–CH(CH$_3$)–NH$_2$)$_3$ | Yes | A | 94° C. | nd |
| Me–Si(–O–CH$_2$–CH(CH$_2$CH$_3$)–NH$_2$)$_3$ | Yes | A | 90° C. | nd |
| Me–Si(–O–CH$_2$–C(CH$_3$)$_2$–NH$_2$)$_3$ | Yes | A | 98° C. | 13,200 (2.24) |

[1] MW determined via GPC vs polystyrene standards
[2] nd: not determined.

Example 24. Chemical Resistance of Epoxy Compositions

In an aspect, this invention discloses the use of certain polyaminosilicon compounds, and blends of polyaminosilicon compounds with poly aminoacetals and amino alcohols, as curing agents for epoxy resins, to create recyclable epoxy compositions. In yet another aspect, while the epoxy compositions are recyclable under certain set of conditions, compositions may be created that possess satisfactory chemical resistance, making them suitable for application in general working environments (i.e. those that are not particularly extreme), such that they can be used in place non-recyclable epoxy compositions, without detriment.

This example demonstrates, vis-a-via chemical immersion weight gain tests, non-limiting examples of polyaminosilicon containing epoxy composition that has satisfactory chemical resistance against solvents. As a reference, Table 13 as provides a control epoxy system (Hexion 6150 system).

TABLE 14

$T_g$ and Chemical resistance data benchmarked against a non-recyclable epoxy used in automotive HP-RTM applications

|  | control epoxy | Acetal:PASi Wt ratio | | | Acetal:PASi Wt ratio | | |
| --- | --- | --- | --- | --- | --- | --- | --- |
|  |  | 25:75 | 50:50 | 75:25 | 25:75 | 50:50 | 75:25 |
| $T_g$ (° C.) | >110° C. | 133 | 118 | 103 | 119 | 107 | 109 |
| Water Boil (24 h) | <3.0% | 2.91 | 2.43 | 2.17 | 2.39 | 2.25 | 2.01 |
| Gasoline | <0.2% | 0.03 | 0.06 | 0.06 | 0.03 | 0.05 | 0.08 |
| Water | <0.4% | 0.27 | 0.25 | 0.27 | 0.27 | 0.28 | 0.27 |
| 5% AcOH | <0.5% | 0.30 | 0.47 | 0.75 | 0.27 | 0.28 | 0.18 |
| 1% H2SO4 | <1.0% | 0.35 | 0.43 | 0.85 | 0.39 | 0.83 | 2.31 |
| 10% H2SO4 | <2.5% | 0.64 | 0.85 | 1.25 | 1.93 | 4.88 | 12.81 |
| 1% HCl | <0.6% | 0.29 | 0.35 | 0.42 | 0.29 | 0.35 | 0.39 |
| 10% HCl | <1.0% | 0.45 | 0.51 | 0.57 | 0.69 | 1.38 | 2.88 |

Numbers in the table refer to the % weight gain of 20 g cured, epoxy disks, after immersion for 7 day at room temperature (20-25° C.). The control epoxy is Hexion 6150 system.

TABLE 15 provides the weight gain date after immersion of select recyclable epoxy compositions in water for 8 day and 45 days. The fact the weight gain number are not >several %, is indicative that the compositions are relatively stable to immersion in room temperature water (i.e. still thermoset), even though the compositions are recyclable due to the presences of hydrolyzable Si—O bonds in the cross-links.

TABLE 15

Weight gain date after immersion of select recyclable epoxy compositions in water for 8 day and 45 days

| COMPOUND | 8 DAY WT. GAIN | 45 DAY WT. GAIN |
|---|---|---|
| 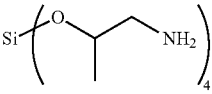 | 0.37% | 0.97% |
| 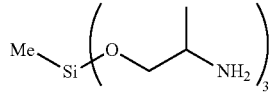 | 0.53% | 1.23% |
| 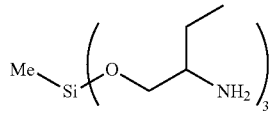 | 0.54% | 1.36% |
| 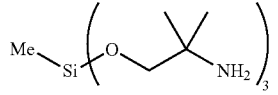 | 0.36% | 0.97% |
| 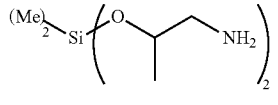 | 0.65% | 1.33% |
| 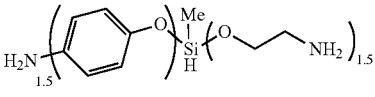 | nd | 1.1% |
| 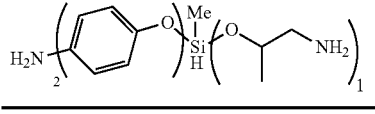 | nd | 1.0% |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound of Formula (I-A-iv)

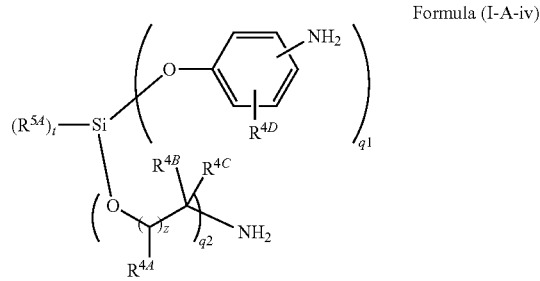

Formula (I-A-iv)

or a salt thereof, wherein:

z is an integer from 1 to 6;

t is an integer from 0 to 1;

q1 is an integer from 1 to 4;

q2 is an integer from 1 to 3;

each of $R^{4A}$, $R^{4B}$, $R^{4C}$, and $R^{4D}$ is independently for each occurrence hydrogen or alkyl; and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4.

2. The compound of claim 1, wherein the compound of Formula (I-A) is a compound of Formula (I-A-ii-1)

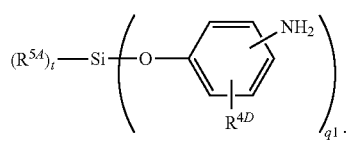

Formula (I-A-ii-1)

3. The compound of claim 1, wherein the compound is:

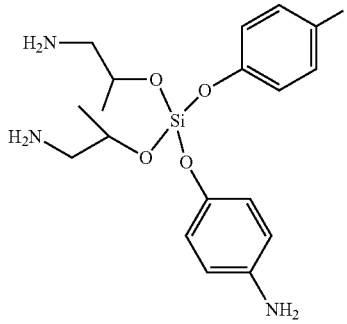

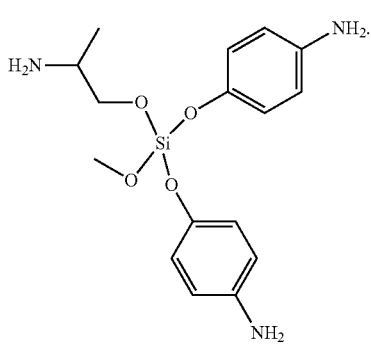

4. The compound of claim 3, wherein the compound is:

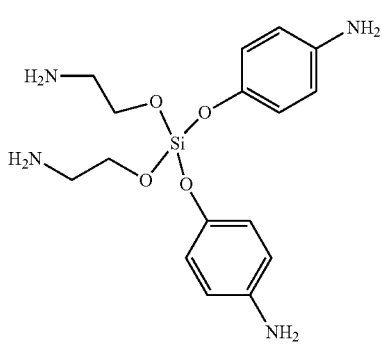

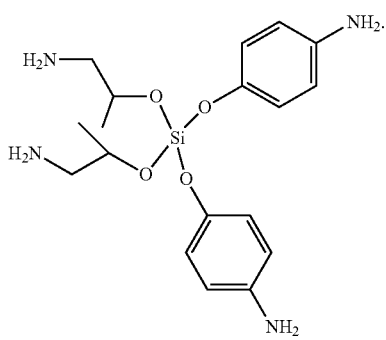

5. A composition comprising the reaction product of:
an epoxy resin; and
a compound of Formula (I-A-iv):

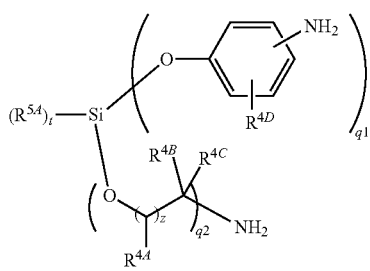

Formula (I-A-iv)

wherein:
z is an integer from 1 to 6;
t is an integer from 0 to 1;
q1 is an integer from 1 to 4;
q2 is an integer from 0 to 3;
each of $R^{4A}$, $R^{4B}$, $R^{4C}$, and $R^{4D}$ is independently for each occurrence hydrogen or alkyl;
and each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl, provided that the sum of t, q1, and q2 is 4.

6. The composition of claim 5, wherein the compound of Formula (I-A) is a compound of Formula (I-A-ii-1):

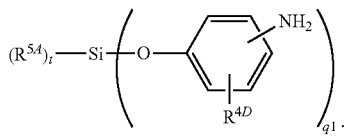

Formula (I-A-ii-1)

7. The composition of claim 5, wherein the compound of Formula (I-A) is:

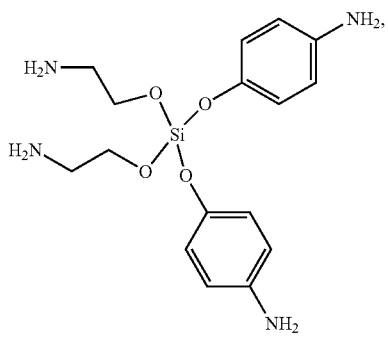

-continued

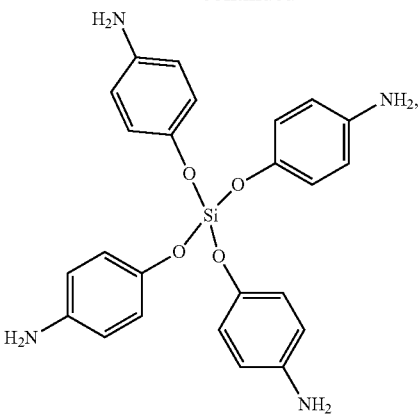

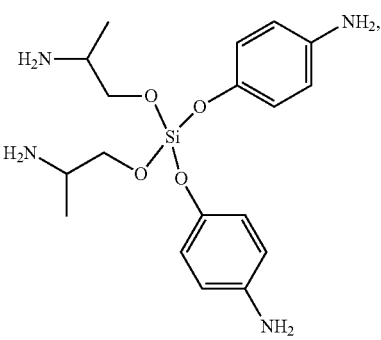

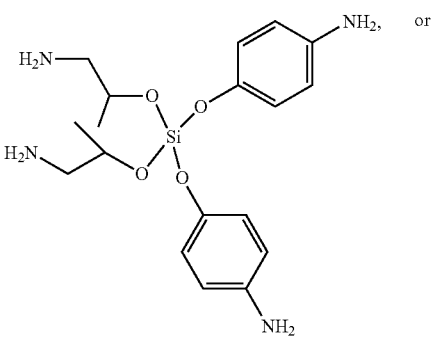

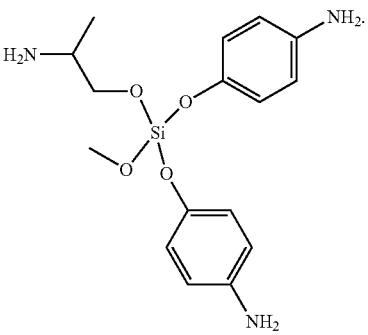

8. The composition of claim 7, wherein the compound of Formula (I-A) is:

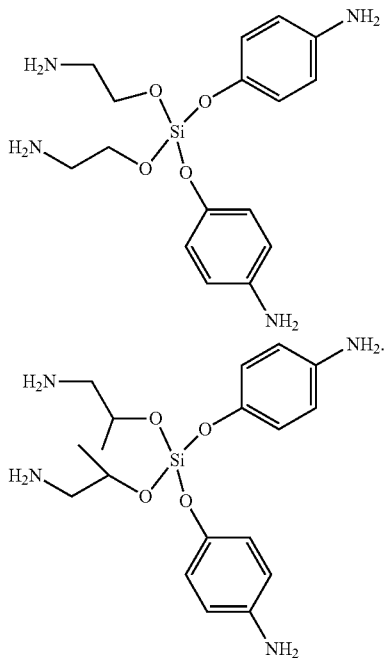

or

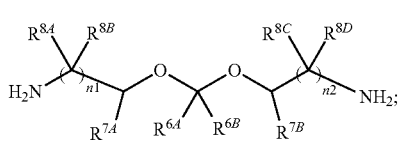

9. The composition of claim 5, wherein the epoxy resin comprises a diepoxide resin.

10. A composition comprising the reaction product of:
an epoxy resin;
a compound of Formula (I-A);

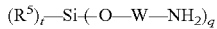   Formula (I-A)

wherein:
q is 4, 3, 2, or 1;
t is 0, 1, 2, or 3;
the sum of q and t is 4;
each occurrence of W is independently alkylene, cycloalkylene, heterocyclylene, alkenylene, alkynylene, cycloalkenylene, arylene, or heteroarylene; and
each occurrence of $R^5$ is independently hydrogen, alkyl, cycloalkyl, heterocyclyl, alkenyl, alkynyl, cycloalkenyl, aryl, heteroaryl or —$OR^C$, wherein $R^C$ is alkyl, cycloalkyl, heterocyclyl, alkenyl, alkynyl, cycloalkenyl, aryl or heteroaryl; and
a compound having the Formula (II-A-1):

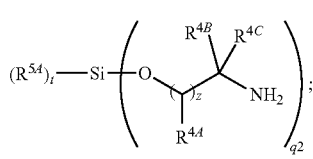   (II-A-1)

wherein: each of $R^{6A}$ and $R^{6B}$ is independently hydrogen or alkyl;
each of $R^{7A}$, $R^{7B}$, $R^{8A}$, $R^{8B}$, $R^{8C}$ and $R^{8D}$ is independently for each occurrence hydrogen or alkyl; and
each of n1 and n2 is independently 1 or 2.

11. A method for recycling the composition of claim 10, comprising contacting the composition with an acid.

12. The composition of claim 1, wherein the compound of Formula (I-A) is a compound of Formula (I-A-iv)

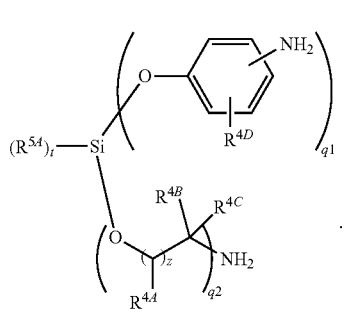   Formula (I-A-iv)

wherein:
z is an integer from 1 to 6; t is an integer from 0 to 1;
q1 is an integer from 0 to 4; q2 is an integer from 0 to 4;
each of $R^{4A}$, $R^{4B}$, $R^{4C}$, and $R^{4D}$ is independently for each occurrence hydrogen or alkyl; and
each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl,
provided that the sum of t, q1, and q2 is 4, and the sum of q1 and q2 is not 0.

13. The composition of claim 10, wherein the compound of Formula (I-A) is a compound of Formula (I-A-i-1) or (I-A-ii-1):

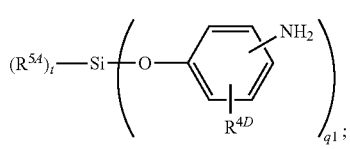   Formula (I-A-i-1)

Formula (I-A-ii-1)

wherein:
z is an integer from 1 to 6; each of $R^{4A}$, $R^{4B}$, $R^{4C}$, and $R^{4D}$ is independently for each occurrence hydrogen or alkyl; and
each occurrence of $R^{5A}$ is independently alkyl, cycloalkyl, aryl, or —$OR^C$, wherein $R^C$ is alkyl, cycloalkyl, heterocyclyl, alkenyl, alkynyl, cycloalkenyl, aryl or heteroaryl.

14. The composition of claim 10, wherein the compound of Formula (I-A) is a compound of Formula (I-A-iii):

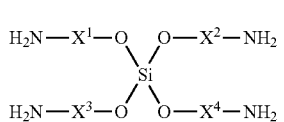   Formula (I-A-iii)

wherein:
each of $X^1$, $X^2$, $X^3$, and $X^4$ is independently alkylene, cycloalkylene, heterocyclylene, alkenylene, alkynylene, cycloalkenylene, arylene, or heteroarylene.
15. The composition of claim 10, wherein the compound of Formula (I-A) is:
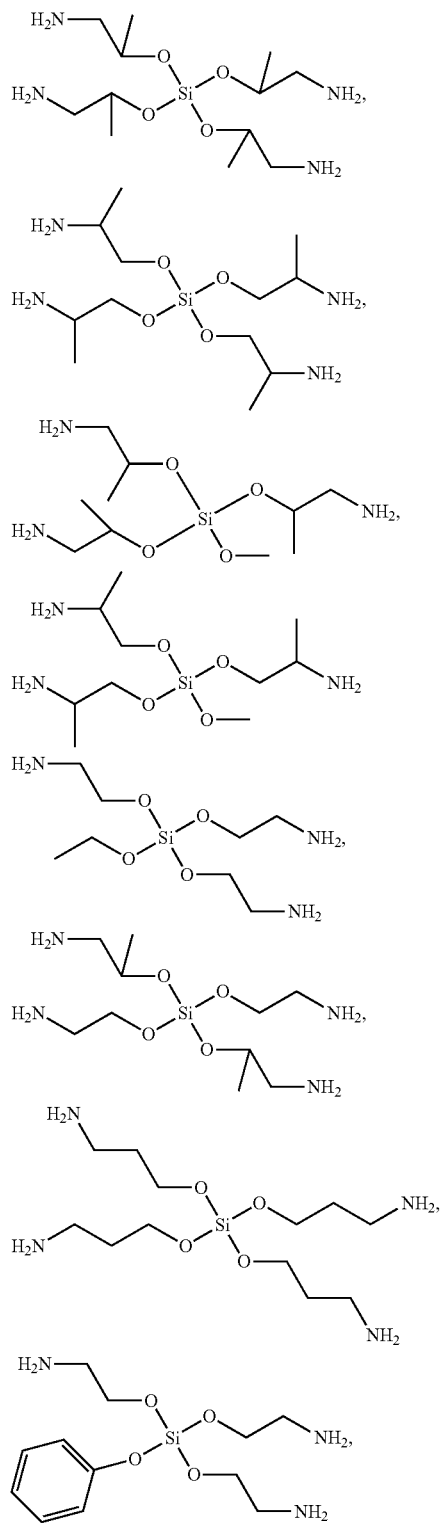
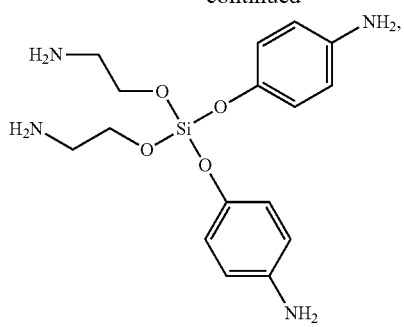

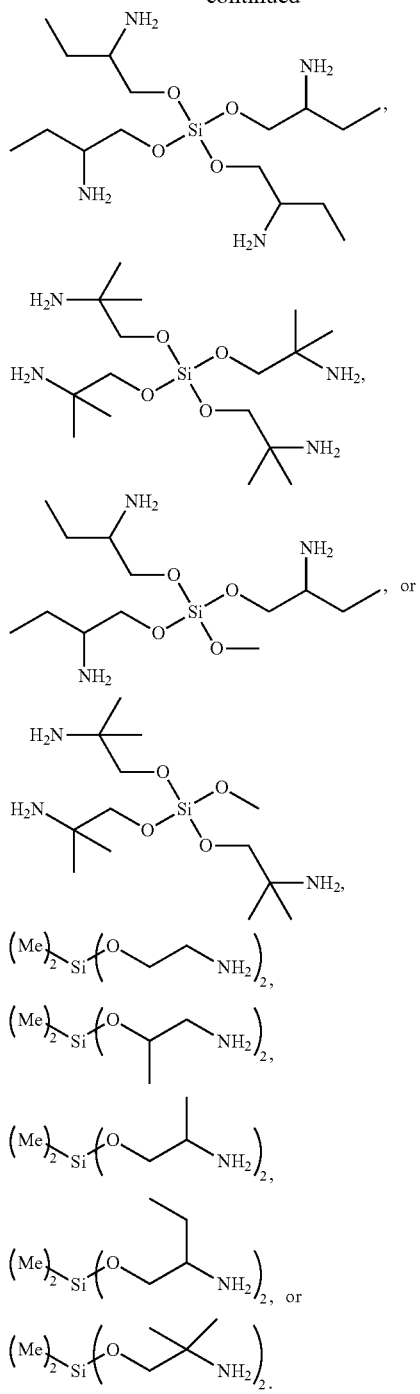
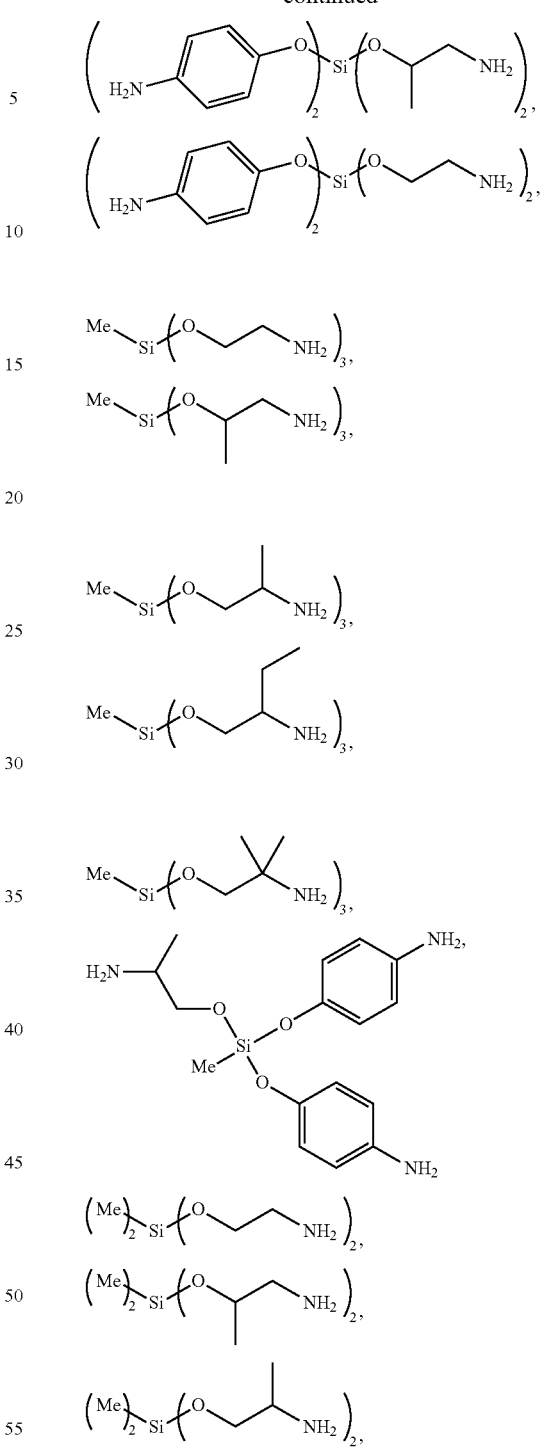
16. The composition of claim 10, wherein the compound of Formula (I-A) is:
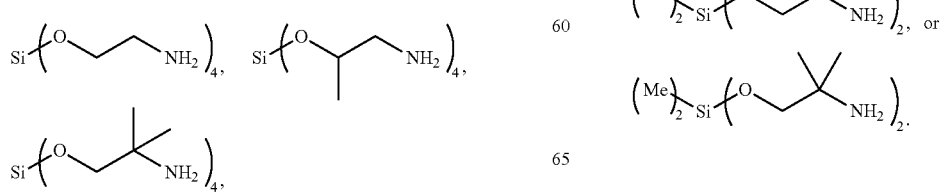

17. The composition of claim 16, wherein the compound of Formula (I-A) is:
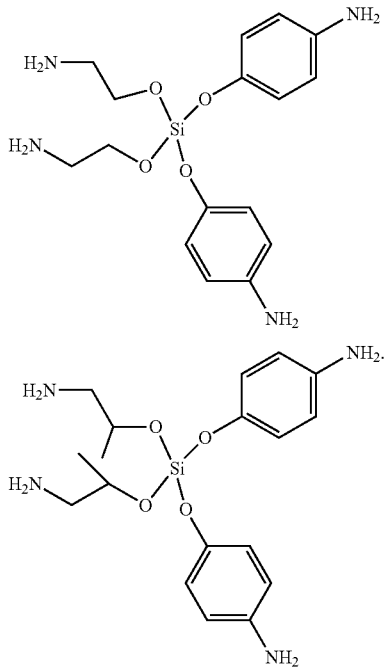
or
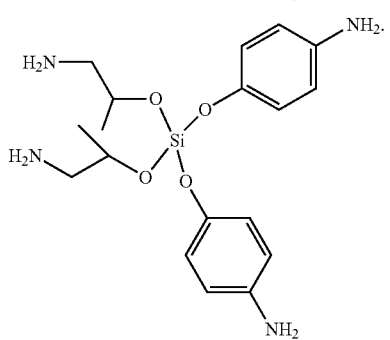
18. The composition of claim 10, wherein the compound of Formula (II-A-1) is:
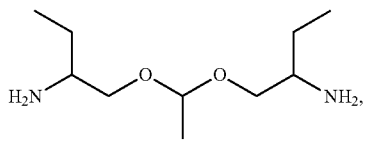
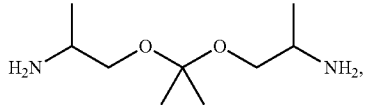
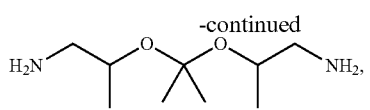
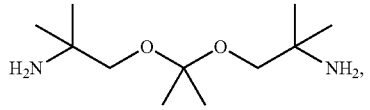
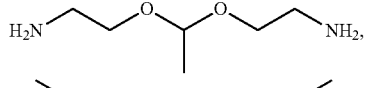
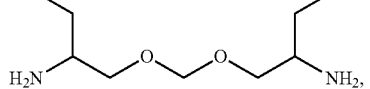
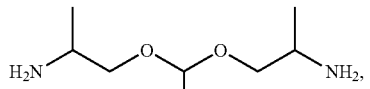
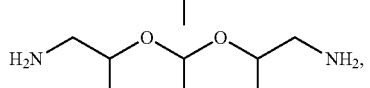
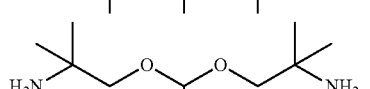
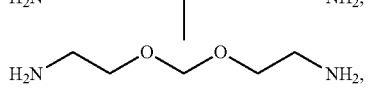
19. The composition of claim 10, wherein the composition comprises a chain extender.
20. The composition of claim 10, wherein the epoxy resin comprises a diepoxide resin.
* * * * *